US009822361B2

(12) United States Patent
Arhancet et al.

(10) Patent No.: US 9,822,361 B2
(45) Date of Patent: *Nov. 21, 2017

(54) COMPOSITIONS AND METHODS USING CAPSIDS RESISTANT TO HYDROLASES

(71) Applicant: APSE LLC, St. Louis, MO (US)

(72) Inventors: Juan Pedro Humberto Arhancet, St. Louis, MO (US); Juan P. Arhancet, St. Louis, MO (US); Kimberly Delaney, St. Louis, MO (US); Kathleen B. Hall, St. Louis, MO (US); Neena Summers, St. Louis, MO (US); Edward Oates, St. Louis, MO (US)

(73) Assignee: APSE, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/897,577

(22) PCT Filed: Jun. 5, 2014

(86) PCT No.: PCT/US2014/041111
§ 371 (c)(1),
(2) Date: Dec. 10, 2015

(87) PCT Pub. No.: WO2014/204667
PCT Pub. Date: Dec. 24, 2014

(65) Prior Publication Data
US 2016/0177299 A1 Jun. 23, 2016

Related U.S. Application Data

(60) Provisional application No. 61/836,833, filed on Jun. 19, 2013, provisional application No. 61/838,736, filed on Jun. 24, 2013, provisional application No. 61/857,965, filed on Jul. 24, 2013.

(51) Int. Cl.
C12N 15/11 (2006.01)
C12N 15/113 (2010.01)
A61K 48/00 (2006.01)
A61K 9/51 (2006.01)

(52) U.S. Cl.
CPC .......... C12N 15/113 (2013.01); A61K 9/5184 (2013.01); A61K 48/00 (2013.01); C12N 2310/12 (2013.01); C12N 2310/121 (2013.01); C12N 2310/14 (2013.01); C12N 2310/3519 (2013.01); C12N 2310/531 (2013.01); C12N 2795/00023 (2013.01); C12N 2795/00042 (2013.01)

(58) Field of Classification Search
CPC ........................ C12N 15/113; C12N 2310/12; C12N 2310/14
See application file for complete search history.

(56) References Cited

U.S. PATENT DOCUMENTS

| 5,443,969 | A | 8/1995 | Wilson et al. |
| 6,066,318 | A | 5/2000 | Feng et al. |
| 6,932,971 | B2 | 8/2005 | Bachmann et al. |
| 2003/0099668 | A1 | 5/2003 | Bachmann et al. |
| 2004/0171115 | A1 | 9/2004 | Feng et al. |
| 2005/0260758 | A1 | 11/2005 | Rasochova et al. |
| 2006/0177819 | A1 | 8/2006 | Smith et al. |
| 2008/0171361 | A1 | 7/2008 | Scheets et al. |
| 2008/0312176 | A1 | 12/2008 | Baulcombe et al. |
| 2009/0093019 | A1 | 4/2009 | Phelps et al. |
| 2010/0167981 | A1 | 7/2010 | Bundy et al. |
| 2011/0111481 | A1* | 5/2011 | Li ........................ C12N 15/111 435/252.3 |
| 2011/0250675 | A1 | 10/2011 | Bennett |
| 2011/0296556 | A1 | 12/2011 | Sammons et al. |
| 2012/0064169 | A1 | 3/2012 | Cheng et al. |
| 2012/0174263 | A1 | 7/2012 | Saunders et al. |
| 2012/0301494 | A1 | 11/2012 | Cheng et al. |
| 2013/0167267 | A1 | 6/2013 | Arhancet et al. |
| 2013/0224828 | A1* | 8/2013 | Finn ....................... C07K 19/00 435/188 |
| 2016/0194613 | A1* | 7/2016 | Williams ................. C12N 7/00 514/44 A |

FOREIGN PATENT DOCUMENTS

| WO | 02/056905 A2 | 7/2002 |
| WO | WO2005/001039 A2 * | 1/2005 |
| WO | WO2008/026015 * | 3/2008 |
| WO | WO 2009/095791 | 8/2009 |
| WO | WO 2011/116226 | 9/2011 |
| WO | 2012/051152 A2 | 4/2012 |
| WO | 2012/061445 A2 | 5/2012 |
| WO | WO 2013/096866 | 6/2013 |

(Continued)

OTHER PUBLICATIONS

Wu et al (Nanomedicine: Nanotechnology, Biology, and Medicine, 2005, 1: 67-76).*
Castanotto, D., et al., "Functional siRNA Expression from Transfected PCR Products," RNA, vol. 8, pp. 1454-1460 (Nov. 1, 2002).
Sasaki, J., et al., "Translation Initiation at the CUU Codon is Mediated by the Internal Ribosome Entry Site of an Insect Picornalike Virus in Vitro," Journal of Virology, vol. 73, No. 2, pp. 1219-1226 (Feb. 1999).
International Search Report of PCT/US2014/41111 dated Nov. 10, 2014.
Written Opinion of PCT/US2014/41111 dated Nov. 10, 2014.
Agbottah, E., et al., Antiviral Activity of CYC202 in HIV-1-infected Cells., J. Biol. Chem., vol. 280, pp. 3029-3042 (Jan. 28, 2005).
Altschul, S. F., et al, Basic Local Alignment Search Tool, J. Mol. Biol., vol. 215, No. 3, pp. 403-410 (Oct. 5, 1990).

(Continued)

Primary Examiner — Brian Whiteman
(74) Attorney, Agent, or Firm — Polsinelli PC

(57) ABSTRACT

Novel processes and compositions are described which use viral capsid proteins resistant to hydrolases to prepare virus-like particles to enclose and subsequently isolate and purify target cargo molecules of interest including nucleic acids such as siRNAs and shRNAs, miRNAs, messenger RNAs, small peptides and bioactive molecules.

6 Claims, 19 Drawing Sheets

(56) References Cited

FOREIGN PATENT DOCUMENTS

WO     WO2013096866 A2 * 6/2013

OTHER PUBLICATIONS

Amarzguioul, M., et al., "Hammerhead Ribozyme Design and Application," Cell. Mol. Life Sci., vol. 54, pp. 1175-1202 (Nov. 1998).

Ashley, C. E., et al., "Cell-Specific Delivery of Diverse Cargos by Bacteriophage MS2 Virus-Like Particles," Acs Nano, vol. 5, No. 7, pp. 5729-5745 (Jun. 7, 2011).

Askonas, B.A., "The Use of Organic Solvents at Low Temperature for the Separation of Enzymes. Application to Aqueous Rabbit Muscle Extract," Biochemical Journal, vol. 48, No. 1, pp. 42-48 (Jan. 1951).

Ayuso-Tejedor, S., et al., "Underexposed Polar Residues and Protein Stabilization," Protein Engineering, Design & Selection, vol. 24, Issue 1-2; pp. 1-7 (Oct. 11, 2010).

Beames, B., et al., "Insertions within the Hepatitis B Virus Capsid Protein Influence Capsid Formation and RNA Encapsidation," J. Virology, vol. 69, No. 11, pp. 6833-6838 (Nov. 1995).

Been, M.D., et al., "Optimal Self-Cleavage Activity of the Hepatitis Delta Virus Rna is Dependent on a Homopurine Base Pair in the Ribozyme Core," RNA, vol. 1, pp. 1061-1070 (Dec. 1995).

Benson, D. A., et al., GenBank, Nucleic Acids Res., vol. 33, pp. D34-D38, (Jan. 1, 2005).

Brustad, E., et al., "A Genetically Encoded Boronate-Containing Amino Acid," Angew. Chem., vol. 120, Issue 43, pp. 8344-8347 (Sep. 24, 2008).

Burster, T., et al., "Design of Protease-Resistant Myelin Basic Protein-Derived Peptides by Cleavage Site Directed Amino Acid Substitutions," Biochemical Pharmacology, vol. 74, pp. 1514-1523 (Nov. 15, 2007).

Carr, P. A, et al., "Genome Engineering," Nature Biotechnology, vol. 27, pp. 1151-1162 (Dec. 9, 2009).

Cellitti, S.E., et al., "In vivo Incorporation of Unnatural Amino Acids to Probe Structure, Dynamics, and Ligand Binding in a Large Protein by Nuclear Magnetic Resonance Spectroscopy," J. Am. Chem. Soc., vol. 130, No. 29, pp. 9268-9281 (Jul. 23, 2008).

Chang, J. R., et al., "Incorporation of Scaffolding Protein gpO in Bacteriophages P2 and P4," Virology, vol. 370, No. 2, pp. 352-361 (Jan. 2008).

Cheng, Y., et al., "Preparation of His-Tagged Armored RNA Phage Particles as a Control for Real-Time Reverse Transcription-PCR Detection of Severe Acute Respiratory Syndrome Coronavirus," Journal of Clinical Microbiology, vol. 44, No. 10, pp. 3557-3561 (Oct. 2006).

Chomczynski, P., et al., "The Single-Step Method of RNA Isolation by Acid Guanidinium Thiocyanate-Phenol-Chloroform Extraction: Twenty-Something years on," Nature Protocols, vol. 1, No. 2, pp. 581-585 (Jun. 27, 2006 published online).

Chothia, C., et al., "Domain Association in Immunoglobulin Molecules the Packing of Variable Domains," J. Mol. Biol., vol. 186, Issue 3, pp. 651-663 (Dec. 5, 1985).

Chothia, C., et al., "The Relation Between the Divergence of Sequence4 and Structure in Proteins," EMBO J., vol. 5, No. 4, pp. 823-826 (Apr. 1986).

Clark, S. M., "Trypsin Enhancement of Rotavirus Infectivity: Mechanism of Enhancement," Journal of Virology, vol. 39, No. 3, pp. 816-822 (Sep. 1981).

Davis, M., et al., "Evidence of RNAi in Humans from Systemically Administered siRNA via Targeted Nanoparticles," Nature, vol. 464, pp. 1067-1070 (Apr. 15, 2010).

Draghi, J. A., et al., "Mutational Robustness can Facilitate Adaptation," Nature, vol. 463, pp. 353-355 (Jan. 21, 2010).

Everts, S., "New Sensor for Cell Metabolites," Chemical & Engineering News, vol. 90, No. 11 (Mar. 12, 2012).

Feng, Y., et al., "Three-dimensional Solution Structure and Backbone Dynamics of a Variant of Human Interleukin-3," J. Mol. Biol., vol. 259, pp. 524-541 (Jun. 14, 1996).

Ferré-D'Amaré, A., et al., "Small Self-Cleaving Ribozymes," Cold Spring Harb. Perspect. Biol., vol. 2, No. 10, a003574 (Oct. 2010) published online Sep. 15, 2010.

Ferre-D'Amare, A., et al., "Use of cis-and trans-ribozymes to Remove 5' and 3' Heterogeneities from Milligrams of in Vitro Transcribed RNA," Nucleic Acids Research, vol. 24, No. 5, pp. 977-978 (Jan. 1, 1996).

Fiedler, J., et al., RNA-Directed Packaging of Enzymes within Virus-like Particles, Angew. Chem. Int. Ed., vol. 49, No. 50, pp. 9648-9651 (Dec. 10, 2010).

Fischlechner, M., et al., "Viruses as Building Blocks for Materials and Devices," Angew. Chem. Int. Ed., vol. 46, pp. 3184-3193 (Mar. 9, 2007).

Fraczkiewicz , R., et al., "Exact and Efficient Analytical Calculation of the Accessible Surface Areas and Their Gradients for Macromolecules," J. Computational Chemistry, vol. 19, No. 3, pp. 319-333 (Feb. 1998).

Gailus, V., et al., "The Absorption Protein of Bacteriophage fd and its Neighbour Minor Coat Protein Build a Structural Entity," Eur. J. Biochem., vol. 222, pp. 927-931 (Jun. 1994).

Gottschalk, U., "Bioseparation in Antibody Manufacturing: The Good, The Bad and The Ugly," Biotechnol. Prog., vol. 24, pp. 496-503 (May 2008).

Hammill, J. T., et al., "Preparation of Site-Specifically Labeled Fluorinated Proteins for $^{19}$F-NMR Structural Characterization," Nature Protocols, vol. 2, No. 10, pp. 2601-2607 (Oct. 18, 2007).

Haussecker, D., "The Business of RNAi Therapeutics," Human Gene Therapy, vol. 19, pp. 451-462 (May 2008).

International Search Report and Written Opinion of PCT/US2012/071419 dated Jul. 22, 2013.

International Search Report from the Intellectual Property Office of Singapore for SG Application No. 11201510181Y dated Oct. 25, 2016.

International Search Report of PCT/US14/55426 dated Mar. 3, 2015.

Jegerlehner, A., et al., "TLR9 Signaling in B Cells Determines Class Switch Recombination to IgG2a," J. Immunol., vol. 178, pp. 2415-2420 (Feb. 15, 2007).

Johnson, H. R., et al, "Solubilization and Stabilization of Bacteriophage MS2 in Organic Solvents," Biotechnology and Bioengineering, vol. 97, No. 2, pp. 224-234 (Jun. 1, 2007).

Jung, S., et al., "Limited Hydrolysis of Soy Proteins with Endo- and Exproteases," Journal of the American Oil Chemists' Society, vol. 81, pp. 953-970 (Oct. 2004).

Kamtekar, S., et al., "Protein Design by Binary Patterning of Polar and Nonpolar Amino Acids," Science, vol. 262, pp. 1680-1685 (Dec. 10, 1993).

Karlin, S., et al., "Methods for Assessing the Statistical Significance of Molecular Sequence Features by Using General Scoring Schemes," PNAS, vol. 87, pp. 2264-2268 (Mar. 1990).

Kastelein, R.A., et al., "Lysis Gene Expression of RNA Phage MS2 Depends on a Frameshift During Translation of the Overlapping Coat Protein Gene," Nature, vol. 295, pp. 35-41 (Jan. 1982).

Kawasaki, H., et al., "World of Small RNAs: From Ribozymes to siRNA and miRNA," Differentiation, vol. 72, pp. 58-64 (Mar. 2004).

Kelley, B., "Very Large Scale Monoclonal Antibody Purification: The Case for Conventional Unit Operations," Biotechnol. Prog., vol. 23, Issue 5, pp. 995-1008 (Sep.-Oct. 2007).

Kleywegt, G. J., et al., "Phi/Psi-chology: Ramachandran revisited," Structure, vol. 4, pp. 1395-1400 (Dec. 15, 1996).

Kozak, M., et al., "Fate of Maturation Protein During Infection by Coliphage MS2," Nature New Biology, vol. 234, pp. 209-211 (Dec. 15, 1971).

Kuzmanovic, D., et al., "The MS2 Coat Protein Shell is Likely Assembled Under Tension: A Novel Role for the MS2 Bacteriophage a Protein as Revealed by Small-angle Neutron Scattering," J. Mo.. Biol., vol. 355, No. 5, pp. 1095-1111 (Feb. 3, 2006).

Lee, J., et al., "Receptor Mediated Uptake of Peptides that Bind the Human Transferrin Receptor," Eur. J. Biochem., vol. 268, pp. 2004-2012 (Apr. 2001).

(56) References Cited

OTHER PUBLICATIONS

Legendre, D., et al., "Production in Saccharomyces Cerevisiae of MS2 Virus-Like Particles Packaging Functional Heterologous mRNAs,"Journal of Biotechnology, vol. 117, pp. 183-194 (May 4, 2005).
Lesur, A., et al., "Accelerated Tryptic Digestion for the Analysis of Biopharmaceutical Monoclonal Antibodies in Plasma by Liquid Chromatography with Tandem Mass Spectrometric Detection," Journal of Chromatography A., vol. 1217, Issue 1, pp. 57-64 (Jan. 1, 2010).
Li, H., et al., "Fat Fractal and Multifractals for Protein and Enzyme Surfaces," Int. J. Biol. Macromol., vol. 13, pp. 210-216 (Aug. 1991).
Li, T. C., et al., "Essential Elements of the Capsid Protein for Self-Assembly into Empty Virus-Like Particles of Hepatitis E Virus," J. Virology, vol. 79, No. 20, pp. 12999-13006 (Oct. 2005).
Liljas, L., et al., "Crystal Structure of Bacteriophage fr Capsids at 3.5 Å Resolution," J. Mol. Biol., vol. 244, pp. 279-290 (Dec. 13, 1994).
Low, D. R., et al., "Future of Antibody Purification," Journal of Chromatography B, vol. 848, No. 1, pp. 48-63 (Mar. 15, 2007) published online Nov. 28, 2006.
Marin, B., et al., "Solubilization and Purification of the ATPase from the Tonoplast of Hevea," Eur. J. Biochem, vol. 151, pp. 131-140 (May 14, 1985).
Marsh, E. N., et al., "Fluorine—a new element in the Design of Membrane-Active Peptides," Molecular BioSystems, vol. 5, pp. 1143-1147 (Jul. 28, 2009).
Maruyama, I. N., et al., "λfoo: A λ Phage Vector for the Expression of Foreign Proteins," Proc. Natl. Acad. Sci. USA, vol. 91, pp. 8273-8277 (Aug. 1994).
Matlin, K. S., et al., "Pathway of Vesicular Stomatitis Virus Entry Leading to Infection," J. Mol. Biol., vol. 156, pp. 609-631 (Apr. 15, 1982).
Mazzola, P. G., et al., "Liquid-liquid Extraction of Biomolecules: An Overview and Update of the Main Techniques," Journal of Chemical Technology & Biotechnology, vol. 83, No. 2, pp. 143-157 (Feb. 2008) published on-line Dec. 11, 2007.
Micura, R., Small Interfering RNAs and Their Chemical Synthesis,: Angew chem. Int. Ed., vol. 41, pp. 2265-2269 (Jul. 1, 2002).
Miyaura, N., et al., "Palladium-Catalyzed Cross-Coupling Reactions of Organoboron Compounds," Chem. Rev., vol. 95, No. 7, pp. 2457-2483 (Nov. 1, 1995).
Morgenstern, B., et al., "Multiple Sequence Alignment With User-Defined Anchor Points," Algorithms for Molecular Biology, vol. 1, No. 6, pp. 1-12 (Apr. 19, 1996).
Murzin, A.G., "Structural classification of proteins: new superfamilies," Curr. Opin. Struct. Biol., vol. 6, Issue 3, pp. 386-394 (Jun. 1996).
Nasser, A. M., et al., "Contribution of Microbial Activity to Virus Reduction in Saturated Soil," Water Research, vol. 36, pp. 2589-2595 (May 2002).
Nelson, A. L., et al., "Development Trends for Human Monoclonal Antibody Therapeutics," Nature Reviews—Drug Discovery, vol. 9, pp. 767-774 (Oct. 2010).
Ochoa, W.F., et al., "Generation and Structural Analysis of Reactive Empty Particles Derived from an Icosahedral Virus," Chemistry & Biology, vol. 13, No. 7, pp. 771-778 (Jul. 2006).
Olins, P. O., et al, "Saturation Mutagenesis of Human Interleukin-3," J. Biol. Chem., vol. 270, No. 40, pp. 23754-23760 (Oct. 6, 1995).
Paige, J., et al., "RNA Mimics of Green Fluorescent Protein," Science, vol. 333, pp. 642-646 (Jul. 2011).
Pan, Y., et al., "Development of a microRNA Delivery System Based on Bacteriophage MS2 Virus-Like Particles," FEBS J, vol. 279, No. 7, pp. 1198-12108 (Feb. 23, 2012).
Patkar, C. G., et al, "Functional Requirements of the Yellow Fever Virus Capsid Protein," J. Virology, vol. 81, No. 12, pp. 6471-6481 (Jun. 2007) published online Apr. 4, 2007.
Pattenden, L. K., et al., "Towards the Preparative and Large-Scale Precision Manufacture of Virus-Like Particles," Trends in Biotechnology, vol. 23, No. 10, pp. 523-529 (Oct. 2005).
Peabody, D. S., et al., "Immunogenic Display of Diverse Peptides on Virus-like Particles of RNA Phage MS2," J. Mol. Biol., vol. 380, No. 1, pp. 252-263 (Jun. 27, 2008).
Pearson, W. R., et al., "Improved tools for biological sequence comparison," PNAS, vol. 85, No. 8, pp. 2444-2448 (Apr. 1, 1988).
Pecson, B., et al., "Quantitative PCR for Determining the Infectivity of Bacteriophage MS2 upon Inactivation by Heat, UV-B Radiation, and Singlet Oxygen: Advantages and Limitations of an Enzymatic Treatment to Reduce False-Positive Results," Applied and Environmental Microbiology, vol. 75, No. 17, pp. 5544-5554 (Sep. 2009).
Petruzziello, R., et al., "Pathway of Rubella Virus Infectious Entry into Vero Cells," Journal of General Virology, vol. 77, pp. 303-308 (Jan. 2, 1996).
Pettersen, E. F., et al., "UCSF Chimera—A Visualization System for Exploratory Research and Analysis," J. Comput. Chem., vol. 25, pp. 1605-1612 (2004).
Pickett, G., et al., "Encapsidation of Heterologous RNAs by Bacteriophage MS2 Coat Protein," Nucleic Acids Research, vol. 21, No. 19, pp. 4621-4626 (Sep. 25, 1993).
Plevka, P., et al., "Crystal packing of a bacteriophage MS2 coat protein mutant corresponds to octahedral particles," Protein Science, vol. 17, Issue 10, pp. 1731-1739 (Oct. 2008).
Prlic, A., et al., "Pre-calculated protein structure alignments at the RCSB PDB website, Bioinformatics," vol. 26, No. 23, pp. 2983-2985 (Oct. 10, 2010).
Przybycien, T. M., et al., "Alternative Bioseparation Operations: Life Beyond Packed-Bed Chromatography," Current Opinion in Biotechnology, vol. 15, No. 5, pp. 469-478 (Oct. 2004) published online Sep. 11, 2004.
rcsb.org website, RCSB information Portal to Biological Macromolecular Structures, http://www.rcsb.org/pdb/home/home.do, two pages.
rcsb.org website, RCSB PDB Protein Comparison Tool, http://www.rcsb.or/pdb/workbench/workbench.do, one page.
Reis, P., et al., "Lipases at Interfaces: A Review.: Advances in Colloid and Interface Science," vol. 147-148, pp. 237-250 (Jun. 2009).
Rennell, D., et al., "Systematic Mutation of Bacteriophage T4 Lysozyme," J. Mol. Biol., vol. 222, pp. 67-87 (Nov. 5, 1991).
Rhee, J. K., et al, "Colorful Virus-Like Particles: Fluorescent Protein Packaging by the Qbeta Capsid," Biomacromolecules, vol. 12, No. 11, pp. 3977-3981 (Oct. 13, 2011).
Rohrmann, G. F., et al., "Physical, Biochemical, and Immunological Properties of Coliphage MS-2 Particles," J. Virol., vol. 6, No. 3, pp. 269-279 (Sep. 1970).
Sanjuán, R., et al., "Viral Mutation Rates," Journal of Virology, vol. 84, No. 19, pp. 9733-9748 (Oct. 2010).
Schmid, F. X., "Selecting Proteins with Improved Stability by a Phage-based Method," Nature Biotechnology, vol. 16, pp. 955-960 (Sep. 1, 1998).
Schwind, P., et al., "Subtilisin Removes the Surface Layer of the Phage fd Coat." Eur. J. Biochem., vol. 210, pp. 431-436 (Dec. 1992).
Sett, A., et al, "Aptasensors in Health, Environment and Food Safety Monitoring," Open J. Applied Biosensor, vol. 1, No. 2, pp. 9-19 (Aug. 2012).
Shenton, W., et al., "Synthesis of Nanophase Iron Oxide in Lumazine Synthase Capsids," Angew. Chem. Int. Ed., vol. 40, No. 2, pp. 442-445 (Jan. 2001).
Sieber, V., et al., "Selecting Proteins With Improved Stability by a Phage-Based Method," Nature Biotechnology, vol. 16, pp. 955-960 (Oct. 1998).
Simon, L. D., et al., "Stabilization of Proteins by a Bacteriophage T4 Gene Cloned in *Escherichia coli*," Proc. Natl. Acad. Sci. USA, vol. 80, pp. 2059-2062 (Apr. 1983).
Sinha, J., et al., Reprogramming Bacteria to Seek and Destroy a Herbicide, Nat Chem. Biol., vol. 6, No. 6, pp. 464-470 (May 9, 2010).

(56) References Cited

OTHER PUBLICATIONS

Song, H., et al., "Reactions in Droplets in Microfluidic Channels," Angew. Chem. Int. Ed. Engl., vol. 45, No. 44, pp. 7336-7356 (Nov. 13, 2006).
Sousa, R., et al., "'Model for the Mechanism of Bacteriophage T7 RNAP Transcription Initiation and Termination," J. Mol. Biol., vol. 224, Issue 2, pp. 319-334 (Mar. 20, 1992).
Stockley, P., et al., "Packaging Signals in Single-Stranded RNA Viruses: Nature's Alternative to a Purely Electrostatic Assembly Mechanism," J Biol. Phys., vol. 39, pp. 277-287 (Mar. 2013).
Stockley, P. G., et al., "A Simple, RNA-Mediated Allosteric Switch Controls the Pathway to Formation of a T=3 Viral Capsid," J. Mol. Biol., vol. 369, Issue 2, pp. 541-552 (Mar. 15, 2007 published on-line).
Strauss, J. H., et a ., "Purification and Properties of Bacteriophage MS2 and of its Ribonucleic Acid," J. Mol. Biol., vol. 7, pp. 43-54 (Jul. 1963).
Studier, F. W., et al., "Use of Bacteriophage T7 RNA Polymerase to Direct Selective High-level Expression of Cloned Genes," J. Mol. Biol., vol. 189, Issue 1, pp. 113-130 (May 5, 1986).
Tars, K., et al, "The Crystal Structure of Bacteriophage GA and a Comparison of Bacteriophages Belonging to the Major Groups of *Escherichia coli* Leviviruses," J. Mol. Biol., vol. 271, Issue 5, pp. 759-773 (Sep. 5, 1997).
The Protein Data Bank, A computer-based Archival File for Macromolecular Structures, J. Mol. Biol., 1977, pp. 535-542, vol. 112 (Feb. 1977).
The UniProt Consortium, "Reorganizing the protein space at the Universal Protein Resource," Nucleic Acids Research, vol. 40, Issue D1, pp. D71-D75 (Nov. 17, 2011).
Toropova, K., et al., "The Three-Dimensional Structure of Genomic RNA in Bacteriophage MS2: Implications for Assembly," J. Mol. Biol., vol. 375, Issue 3, pp. 824-836 (Jan. 18, 2008).
Uniprot.Org website, Welcome page: Resource of protein sequence and functional information, http://www.uniprot.org, Jan. 15, 2013, one page.
Valegard, K., et al., "The Three-Dimensional Structure of the Bacterial Virus MS2," Nature, vol. 345, pp. 36-41 (May 3, 1990).
Van Den Worm, S., et al., "Crystal Structures of Ms2 Coat Protein Mutants in Complex With Wild-Type RNA Operator Fragments," Nucleic Acids Research, vol. 26, No. 5, pp. 1345-1351 (Mar. 1, 1998).
Van Loo, B., et al., Directed Evolution of Epoxide Hydrolase from A. Radiobacter toward Higher En CZfantioselectivity by Error-Prone PCR and DNA Shuffling, Chemistry & Biology, vol. 11, pp. 981-990 (Jul. 2004).
Varadwaj, P., et al., "Surface Roughness Index, A Novel Approach to Compare Protein Surfaces," Proceedings of International Conference on Intelligent Sensing and Information Processing, pp. 474-478 (Conference held Jan. 4-7, 2005).
Vogels, G., et al., "Combination of Enzymatic and/or Thermal Pretreatment with Mechanical Cell Disintegration," Chemical Engineering Science, vol. 47, No. 1., pp. 123-131 (Jan. 1992).
Walker, S. C., et al., "Proteolytic Inactivation of Simian-11 Rotavirus: a Pilot Study," vol. 74, pp. 195-206 (Jun. 1, 2000).
Walton, S. P., et al., "Designing Highly Active siRNAs for Therapeutic Applications," FEBS Journal, vol. 277, No. 23, pp. 4806-4813 (Dec. 2010).
Wan, Y. S., et al., "Separation of Monoclonal Antibody Alemtuzumab Monomer and Dimers Using Ultrafiltration," Biotechnology and Bioengineering, vol. 90, No. 4, pp. 422-432 (May 20, 2005).
Wei, Y., et al., "RNase-Resistant Virus-Like Particles Containing Long Chimeric RNA Sequences Produced by Two-Plasmid Coexpression System," J. Clin. Microbiol., vol. 46, No. 5, pp. 1734-1740 (May 2008).
Wigginton, K., et al., "Oxidation of Virus Proteins During UV254 and Singlet Oxygen Mediated Inactivation," Environ. Sci. Technol., vol. 55, pp. 5437-5443 (May 17, 2010).
Wimmer, E., et al., "Synthetic Viruses: A New Opportunity to Understand and Prevent Viral Disease," Nature Biotechnology, vol. 27, No. 12, pp. 1163-1172 (Dec. 2009).
Wörsdörfer, B., et al., "Directed Evolution of a Protein Container," Science, vol. 331, pp. 589-592 (Feb. 4, 2011).
Written Opinion of PCT/US14/55426 dated Mar. 3, 2015.
Wu, M., et al, "Delivery of antisense oligonucleotides to leukemia cells by RNA bacteriophage capsids," Nanomedicine: Nanotechnology, Biology and Medicine, vol. 1, pp. 67-76 (Mar. 2005).
Xie, J., et al., A Chemical Toolkit for Proteins—an Expanded Genetic Code, Nature Reviews, Molecular Cell Biology, vol. 7, pp. 775-782 (Oct. 2006).
Young, et al., "An Enhanced System for Unnatural Amino Acid Mutagenesis in *E. coli*," J. Mol. Biol., vol. 395, Issue 2, pp. 361-374 (Jan. 15, 2010).
Zlotnick, A., et al., "Localization of the C terminus of the assembly domain of hepatitis B virus capsid protein: Implications for morphogenesis and organization of encapsidated RNA," PNAS, vol. 94, No. 18, pp. 9556-9561 (Sep. 2, 1997).
U.S. Appl. No. 13/725,184—Restriction Requirement dated Sep. 16, 2015.
U.S. Appl. No. 13/725,184—Non-final office action dated May 5, 2016.
U.S. Appl. No. 13/725,184—Notice of Non-Responsive Amendment dated Jul. 29, 2016.
U.S. Appl. No. 13/725,184—Final Office Action dated Nov. 22, 2016.
U.S. Appl. No. 14/279,793—Non-Final Office Action dated Aug. 13, 2014.
U.S. Appl. No. 14/279,793—Final Office Action dated Feb. 9, 2015.
U.S. Appl. No. 14/279,793—Notice of Allowance dated Oct. 2, 2015.

\* cited by examiner

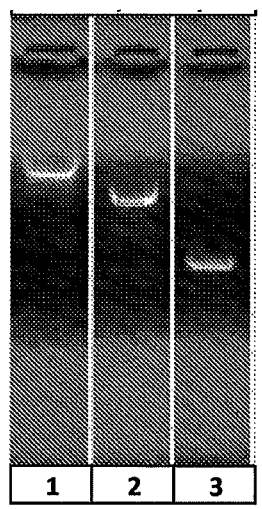 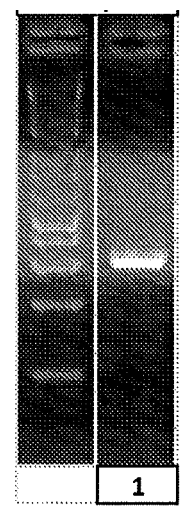
FIGURE 9    FIGURE 10

COMPOSITIONS AND METHODS USING CAPSIDS RESISTANT TO HYDROLASES

CROSS REFERENCE TO RELATED APPLICATIONS

A computer readable text file, entitled "PCT-APSE-SEQ_ST25.txt", created on or about Dec. 10, 2015, with a file size of about 32 kb, contains the sequence listing for this application and is hereby incorporated by reference in its entirety.

INCORPORATION OF SEQUENCE LISTING

The entire contents of a paper copy of the "Sequence Listing" and a computer readable form of the sequence listing on optical disk, containing the file named 450061_SequenceListing_ST25.txt, which is 32 kilobytes in size and was created on Jun. 3, 2014, are herein incorporated by reference.

TECHNICAL FIELD

The invention relates to virus-like particles, and in particular to methods and compositions using viral capsids as nanocontainers for producing, isolating and purifying heterologous nucleic acids with particular characteristics and functions.

BACKGROUND OF THE INVENTION

Virus-like particles (VLPs) are particles derived in part from viruses through the expression of certain viral structural proteins which make up the viral envelope and/or capsid, but VLPs do not contain the viral genome and are non-infectious. VLPs have been derived for example from the Hepatitis B virus and certain other viruses, and have been used to study viral assembly and in vaccine development.

Viral capsids are composed of at least one protein, several copies of which assemble to form the capsid. In some viruses, the viral capsid is covered by the viral envelope. Such viral envelopes are comprised of viral glycoproteins and portions of the infected host's cell membranes, and shield the viral capsids from large molecules that would otherwise interact with them. The capsid is typically said to encapsidate the nucleic acids which encode the viral genome and sometimes also proteins necessary for the virus' persistence in the natural environment. For the viral genome of a virus to enter a new host, the capsid must be disassembled. Such disassembly happens under conditions normally used by the host to degrade its own as well as foreign components, and most often involves proteolysis. Viruses take advantage of normal host processes such as proteolytic degradation to enable that critical part of their cycle, i.e. capsid disassembly and genome release.

It is therefore unsurprising that the literature has not previously described capsids resistant to hydrolases that act on peptide bonds. A very limited number of certain specific peptide sequences which are part of larger proteins are known to be somewhat resistant to certain proteases, but the vast majority of peptide sequences are not. Viruses that resist proteolysis have been reported, but these are all enveloped viruses, in which the capsid is shielded by the viral envelope. In such viruses the capsids are not in contact with, i.e. they are shielded from, the proteases described. Thus the role, if any, of the proteolytical stability of the virus capsid in such cases is unknown.

In large-scale manufacturing of recombinant molecules such as proteins, ultrafiltration is often used to remove molecules smaller than the target protein in the purification steps leading to its isolation. Purification methods also often involve precipitation, solvent extraction, and crystallization techniques. These separation techniques are inherently simple and low cost because, in contrast to chromatography, they are not based on surface but on bulk interactions. However, these techniques are typically limited to applications to simple systems, and by the need to specify a different set of conditions for each protein and expression system. Yet each target recombinant protein presents a unique set of binding interactions, thereby making its isolation process unique and complex. The separation efficiency for recombinant proteins using these simple isolation processes is therefore low.

Nucleic acids, including siRNA and miRNA, have for the most part been manufactured using chemical synthesis methods. These methods are generally complex and high cost because of the large number of steps needed and the complexity of the reactions which predispose to technical difficulties, and the cost of the manufacturing systems. In addition, the synthetic reagents involved are costly and so economy of scale is not easily obtained by simply increasing batch size.

Chemically and enzymatically synthesized RNA is commonly used for RNAi applications, mostly for down-regulation or repression of expression of proteins. Examples of RNA delivered into organisms for up-regulation of expression of endogenous proteins or expression of exogenous proteins are very limited. A previously described method for delivering mRNA to the body is limited to 5' capped RNA which is difficult to synthesize. A need remains for improved and cost-effective RNA delivery methods and methods for both RNAi and mRNA applications.

BRIEF SUMMARY OF THE INVENTION

In one aspect the present disclosure provides a VLP comprising a capsid enclosing at least one heterologous cargo molecule and a packing sequence. A VLP may further comprise at least one ribozyme enclosed by the capsid. The heterologous cargo molecule may comprise an oligonucleotide, or an oligoribonucleotide. A VLP may comprise one or more ribozymes, and a ribozyme may be flanked by the packing sequence and the oligoribonucleotide to form a nucleic acid construct. A VLP may comprise a plurality of the nucleic acid constructs. In a VLP comprising an oligoribonucleotide, the oligoribonucleotide may be a short RNA selected from siRNA, shRNA, sshRNA, lshRNA and miRNA. A VLP may comprise two or more ribozymes, wherein each ribozyme is selected to cut one end of the short RNA. Ribozymes may be selected for example from a Hammerhead ribozyme and a Hepatitis Delta V ribozyme. A Hammerhead ribozyme may be a Hammerhead ribozyme variant having a contiguous set of nucleotides complementary to at least 6 contiguous nucleotides of the oligoribonucleotide. Alternatively, the ribozyme may be a mutant Hepatitis Delta V ribozyme capable of cleaving its connection with the oligoribonucleotide at a rate at most about 50% the rate of a wild type Hepatitis Delta V ribozyme.

VLPs according to the present disclosure may comprise a capsid which comprises a wild type viral capsid which is resistant to hydrolysis catalyzed by a peptide bond hydrolase category EC 3.4, or a capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid (SEQ ID NO: 3). The capsid may comprise a wild type Enterobacteria phage MS2 capsid protein having the amino acid sequence of SEQ ID NO: 3.

VLPs according to the present disclosure may comprise a heterologous cargo molecule comprising a peptide or polypeptide. A VLP may further comprise an oligonucleotide linker coupling the heterologous cargo peptide or polypeptide molecule and the viral capsid. The oligonucleotide linker may be an oligoribonucleotide comprising a ribozyme sequence. Alternatively, the heterologous cargo molecule may comprise a bi-molecular cargo molecule comprising a bifunctional polynucleotide comprising a first aptamer sequence which specifically binds a bioactive small molecule having a molecular weight of about 1,500 Da or less and a second aptamer sequence for binding a packing sequence of the capsid. The VLP may further comprise the bioactive small molecule bound to the first aptameric sequence. The bioactive small molecule may comprise an herbicide or a pesticide, which may selected for example from atrazine, acetamipridphorate, profenofos, isocarbophos and omethoateas.

In another aspect, the present disclosure provides a nucleic acid construct comprising a nucleotide sequence that encodes a short RNA, a ribozyme and a packing sequence. The short RNA may be for example an siRNA or an shRNA. The nucleic acid construct may further comprise a linking nucleotide sequence of 4 to 100 nucleotides, wherein the linking nucleotide sequence is flanked by the packing sequence and by the short RNA sequence. The nucleic acid construct may further comprise a linking nucleotide sequence of 4 to 100 nucleotides, wherein the linking nucleotide sequence is flanked by the ribozyme and the short RNA sequence. The ribozyme sequence may be flanked by the short RNA and the packing sequence. The present disclosure also encompasses a vector comprising any such nucleic acid constructs, and host cells comprising such a vector, as well as host cell stably transformed with such a vector. Host cells may be a bacterial cell, such as but not limited to an *Escherichia coli* cell, a plant cell, a mammalian cell, an insect cell, a fungal cell or a yeast cell. A host cell may further be stably transfected with a second vector comprising a second nucleic acid sequence encoding a viral capsid which is resistant to hydrolysis catalyzed by a peptide bond hydrolase category EC 3.4. The second nucleic acid sequence may encode for example a viral protein encoding a viral capsid having at least 40% sequence identity with the amino acid sequence of wild type Enterobacteria phage MS2 capsid protein (SEQ ID NO: 3). A nucleic acid construct as described herein may also encode a wild type Enterobacteria phage MS2 capsid protein (SEQ ID NO: 3). The ribozyme in such a nucleic acid construct may be for example a Hammerhead ribozyme, .a Hammerhead ribozyme variant having a contiguous set of nucleotides complementary to at least 6 contiguous nucleotides of the short RNA, a Hepatitis Delta V ribozyme, or a mutant Hepatitis Delta V ribozyme capable of cleaving its connection with the short RNA at a rate at most 50% the rate of a wildtype Hepatitis Delta V ribozyme. The present disclosure also encompasses a plant or plant tissue transformed to contain a nucleic acid construct described herein, and seed or progeny of such a plant or plant tissue, wherein the seed or progeny comprises the nucleic acid construct.

In another aspect, the present disclosure provides a composition comprising: a) a plurality of VLPs each comprising a viral capsid enclosing at least one heterologous cargo molecule; and b) one or more cell lysis products present in an amount of less than 4 grams for every 100 grams of capsid present in the composition, wherein the cell lysis products are selected from proteins, polypeptides, peptides and any combination thereof. In the composition, the capsid is for example resistant to hydrolysis catalyzed by a peptide bond hydrolase category EC 3.4. The capsid may comprise a capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid (SEQ ID NO: 3) and is resistant to hydrolysis catalyzed by a peptide bond hydrolase category EC 3.4. The capsid may comprises a wild type Enterobacteria phage MS2 capsid protein (SEQ ID NO: 3). In the composition, the heterologous cargo molecule may comprise an oligonucleotide which may be an oligoribonucleotide. An oligoribonucleotide may be selected for example from siRNA, shRNA, sshRNA, lshRNA miRNA and mRNA. In the composition, each VLP may further comprise at least one ribozyme, wherein the ribozyme is flanked by the packing sequence and the oligoribonucleotide to form a nucleic acid construct, and each VLP may comprise a plurality of the nucleic acid constructs. In the VLPs of such a composition, the ribozyme may be for example a Hammerhead ribozyme, .a Hammerhead ribozyme variant having a contiguous set of nucleotides complementary to at least 6 contiguous nucleotides of the short RNA, a Hepatitis Delta V ribozyme, or a mutant Hepatitis Delta V ribozyme capable of cleaving its connection with the short RNA at a rate at most 50% the rate of a wildtype Hepatitis Delta V ribozyme. The VLPs in such a composition may further comprise a linking nucleotide sequence of 4 to 100 nucleotides, wherein the linking nucleotide sequence is flanked by the packing-coding sequence and by the short RNA-coding sequence, or a linking nucleotide sequence of 4 to 100 nucleotides, wherein the linking nucleotide sequence is flanked by the ribozyme and the short RNA-encoding sequence. The ribozyme sequence may be flanked by the short RNA and the packing sequence. The VLPs in such a composition may comprise a heterologous cargo molecule comprising a peptide or polypeptide. Such VLPs in a composition may further comprise an oligonucleotide linker coupling the heterologous cargo molecule and the viral capsid. The oligonucleotide linker may be an oligoribonucleotide comprising a ribozyme sequence. In such a composition, the cell lysis products may be present in an amount of less than 0.5 grams, less than 0.2 grams or less than 0.1 grams.

In another aspect, the present disclosure provides a method for isolating and purifying a target cargo molecule, the method comprising: (a) obtaining a whole cell lysate comprising a plurality of VLPs each comprising a capsid enclosing at least one target cargo molecule, wherein the capsids are resistant to hydrolysis catalyzed by a peptide bond hydrolase category EC 3.4; (b) subjecting the VLPs to hydrolysis using a peptide bond hydrolase category EC 3.4, for a time and under conditions sufficient for at least 60, at least 70, at least 80, or at least 90 of every 100 individual polypeptides present in the whole cell lysate but not enclosed by the capsids to be cleaved, while at least 60, at least 70, at least 80, or at least 90 of every 100 capsids present in the whole cell lysate before such hydrolysis remain intact following the hydrolysis. In the method, the capsids may each comprise a viral capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid protein (SEQ ID NO: 3). The capsids may each comprise a wild type Enterobacteria phage MS2 capsid protein (SEQ ID NO: 3). In the method, the heterologous cargo molecule may comprise an oligonucleotide which may be an oligoribonucleotide, or a peptide or a polypeptide. An oligoribonucleotide may be selected for example from siRNA, shRNA, sshRNA, lshRNA, miRNA and mRNA. In the method, each VLP may further comprise a ribozyme, wherein the ribozyme is flanked by the packing sequence and the oligoribonucleotide to form a nucleic acid construct. The method may further comprise purification of the capsids following hydrolysis. Purification may include at least one of a liquid-liquid extraction step, a crystallization step, a fractional precipitation step, and an ultra filtration step. The present disclosure also encompasses a composition produced by such a method.

In another aspect, the present disclosure provides a method for protecting a target molecule from hydrolysis in a whole cell lyste following intracellular production of the target molecule in a host cell, the method comprising: (a) selecting a viral capsid which is resistant to hydrolysis catalyzed by a peptide bond hydrolase category EC 3.4; (b) stably transfecting the host cell with a first vector comprising a nucleic acid sequence encoding a viral protein forming the viral capsid, and a second vector comprising a nucleic acid sequence comprising a ribozyme flanked by a packing sequence and an siRNA sequence; and (c) maintaining the cells for a time and under conditions sufficient for the transformed cells to express and assemble capsids encapsidating the ribozyme flanked by the packing sequence and the siRNA sequence. In the process, the capsids may each comprises a viral capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid protein (SEQ ID NO: 3).

In another aspect, the present disclosure provides a process for purifying VLPs enclosing at least one heterologous cargo molecule, the process comprising: (a) obtaining a cell lysate comprising a plurality of the VLPs; (b) contacting the cell lysate with a protease for a time and under conditions sufficient to hydrolyze cell lysis products other than the VLPs to form a hydrolysate; and (c) isolating the VLPs from the hydrolsyate. Step (c) may comprise (i) performing a first precipitation with ammonium sulfate followed by a first centrifugation to obtain a first precipitate and a first supernatant; and (ii) performing a second precipitation on the first supernatant with ammonium sulfate followed by a second centrifugation to obtain a second precipitate, wherein the second precipitate comprises at least about 70%, 80% or 90% by weight of the VLPs. Step (c) may comprise (i) performing a first precipitation with ethanol followed by a first centrifugation to obtain a first precipitate and a first supernatant; and (ii) performing a second precipitation on the first supernatant with ammonium sulfate followed by a second centrifugation to obtain a second precipitate, wherein the second precipitate comprises at least about 70%, 80% or 90% by weight of the VLPs. Step (c) may comprise ultra-centrifuging the hydrolysate to obtain a precipitate comprising at least about 70%, 80% or 90% by weight of the VLPs. In the process, the VLPs may each comprise a capsid which is resistant to hydrolysis catalyzed by a peptide bond hydrolase category EC 3.4., which can comprise a capsid protein having at least 15%, at least 16%, at least 21%, at least 40%, at least 41%, at least 45%, at least 52%, at least 53%, at least 56%, at least 59% or at least 86% sequence identity with the amino acid sequence of wild type Enterobacteria phage MS2 capsid (SEQ ID NO: 3). The VLPs may each comprise a wild type Enterobacteria phage MS2 capsid protein (SEQ ID NO: 3). In the process, step (b) can be performed for at least about 30 minutes at about 37° C. The process may further comprise, before step (b), contacting the cell lysate with at least one of a nuclease, an amylase and a lipase for at least about 30 minutes at about 37° C. In the process, the protease can be for example a peptide bond hydrolase category EC 3.4, which can be selected for example from Proteinase K, Protease from *Streptomyces griseus*, Protease from *Bacillus licheniformis*, pepsin and papain. In the process, the heterologous cargo molecule enclosed by the VLPs may comprise an oligonucleotide which may be an oligoribonucleotide, or a peptide or a polypeptide. An oligoribonucleotide may be selected for example from siRNA, shRNA, sshRNA, lshRNA, miRNA and mRNA. In the process, the VLPs may each further comprise a ribozyme as described herein, flanked by a packing sequence and the oligoribonucleotide to form a nucleic acid construct. The oligoribonucleotide and the packing sequence may be linked by a linker sequence of at least 1 to 100 nucleotides. The process may further comprise preparing the cell lyaste before step (a) by centrifuging cells following expression of the VLPs in the cells; resuspending the cells; lysing the cells and centrifuging the cell lysate to obtain a supernatant, wherein the supernatant is used as the cell lysate for step (a).

In another aspect, the present disclosure provides VLPs comprising a capsid enclosing at least one heterologous cargo molecule and a packing sequence wherein the capsid comprises a capsid protein which is a variant of wild type Enterobacteria phage MS2 capsid (SEQ ID NO: 3). The capsid protein may be one which has the amino acid sequence of wild type Enterobacteria phage MS2 capsid (SEQ ID NO: 3) except that the A residue at position 1 is deleted. The capsid protein may be one which has the amino acid sequence of wild type Enterobacteria phage MS2 capsid (SEQ ID NO:3) except that the A residue at position 1 is deleted and the S residue at position 2 is deleted. The capsid protein may be one which has the amino acid sequence of wild type Enterobacteria phage MS2 capsid (SEQ ID NO: 3) except that the A residue at position 1 is deleted, the S residue at position 2 is deleted and the N residue at position 3 is deleted. The capsid protein may be one which has the amino acid sequence of wild type Enterobacteria phage MS2 capsid (SEQ ID NO: 3) except that the Y reside at position 129 is deleted. The capsid protein may be one which has the amino acid sequence of wild type Enterobacteria phage MS2 capsid (SEQ ID NO:3) but having a single (1) amino acid deletion in the 112-117 segment. The capsid protein may be one which has the amino acid sequence of wild type Enterobacteria phage MS2 capsid (SEQ ID NO:3) but having a single (1) amino acid deletion in the 112-117 segment. The capsid protein may be one which has the amino acid sequence of wild type Enterobacteria phage MS2 capsid (SEQ ID NO:3) but having a 1-2 residue insertion in the 65-83 segment. The capsid protein may be one which has the amino acid sequence of wild type Enterobacteria phage MS2 capsid (SEQ ID NO:3) but having a 1-2 residue insertion in the 44-55 segment. The capsid protein may be one which has the amino acid sequence of wild type Enterobacteria phage MS2 capsid (SEQ ID NO:3) but having a single (1) residue insertion in the 33-43 segment. The capsid protein may be one which has the amino acid sequence of wild type Enterobacteria phage MS2 capsid (SEQ ID NO:3) but having a 1-2 residue insertion in the 24-30 segment. The capsid protein may be one which has the amino acid sequence of wild type Enterobacteria phage MS2 capsid (SEQ ID NO:3) but having a single (1) residue insertion in the 10-18 segment. The capsid may comprise a capsid protein monomer sequence concatenated with a second capsid monomer sequence which assembles into a capsid which resistant to hydrolysis catalyzed by a peptide bond hydrolase category EC 3.4. The capsid may comprise a capsid protein monomer sequence whose C-terminus is extended with a 0-6 residue linker segment whose C-terminus is concatenated with a second capsid monomer sequence, all of which assembles into a capsid which resistant to hydrolysis catalyzed by a peptide bond hydrolase category EC 3.4. A linker segment may have a sequence such as, for example, $-(Gly)_x-$, wherein x=0-6. including -Gly-; -Gly-Gly-; and -Gly-Gly-Gly-. A linker segment may be a Gly-Ser linker selected from -Gly-Gly-Ser-Gly-Gly-, -Gly-Gly-Ser and -Gly-Ser-Gly-. The capsid may comprise the capsid protein concatenated with a third capsid monomer sequence which assembles into a capsid which resistant to hydrolysis catalyzed by a peptide bond hydrolase category EC 3.4. The capsid may comprise a capsid protein wherein the C-terminus is extended with a 0-6 residue linker segment whose C-terminus s concatenated with a third capsid monomer sequence, all of which assembles into a capsid which resistant to hydrolysis catalyzed by a peptide bond hydrolase category EC 3.4. The capsid may comprise a capsid protein wherein the capsid comprises a capsid protein in which one or both linker sequences is $-(Gly)_x-$, wherein x=0-6, including -Gly-; -Gly-Gly-; and -Gly-Gly-Gly-. A linker segment may be a Gly-Ser linker selected from -Gly-Gly-Ser-Gly-Gly-, -Gly-Gly-Ser and -Gly-Ser-Gly-.

Such a capsid protein assembles for example into a capsid which is resistant to hydrolysis catalyzed by a peptide bond hydrolase category EC 3.4. For example, the capsid may comprise a capsid protein in which one or both linker sequences is -(Gly)x-, x=1, which assembles into a capsid which is resistant to hydrolysis catalyzed by a peptide bond hydrolase category EC 3.4. The capsid may comprise a capsid protein in which one or both linker sequences is -(Gly)x-, x=2, which assembles into a capsid which is resistant to hydrolysis catalyzed by a peptide bond hydrolase category EC 3.4. The capsid may comprise a capsid protein in which one or both linker sequences is -(Gly)x-, x=3, which assembles into a capsid which is resistant to hydrolysis catalyzed by a peptide bond hydrolase category EC 3.4. The capsid may comprise one or more capsid protein sequences which are N-terminally truncated by 1-3 residues and a linker segment as described herein is lengthened by the number of residues deleted, and which is resistant to hydrolysis catalyzed by a peptide bond hydrolase category EC 3.4. The capsid may comprise one or more capsid protein sequences which is C-terminally truncated by 1 residue, and linker segments as described herein are lengthened by the one residue, wherein the capsid is resistant to hydrolysis catalyzed by a peptide bond hydrolase category EC 3.4. The capsid may comprise a first capsid protein sequence in a concatenated dimer which is C-terminally truncated by 1 residue and the linker segments lengthened by the one residue or wherein the first and/or second capsid protein sequence in a concatenated trimer is C-terminally truncated by 1 residues and which is resistant to hydrolysis catalyzed by a peptide bond hydrolase category EC 3.4. The capsid may comprise a capsid protein having N- and C-terminal truncations.

In another aspect, the present disclosure also provides methods for delivery of affordable mRNA to organisms using the VLPs as described herein. Accordingly, in such methods the cargo molecule is an mRNA. The methods overcome the need for 5' capped mRNA. The disclosed methods may be used for example to increase the expression of endogenous proteins or induce the expression of exogenous proteins, while using affordable RNA manufactured and purified using the compositions and purification methods also described herein. The increase in expression of endogenous protein(s) or induction of expression of exogenous proteins in a host may be accomplished in one of several alternative ways, using different mRNA cargo molecule(s), depending on the host.

For example, to increase expression of an endogenous protein, or induce expression of an exogenous protein (a protein of interest), in a bacterial host where 5' capped RNA is not required for translation, the mRNA of the protein of interest is introduced to the bacterial host as a cargo molecule in a VLP as described herein. The mRNA may be purified using the purification methods using VLPs as described herein. To increase expression in bacteria, the cargo mRNA molecule may further include RNA encoding a bacteriophage replicase, optionally also encoding replicase ancillary proteins, to increase the concentration of mRNA inside the bacterial host.

Alternatively, the mRNA delivery methods may be applied to a plant host where 5' capped RNA is required for translation. The mRNA of the protein of interest is introduced to a plant or a plant cell, wherein the mRNA is flanked by a viral 5' adaptor and its matching 3' cap independent translational enhancer ("3' CITE").

In still another example, the mRNA delivery methods maybe be applied to animals including mammals where 5' capped RNA is required for translation. The mRNA of the protein of interest is introduced to an animal or animal cell, such as for example a mammal or mammalian cell, wherein the mRNA of the protein of interest is flanked by viral or cellular internal ribosome entry sites (IRES) and a poly(A) signal. To further promote or increase expression in the animal or animal cell, the cargo mRNA molecule may further include RNA encoding a viral replicase, optionally also encoding replicase ancillary proteins, to increase the concentration of mRNA inside the animal or animal cell.

Alternatively, in any of the foregoing methods in which the host is also transfected with a viral replicase, and optionally its ancillary proteins, the mRNA encoding the replicase (and optionally the ancillary proteins), may be included in a VLP as a second cargo molecule distinct from the mRNA of the protein of interest, or may be included in a separate VLP which is then introduced to the host organism or cell in combination with a VLP containing only the mRNA of the protein of interest.

BRIEF DESCRIPTION OF THE DRAWINGS

FIG. 9 is a chromatograph of PCR products obtained from an MS2 sample following purification described for FIGS. 5 and 6, chromatographed in 1.5% agarose gel stained with Ethidium Bromide (1.2 kbp for primers F1201_1223-R1979_2001 in Lane 1, 800 bp for primers F1201_1223-R1979_2001 in Lane 2, and 304 bp for primers F1401_1426-R1680_1705 in Lane 3), consistent with the presence of an intact MS2 bacteriophage genome.

FIG. 10 is a chromatograph of PCR products from PCR interrogation of an MS2 sample for presence or absence of a section of the MS2 capsid following purification, chromatographed in 2% agarose gel stained with Ethidium Bromide (304 bp in Lane 1; the leftmost Lane corresponds to 1 kb plus ladder from Life Technologies), consistent with an intact MS2 capsid gene.

DETAILED DESCRIPTION OF THE INVENTION

Figure 1:
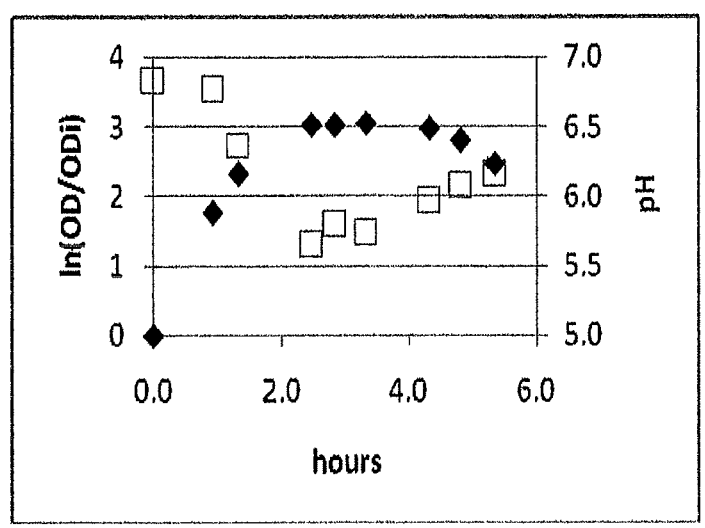
FIG. 1 is a plot of Optical Density (OD; filled diamonds) and pH (open squares) over time, showing propagation of wild type MS2 bacteriophage (ATCC No. 15597-B1, from American Type Culture Collection, Rockville, Md.) in *E. coli* host (ATCC No. 15669).

Section headings as used in this section and the entire disclosure herein are not intended to be limiting. All patents and publications cited herein are herein incorporated by reference in their entirety.

A. Definitions

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The use of "or" means "and/or" unless stated otherwise. Furthermore, the use of the term "including", as well as other forms, such as "includes" and "included", is not limiting.

Unless otherwise defined herein, scientific and technical terms used in connection with the present disclosure shall have the meanings that are commonly understood by those of ordinary skill in the art. For example, any nomenclatures used in connection with, and techniques of, animal and cellular anatomy, cell and tissue culture, biochemistry, molecular biology, immunology, and microbiology described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

A wide variety of conventional techniques and tools in chemistry, biochemistry, molecular biology, and immunology are employed and available for practicing the methods and compositions described herein, are within the capabilities of a person of ordinary skill in the art and well described in the literature. Such techniques and tools include those for generating and purifying VLPs including those with a wild type or a recombinant capsid together with the cargo molecule(s), and for transforming host organisms and expressing recombinant proteins and nucleic acids as described herein. See, e.g., MOLECULAR CLONING, A LABORATORY MANUAL 2$^{nd}$ ed. 1989 (Sambrook et al., Cold Spring Harbor Laboratory Press); and CURRENT PROTOCOLS IN MOLECULAR BIOLOGY (Eds. Ausubel et al., Greene Publ. Assoc., Wiley-Interscience, NY) 1995. The disclosures in each of these are herein incorporated by reference.

As used herein, the term "cargo molecule" refers to an oligonucleotide, polypeptide or peptide molecule, which is or may be enclosed by a capsid.

An oligonucleotide may be an oligodeoxyribonucleotide (DNA) or a oligoribonucleotide (RNA), and encompasses RNA molecules such as, but not limited to, siRNA, shRNA, sshRNA, miRNA and mRNA. Certain RNA molecules may also be referred to as "active RNAs" a term meant to denote any RNA with a functional activity, including RNAi, ribozyme or packing activities.

As used herein, the term "peptide" refers to a polymeric molecule which minimally includes at least two amino acid monomers linked by peptide bond, and preferably has at least about 10, and more preferably at least about 20 amino acid monomers, and no more than about 60 amino acid monomers, preferably no more than about 50 amino acid monomers linked by peptide bonds. For example, the term encompasses polymers having about 10, about 20, about 30, about 40, about 50, or about 60 amino acid residues.

As used herein, the term "polypeptide" refers to a polymeric molecule including at least one chain of amino acid monomers linked by peptide bonds, wherein the chain includes at least about 70 amino acid residues, preferably at least about 80, more preferably at least about 90, and still more preferably at least about 100 amino acid residues. As used herein the term encompasses proteins, which may include one or more linked polypeptide chains, which may or may not be further bound to cofactors or other proteins. The term "protein" as used herein is used interchangeably with the term "polypeptide."

As used herein, the term "variant" with reference to a molecule is a sequence that is substantially similar to the sequence of a native or wild type molecule. With respect to nucleotide sequences, variants include those sequences that may vary as to one or more bases, but because of the degeneracy of the genetic code, still encode the identical amino acid sequence of the native protein. Variants include naturally occurring alleles, and nucleotide sequences which are engineered using well-known techniques in molecular biology, such as for example site-directed mutagenesis, and which encode the native protein, as well as those that encode a polypeptide having amino acid substitutions. Generally, nucleotide sequence variants of the invention have at least 40%, at least 50%, at least 60%, at least 70% or at least 80% sequence identity to the native (endogenous) nucleotide sequence. The present disclosure also encompasses nucleotide sequence variants having at least about 85% sequence identity, at least about 90% sequence identity, at least about 85%, 86%, 87%, 88%, 89%, 90% 91%, 92%, 93%, 94%, 95%, 96%, 97%, 98%, 99%.

Sequence identity of amino acid sequences or nucleotide sequences, within defined regions of the molecule or across the full-length sequence, can be readily determined using conventional tools and methods known in the art and as described herein. For example, the degree of sequence identity of two amino acid sequences, or two nucleotide sequences, is readily determined using alignment tools such as the NCBI Basic Local Alignment Search Tool (BLAST) (Altschul et al., 1990), which are readily available from multiple online sources. Algorithms for optimal sequence alignment are well known and described in the art, including for example in Smith and Waterman, Adv. Appl. Math. 2:482 (1981); Pearson and Lipman Proc. Natl. Acad. Sci. (U.S.A.) 85: 2444 (1988). Algorithms for sequence analysis are also readily available in programs such as blastp, blastn, blastx, tblastn and tblastx. For the purposes of the present disclosure, two nucleotide sequences may be also considered "substantially identical" when they hybridize to each other under stringent conditions. Stringent conditions include high hybridization temperature and low salt hybridization buffers which permit hybridization only between nucleic acid sequences that are highly similar. Stringent conditions are sequence-dependent and will be different in different circumstance, but typically include a temperature at least about 60°, which is about 10° C. to about 15° C. lower than the thermal melting point (Tm) for the specific sequence at a defined ionic strength and pH. Salt concentration is typically about 0.02 molar at pH 7.

As used herein with respect to a given nucleotide sequence, the term "conservative variant" refers to a nucleotide sequence that encodes an identical or essentially identical amino acid sequence as that of a reference sequence. Due to the degeneracy of the genetic code, whereby almost always more than one codon may code for each amino acid, nucleotide sequences encoding very closely related proteins may not share a high level of sequence identity. Moreover, different organisms have preferred codons for many amino acids, and different organisms or even different strains of the same organism, e.g., *E. coli* strains, can have different preferred codons for the same amino acid. Thus, a first nucleotide acid sequence which encodes essentially the same polypeptide as a second nucleotide acid sequence is considered substantially identical to the second nucleotide sequence, even if they do not share a minimum percentage sequence identity, or would not hybridize to one another under stringent conditions. Additionally, it should be understood that with the limited exception of ATG, which is usually the sole codon for methionine, any sequence can be modified to yield a functionally identical molecule by standard techniques, and such modifications are encompassed by the present disclosure. As described herein below, the present disclosure specifically contemplates protein variants of a native protein, which have amino acid sequences having at least 15%, at least 16%, at least 21%, at least 40%, at least 41%, at least 52%, at least 53%, at least 56%, at least 59% or at least 86% sequence identity to a native nucleotide sequence.

The degree of sequence identity between two amino acid sequences may be determined using the BLASTp algorithm of Karlin and Altschul (Proc. Natl. Acad. Sci. USA 87:2264-2268, 1993). The percentage of sequence identity is determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which an identical amino acid occurs in both sequences to yield the number of matched positions, dividing the number of matched positions by the total number of positions in the window of comparison and multiplying the result by 100 to yield the percentage of sequence identity.

One of skill will recognize that polypeptides may be "substantially similar" in that an amino acid may be substituted with a similar amino acid residue without affecting the function of the mature protein. Polypeptide sequences which are "substantially similar" share sequences as noted above except that residue positions, which are not identical, may have conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups include' valine-leucine-isoleucine, phenylalanine-tyrosine, lysine-arginine, alanine-valine, and asparagine-glutamine.

A nucleic acid encoding a peptide, polypeptide or protein may be obtained by screening selected cDNA or genomic libraries using a deduced amino acid sequence for a given protein. Conventional procedures using primer extension procedures, as described for example in Sambrook et al., can be used to detect precursors and processing intermediates.

B. VLPs Composed of a Capsid Enclosing a Cargo Molecule

The methods and compositions described herein are the result in part of the appreciation that certain viral capsids can be prepared and/or used in novel manufacturing and purification methods to improve commercialization procedures for nucleic acids. The methods described herein use recombinant viral capsids which are resistant to readily available hydrolases, to enclose heterologous cargo molecules such as nucleic acids, peptides, or polypeptides including proteins.

The capsid may be a wild type capsid or a mutant capsid derived from a wild type capsid, provided that the capsid exhibits resistance to hydrolysis catalyzed by at least one hydrolase acting on peptide bonds when the capsids are contacted with the hydrolase. As used interchangeably herein, the phrases "resistance to hydrolysis" and "hydrolase resistant" refer to any capsid which, when present in a whole cell lysate also containing polypeptides which are cell lysis products and not enclosed or incorporated in the capsids, and subjected to hydrolysis using a peptide bond hydrolase category EC 3.4 for a time and under conditions sufficient for at least 60, at least 70, at least 80, or at least 90 of every 100 individual polypeptides present in the lysate (which are cell lysis products and not enclosed in the capsids) to be cleaved (i.e. at least 60%, at least 70%, at least 80%, or at least 90% of all individual unenclosed polypeptides are cleaved), yet at least 60, at least 70, at least 80, or at least 90 of every 100 capsids present before such hydrolysis remain intact following the hydrolysis. Hydrolysis may be conducted for a period of time and under conditions sufficient for the average molecular weight of cell proteins remaining from the cell line following hydrolysis is less than about two thirds, less than about one half, less than about one third, less than about one fourth, or less than about one fifth, of the average molecular weight of the cell proteins before the hydrolysis is conducted. Methods may further comprise purifying the intact capsid remaining after hydrolysis, and measuring the weight of capsids and the weight of total dry cell matter before and after hydrolysis and purification, wherein the weight of capsids divided by the weight of total dry cell matter after hydrolysis and purification is at least twice the weight of capsids divided by the weight of total dry cell matter measured before the hydrolysis and purification. The weight of capsids divided by the weight of total dry cell matter after hydrolysis and purification may be at least 10 times more than, preferably 100 times more than, more preferably 1,000 times more than, and most preferably 10,000 times more than the weight of capsids divided by the weight of total dry cell matter measured before such hydrolysis and purification.

Hydrolases are enzymes that catalyze hydrolysis reactions classified under the identity number E.C. 3 by the Enzyme Commission. For example, enzymes that catalyze hydrolysis of ester bonds have identity numbers starting with E.C. 3.1. Enzymes that catalyze hydrolysis of glycosidic bonds have identity numbers starting with E.C. 3.2. Enzymes that catalyze hydrolysis of peptide bonds have identity numbers starting with E.C. 3.4. Proteases, which are enzymes that catalyze hydrolysis of proteins, are classified using identity numbers starting with E.C. 3.4, including but not limited to Proteinase K and subtilisin. For example, Proteinase K has identity number E.C. 3.4.21.64. The present disclosure encompasses VLPs which are resistant, in non-limiting example, Proteinase K, Protease from *Streptomyces griseus*, Protease from *Bacillus licheniformis*, pepsin and papain, and methods and processes of using such VLPs.

The Nomenclature Committee of the International Union of Biochemistry and Molecular Biology (IUBMB) also recommends naming and classification of enzymes by the reactions they catalyze. Their complete recommendations are freely and widely available, and for example can be accessed online at enzyme.expasy.org and, chem.qmul.ac.uk/iubmb/enzyme/, among others. The IUBMB developed shorthand for describing what sites each enzyme is active against. Enzymes that indiscriminately cut are referred to as broadly specific. Some enzymes have more extensive binding requirements so the description can become more complicated. For an enzyme that catalyzes a very specific reaction, for example an enzyme that processes prothrombin to active thrombin, then that activity is the basis of the cleavage description. In certain instances the precise activity of an enzyme may not be clear, and in such cases, cleavage results against standard test proteins like B-chain insulin are reported.

Use of simple and effective purification processes using the capsids is enabled by the choice of certain wild type capsids, or modifications to the amino acid sequence of proteins comprising the wild type capsids, such that the capsid exhibits resistance to hydrolysis catalyzed by at least one hydrolase acting on peptide bonds as described herein above. Such wild type capsids, such as the wild type MS2 capsid, can be used in a purification process in which certain inexpensive enzymes such as Proteinase K or subtilisin are used for proteolysis. A non-limiting example is the Enterobacteria phage MS2 wild type genome (SEQ ID NO: 1); MS2 wild type capsid protein DNA sequence (SEQ ID NO: 2); and MS2 wild type capsid protein amino acid sequence (SEQ ID NO: 3).

Surprisingly, the unmodified, wild type MS2 capsid though lacking an envelope is resistant to a variety of category EC 3.4 hydrolases, including but not limited to Proteinase K and subtilisin, such that a highly purified composition of the capsid, which may contain a cargo molecule, can be prepared from a whole cell lysate. Accordingly, the present disclosure provides VLPs comprising viral capsids comprising the wild type MS2 capsid protein, and/or capsid proteins sharing homology with wild type MS2 capsid proteins, which viral capsids encapsidate the cargo molecule. The cargo molecule may comprise one or more heterologous nucleic acids, peptides, polypeptides or proteins. These VLPs can then be isolated and purified from a whole cell lysate after a hydrolysis step using a category E.C. 3.4 hydrolase, to produce a composition of VLPs of high purity, for example at least 60%, at least 70%, a least 80%, or at least 85% by weight VLPs. Compositions having a purity of at least 90%, 91%, 92%, 93%, 94%, 95%, 96%, 97%, and 98% by weight of VLPs are expressly contemplated.

The present disclosure encompasses a composition comprising: a) a plurality of VLPs each comprising a wild type viral capsid and at least one target heterologous cargo molecule enclosed in the wild type viral capsid; and b) one or more cell lysis products present in an amount of less than 40 grams, less than 30 grams, less than 20 grams, less than 15 grams, less than 10 grams, and preferably less than 9, 8, 7, 6, 5, 4, 3, more preferably less than 2 grams, and still more preferably less than 1 gram, for every 100 grams of capsid present in the composition, wherein the cell lysis products are selected from proteins, polypeptides, peptides and any combination thereof. Subsequently the cargo molecules can be readily harvested from the capsids. Accordingly, such compositions are highly desirable for all applications where high purity and/or high production efficiency is required.

Hydrolase resistant capsids as described herein may be used to enclose different types of cargo molecules to form a VLP. The cargo molecule can be but is not limited to any one or more oligonucleotide or oligoribonucleotide (DNA, RNA, LNA, PNA, siRNA, shRNA, sshRNA, lshRNA, miRNA or mRNA, or any oligonucleotide comprising any type of non-naturally occurring nucleic acid), any peptide, polypeptide or protein. A cargo molecule which is an oligonucleotide or oligoribonucleotide may be enclosed in a capsid with or without the use of a linker A capsid can be triggered for example to self-assemble from capsid protein in the presence of nucleotide cargo, such as an oligoribonucleotide. In non-limiting example, a capsid as described herein may enclose a target heterologous RNA strand, such as for example a target heterologous RNA strand containing a total of between 1,800 and 2,248 ribonucleotides, including the 19-mer packing sequence from Enterobacteria phage MS2, such RNA strand transcribed from a plasmid separate from a plasmid coding for the capsid proteins, as described by Wei, Y., et al., (2008) J. Clin. Microbiol. 46:1734-1740.

RNA interference (RNAi) is a phenomenon mediated by short RNA molecules such as siRNA molecules, which can be used for selective suppression of a target gene of interest, and has multiple applications in biotechnology and medicine. For example, short RNA molecules can be employed to target a specific gene of interest in an organism to obtain a desirable phenotype. Short RNA molecules, including siRNA, are however easily degraded by ubiquitous enzymes called RNAses. Capsids, such as those described herein, protect encapsidated RNA from enzymatic degradation. A capsid as described herein may however enclose an RNA strand containing one or more ribozymes, either self-cleaving ribozymes (cis-acting), or in certain cases capable of cleaving bonds in other RNA (trans-acting). One or more ribozymes may be included for example to specifically cut RNA sequence(s) to produce a specifically tailored RNA molecule, such as for example but not limited to an siRNA molecule. For example, variants of Hammerhead and Hepatitis Delta Virus ribozymes are known and can be used to cut long RNA sequences. The present disclosure describes novel VLPs comprising a capsid encapsidating one or more ribozymes attached to a packing sequences as described above (i.e., RNA sequences with strong affinity to the interior wall of a capsid), and the ribozymes used to cut short RNA sequences from packing sequences attached to the ribozymes.

The present disclosure thus also encompasses the novel use of ribozymes to isolate short or small RNA sequences such as siRNA, shRNA, sshRNA, lshNA and miRNA sequences from the packing sequence(s) used to encapsidate them. It should be understood that, unless expressly indicated otherwise, the term short RNA encompasses short single stranded and short hairpin (stem loop) RNA sequences having a double stranded stem and a single-stranded loop or hairpin. A short RNA is any RNA single strand having no more than 30 nucleotides, preferably no more than 25 nucleotides, and more preferably no more than 22 nucleotides; or a hairpin RNA having a stem of no more than 30 nucleotides base pairs, preferably no more than 25 nucleotide base pairs, and more preferably no more than 22 nucleotide base pairs in the stem.

A challenge in using a ribozyme which is highly active to isolate such short RNA sequences from packing sequences, is that the ribozyme may works so fast as to liberate the short RNA from the packing sequence before encapsidation of the RNA is achieved. Additionally, it has been discovered that the three dimensional structures of short RNA such as an siRNA, or the hairpin packing sequences, can interfere with the proper functioning of the ribozyme. These problems can be overcome by 1) using ribozyme mutants which demonstrate a slower rate of activity, to avoid liberation of the short RNA from the packing sequence before encapsidation of the short RNA is achieved, and/or 2) increasing the number of nucleotides in the ribozyme that form Watson-Crick pairs with the short RNA. Additionally, trans-acting ribozymes can be used advantageously to increase the percentage of RNA encapsidated into VLPs as short RNA, if the short RNA sequence(s) are flanked not by complete ribozymes but rather shorter sequences that are targets of trans-acting ribozymes, also encapsidated into the same VLP.

One or more short RNA sequences can also be encapsidated into a viral capsid, either wild type or genetically modified, which has been modified to insert an external peptide tag, to deliver a protein or drug molecule to a specific class of cell. Wild type capsids may also be genetically modified to insert external peptide sequences acting as ligands for certain surface protein cell receptors can be advantageously used to encapsidate short RNA sequences aimed at inducing RNAi in specific target cells. Such compositions are much simpler, less expensive and more reliably manufactured than current alternatives for short RNA delivery.

Non-limiting examples of useful VLPs which can be prepared include a capsid enclosing an RNA strand comprising:

at least one packing sequence and from 1 to 100 identical or different siRNAs flanked by one single stranded (non-hybridyzing) RNA spacer, where every single stranded RNA spacer has between 4 and 40 nucleotides;

(ii) one (1) ribozyme and one single stranded (non-hybridizing) RNA spacer per siRNA, where every single stranded RNA spacer has between 4 and 40 nucleotides;

(iii) two (2) ribozymes per siRNA;

(iv) one (1) T7 start site, one (1) ribozyme, one (1) packing site and one (1) transcription termination site; or (v) one (1) T7 start site, one (1) packing site, and one (1) transcription termination site.

(vi) four (4) ribozymes per siRNA.

In VLPs which include one or more ribozymes, the disclosure further contemplates VLPs containing the resulting products after the ribozymes have cut the RNA.

The present disclosure also encompasses the novel use of capsids to encompass long RNA sequences such as mRNAs and the use of ribozymes to separate the mRNA sequences from the packing sequence(s) used to encapsidate them. It should be understood that, unless expressly indicated otherwise, the term long RNA encompasses long single stranded RNA sequences which may have double stranded stem and a single-stranded loops or hairpins arrayed throughout. A long RNA is any single stranded RNA having more than 30 nucleotides, preferably more than 40 nucleotides, and more preferably more than 50 nucleotides; and more preferably more than 100 nucleotide base pairs. In the most preferable embodiment the mRNA will include the necessary translational and protective signals required to produce a protein which it encodes within the host cell to which it is targeted. A capsid as described herein may enclose an mRNA-terminally tagged with a capsid packing sequence and may optionally include a ribozyme designed to cleave the mRNA from the packing sequence.

VLPs as described herein may alternatively enclose at least one target peptide, polypeptide or protein. When the target heterologous cargo molecule is a peptide, polypeptide or protein, an oligonucleotide linker can be used to couple the target heterologous cargo molecule and the viral capsid. A cargo molecule which is a peptide, polypeptide or protein, preferably is packaged in a capsid using a linker. The packaging process is promoted by the linker, consisting of a short RNA aptamer sequence, which forms a link between the capsid protein and a peptide tag fused to the target cargo molecule. (See Fiedler, J. et al., RNA-Directed Packaging of Enzymes within Virus-like Particles, Angew. Chem. hit. Ed. 49: 9648-9651 (2010)). The oligonucleotide linker may consist of DNA, RNA, LNA, PNA, and the like. The linker is for example a 50- to 100-mer having a short sequence, for example about 20 nt long, at a first end with binding specificity for the inside of the capsid capsid, and another sequence, for example about 70 nt long, at the second, opposite end which has a binding specificity for the cargo peptide, polypeptide or protein. Additionally, a slow ribozyme may be incorporated into a linker consisting of RNA. For example, a slow ribozyme can be incorporated between the packing sequence (binding to the capsid protein) and the aptamer (binding to the tag of target protein). Upon activation, the ribozyme will separate the capsid protein from the target protein. Alternatively, a capsid as described herein may enclose at least one target protein N-terminally tagged with a peptide able to non-covalently bind to an aptamer- and capsid packing sequence-containing RNA strand, for example an N-terminal tag and aptamer- and packing sequence-containing RNA strand as described by Fiedler, J. et al. (2010).

A cargo molecule can be a bi-molecular cargo molecule, and capsids described herein may also encapsidate a bi-molecular cargo molecule, which may or may not include one or more ribozymes. A bi-molecular cargo molecule may comprise an aptamer linked to a bifunctional polynucleotide. The aptamer may have a sequence specifically selected using SELEX to exhibit specific binding to a bioactive small molecule, i.e., a molecule having a low molecular weight, preferably lower than 1,500 Da. The bifunctional polynucleotide has both a first aptameric activity for binding the low-molecular weight bioactive cargo molecule, and a second aptameric activity for binding a packing sequence of a capsid. The bifunctional polynucleotide linked to the bioactive cargo molecule forms the bi-molecular cargo molecule which can then be linked to the capsid. Such a cargo molecule can be used to bind the bioactive small molecule, and thus load the VLP with the small molecule. The present disclosure thus also encompasses a VLP comprising a capsid linked to such a synthetic bi-molecular cargo molecule. Examples of low molecular weight bioactives which can be loaded into a VLP by binding to an RNA aptamer include: atrazine (herbicide), acetamipridphorate, profenofos, isocarbophos and omethoateas (insecticides), as described by Sett et al. (2012) Open Journal of Applied Biosensor, 1:p. 9-19.

Examples of low molecular weight bioactives which can be loaded into a VLP by binding to an RNA aptamer include herbicides such as 2,4-D (2,4-Dichlorophenoxyacetic acid), December ((3,6-dichloro-2-methoxybenzoic acid), Paraquat (N,N'-dimethyl-4,4'-bipyridinium dichloride), Oryzalin (4-(dipropylamino)-3,5-dinitrobenzenesulfonamide), DCMU (3-(3,4-dichlorophenyl)-1,1-dimethylurea), Trifluralin (2,6-Dinitro-N,N-dipropyl-4-(trifluoromethyDaniline), Imazapic (-methyl-2-[4-methyl-5-oxo-4-(propan-2-yl)-4,5-dihydro-1H-imidazol-2-yl]pyridine-3-carboxylic acid), Aminopyralid (4-amino-3,6-dichloropyridine-2-carboxylic acid), Clopyralid (3,6-dichloro-2-pyridinecarboxylic acid), Metolachlor ((RS)-2-Chloro-N-(2-ethyl-6-methyl-phenyl)-N-(1-methoxypropan-2-yl)acetamide), Pendimethalin (3,4-Dimethyl-2,6-dinitro-N-pentan-3-yl-aniline), Picloram (4-Amino-3,5,6-trichloro-2-pyridinecarboxylic acid), Propanil (N-(3,4-Dichlorophenyl)propanamide), Triclopyr ([(3, 5,6-Trichloro-2-pyridinyl)oxy]acetic acid), and Atrazine (2-chloro-4-(ethylamino)-6-(isopropylamino)-s-triazine), among other listed for example by Roberts et al. (1998) Metabolic Pathways of Agrochemicals: Part 1: Herbicides and Plant Growth Regulators. Published by Royal Society of Chemistry (Great Britain) ISBN 978-1-84755-138-2. For example, an RNA aptamer binding Atrazine was described by Sinha et al. (2010) Nature Chemical Biology, 6:p. 464-470.

RNA aptamers can also be used to bind insecticides such as, Propargite (2-(4-tert-butylphenoxy)cyclohexyl prop-2-yne-1-sulfonate), Chlorpyrifos (O,O-diethyl O-3,5,6-trichloropyridin-2-yl phosphorothioate), Cypermethrin, Phosmet (2-Dimethoxyphosphinothioylthiomethy)isoindoline-1,3-dione), Permethrin (3-Phenoxybenzyl (1RS)-cis, trans-3-(2,2-dichlorovinyl)-2,2-dimethylcyclopropanecarboxylate), Diazinon (O,O-Diethyl O[4-methyl-6-(propan-2-yl)pyrimidin-2-yl] phosphorothioate), Methylparathion (O,O-Dimethyl O-(4-nitrophenyl) phosphorothioate), and Acetamiprid (N-[(6-chloro-3-pyridyl)methyl]-Nt-cyano-N-methyl-acetamidine), and fungicides such as Chlorothalonil (2,4,5,6-tetrachloroisophthalonitrile), Captan ((3aR,7aS)-2-[(trichloromethyl)sulfanyl]-3a,4,7,7a-tetrahydro-1H-isoindole-1,3(2H)-dione), Boscalid (2-chloro-N-(4'-chlorobiphenyl-2-yl)nicotinamide), Iprodione (3-(3,5-dichlorophenyl)-N-isopropyl-2,4-dioxoimidazolidine-1-carboxamide), Azoxystrobin (Methyl (2E)-2-(2-{[6-(2-cyanophenoxy)pyrimidin-4-yl]oxy}phenyl)-3-methoxyacrylate), Pyraclostrobin, (methyl 2-[1-(4-chlorophenyl)pyrazol-3-yloxymethyl]-N-methoxycarbanilate), Cyprodinil (4-cyclopropyl-6-methyl-N-phenylpyrimidin-2-amine), among other listed for example by Roberts et al. (1999) Metabolic Pathways of Agrochemicals: Part 2: Insecticides and Fungicides. Published by Royal Society of Chemistry (Great Britain) ISBN 978-1-84755-137-5. For example, aptamers have been described to bind acetamiprid, phorate, profenofos, isocarbophos and omethoate, as exemplified by Sett et al. (2012) Open Journal of Applied Biosensor, 1:p.

9-19 using DNA aptamers built in a similar manner as RNA aptamers are built using SELEX.

These herbicides, insecticides or fungicides are bioactive small molecules, i.e., molecules having a low molecular weight, preferably lower than 1,500 Da. Due to their small size they can permeate capsids forming VLPs of the current disclosure, as exemplified by Wu et al. (2005) Delivery of antisense oligonucleotides to leukemia cells by RNA bacteriophage capsids, Nanomedicine: Nanotechnology, Biology and Medicine, 1:p. 67-76. These small bioactive molecules are added to VLPs of the current disclosure which encapsidate aptamers designed using SELEX to bind the small bioactive molecules, after such VLPs have been formed, either before or after purification. The addition of these small bioactive molecules is done, for example by adding them to a solution of the VLPs and incubation, for example at room temperature for a time between 30 minutes and 10 hours. These small bioactive molecules enter the VLPs by diffusion through the pores at the particle symmetry axes and are retained inside due to their binding to the enclosed aptamers. Suitable solvents used for loading the small bioactive molecules into the VLPs range from polar such as water and water-ethanol blends to non-polar such as, for example, isooctane, toluene, dichloromethane, or chloroform. Using non-polar solvents for the dissolution of VLPs is done, for example, as described by Johnson et al. (2006), Solubilization and stabilization of bacteriophage MS2 in organic solvents, Biotechnology and bioengineering, 2007. 97(2): p. 224-34, with the help of surfactants like Aerosol OT. Use of non-polar solvents for loading small bioactive molecules is preferred since their solubility in polar solvents is, in most cases, poor.

VLPs encapsidating both siRNA and small bioactive molecules are preferred in applications where a synergistic effect is achieved between the two bioactive ingredients, for example in those cases where the targeted plant, insect or fungus is resistant to the small bioactive molecule. In such cases, the siRNA is designed to target the biologic pathway that confers the plant, insect or fungus resistance to the small bioactive molecule, as exemplified by Sammons et al., Polynucleotide molecules for gene regulation in plants, US 2011/0296556.

Alternatively, the bi-functional polynucleotide may encode at least one siRNA, shRNA, sshRNA, lshRNA miRNA or mRNA, and the cargo molecule can be a small (low molecular weight) protein or peptide. Accordingly, a bi-molecular cargo molecule can be capable of binding a low molecular bioactive protein or peptide. Such a bi-molecular cargo molecule may comprise a biologically active protein or peptide, coupled to a polynucleotide encoding at least one siRNA or shRNA or sshRNA or lshRNA or miRNA or mRNA, and having a first aptameric activity for binding the bioactive protein or peptide cargo molecule and a second aptameric activity for binding a packing sequence of a capsid. The polynucleotide is linked to the protein or peptide cargo molecule and is capable of linking to packing sequence of a capsid.

A bifunctional polynucleotide as described above may optionally include one or more ribozyme sequences. A VLP including a bi-molecular cargo molecule including a bifunctional polynucleotide as described above may optionally include one or more ribozymes. The present disclosure also encompasses a VLP comprising a capsid and reaction products of the bi-molecular cargo molecule after at least one ribozyme has reacted with bimolecular cargo molecule to cut the cargo molecule into constituent parts including the aptamer.

VLPs as described herein may be assembled by any available method(s) which produces a VLP with an assembled, hydrolase resistant capsid encapsidating one or more cargo molecule(s), and optionally any linker, packing sequence, one or more ribozymes, or tags. For example, capsids and cargo molecules may be co-expressed in any expression system. Recombinant DNA encoding one or more capsid proteins, one or more cargo molecule(s), and optionally any linker, packing sequence, ribozyme(s) or tags can be readily introduced into the host cells, e.g., bacterial cells, plant cells, yeast cells, fungal cells, and animal cells (including insect and mammalian) by transfection with one or more expression vectors by any procedure useful for introducing such a vector into a particular cell, and stably transfecting the cell to yield a cell which expresses the recombinant sequence(s).

The host cell is preferably of eukaryotic origin, e.g., plant, mammalian, insect, yeast or fungal sources, but non-eukaryotic host cells may also be used. Suitable expression systems include but are not limited to microorganisms such as bacteria (e.g., *E. coli*,) transformed with recombinant bacteriophage DNA, plasmid DNA or cosmid DNA expression vectors containing the coding sequences for the VLP elements. In non-limiting example, for VLPs using the MS2 capsid protein, expression in *E. coli* is a suitable expression system.

The present disclosure expressly contemplates plant cells which have been transformed using a nucleic acid construct as described herein, and which expresses a capsid protein, cargo molecule and a and optionally any linker, packing sequence, one or more ribozymes, or tags. Means for transforming cells including plant cells and preparing transgenic cells are well known in the art. Vectors, plasmids, cosmids, YACs (yeast artificial chromosomes) and DNA segments can be used to transform cells and will as generally recognized include promoters, enhancers, and/or polylinkers. Transgenic cells specifically contemplated include transgenic plant cells including but not limited to cells obtained from corn, soybean, wheat, vegetables, grains, legumes, fruit trees, and so on, or any plant which would benefit from introduction of a VLP as described herein. Also contemplated are plants, plant tissue obtained from cells transformed as described herein, and the seed or progeny of the plant or plant tissue.

Expression of assembled VLPs can be obtained for example by constructing at least one expression vector including sequences encoding all elements of the VLP. Sometimes two vectors are used, a first vector which includes a sequence encoding the cargo molecule(s) and optionally any linker, packing sequence, one or more ribozymes, or tags; and a second vector which includes a sequence encoding the capsid protein. In an exemplary process for generating exemplary VLPs, two vectors may be co-expressed in the host cell for generation of the VLP, as further detailed in the Examples. Methods and tools for constructing such expression vectors containing the coding sequences and transcriptional and translational control sequences are well known in the art. Vector(s) once constructed are transferred to the host cells also using techniques well known in the art, and the cells then maintained under culture conditions for a time sufficient for expression and assembling of the VLPs to occur, all using conventional techniques. The present disclosure thus encompasses host cells containing any such vectors, and cells which have been transformed by such vectors, as well as cells containing the VLPs.

When the VLPs have been expressed and assembled in the host cells, they may be isolated and purified using any method known in the art for virus purification. For example, the cells can be lysed using conventional cell lysis techniques and agents, and the cell lysate subjected to hydrolysis using at least one peptide bond hydrolase category E.C. 3.4 such as but not limited to Proteinase K or subtilisin. Intact capsids remaining in the cell lysate following hydrolysis can be removed and purified using conventional protein isolation techniques.

Purification of capsids, VLPs or proteins may also include methods generally known in the art. For example, following capsid expression and cell lysis, the resulting lysate can be subjected to one or more isolation or purification steps. Such steps may include for example enzymatic lipolysis, DNA hydrolysis, and proteolysis steps. A proteolysis step may be performed for example using a blend of endo- and exo-proteases. For example, after cell lysis and hydrolytic disassembly of most cell components, such capsids with their cargo molecules can be separated from surrounding matrix by extraction, for example into a suitable non-polar water-immiscible solvent, or by crystallization from a suitable solvent. For example, hydrolysis and/or proteolysis steps transform contaminants from the capsid that are contained in the lysate matrix into small, water soluble molecules. Hydrophobic capsids may then be extracted into an organic phase such as 1, 3-bis(trifluoromethyl)benzene. Purification of capsids, VLPs or proteins may include for example at least one liquid-liquid extraction step, at least one fractional precipitation step, at least one ultrafiltration step, or at least one crystallization step. A liquid-liquid extraction may comprise for example use of an immiscible non-aqueous non-polar solvent, such as but not limited to benzene, toluene, hexane, heptane, octane, chloroform, dichloromethane, or carbon tetrachloride. Purifying may include at least one crystallization step. Use of one or more hydrolytic steps, and especially of one or more proteolytic steps, eliminates certain problems observed with current separation processes used for cargo molecules, which are mainly result from the large number and varying degree of binding interactions which take place between cargo molecules and components derived from the cell culture in which they are produced. The capsids described herein resist hydrolytic steps such that the matrix which results after hydrolysis includes intact capsids which safely partition any cargo molecules from the surrounding matrix, thereby interrupting the troublesome binding interactions which interfere with current purification processes.

Following purification, the capsid can be opened to obtain the cargo molecule, which maybe a protein or polypeptide, a peptide, or a nucleic acid molecule as described herein. Capsids can be opened using any one of several possible procedures known in the art, including for example heating in an aqueous solution above 50° C.; repeated freeze-thawing; incubating with denaturing agents such as formamide; by incubating with one or more proteases; or by a combination of any of these procedures.

Capsid proteins which are resistant to hydrolases and useful in the VLPs and methods according to the present disclosure can also be variants of, or derived from the wild type MS2 capsid protein. Capsid proteins may comprise, for example, at least one substitution, deletion or insertion of an amino acid residue relative to the wild type MS2 capsid amino acid sequence. Such capsid proteins may be naturally occurring variants or can be obtained by genetically modifying the MS2 capsid protein using conventional techniques, provided that the variant or modified capsid protein forms a non-enveloped capsid which is resistant to hydolysis catalyzed by a peptide bond hydrolase category E.C. 3.4 as described herein.

Genetically modified MS2 capsid proteins which can assemble into capsids which are resistant to hydrolysis as described herein can be engineered by making select modifications in the amino acid sequence according to conventional and well-known principles in physical chemistry and biochemistry to produce a protein which retains resistance to hydrolysis as described herein and in the Examples herein below.

It is common knowledge for example that the shape or global fold of a functional protein is determined by the amino acid sequence of the protein, and that the fold defines the protein's function. The global fold is comprised of one or more folding domains. When more than one folding domain exists in the global fold, the domains generally bind together, loosely or tightly along a domain interface. The domain fold can be broken down into a folding core of tightly packed, well-defined secondary structure elements, which is primarily responsible for the domain's shape and a more mobile outer layer typically comprised of turns and loops whose conformations are influenced by interactions with the folding core as well as interactions with nearby domains and other molecules, including solvent and other proteins. An extensive public domain database of protein folds, the Structural Classification of Proteins (SCOP) database (Alexey G Murzin, Cmr Opin Struct Biol (1996) 6, 386-394) of solved protein structures in the public domain is maintained online at scop.berkeley.edu and regularly expanded as new solved structures enter the public domain (Protein Data Bank (F. C. Bemstein, T. F. Koetzle, G. J. Williams, E. E. Meyer Jr., 5 M. D. Brice, J. R. Rodgers, O. Kennard, T. Shimanouchi, M. Tasumi, "The Protein Data Bank: A Computer-based Archival File For Macromolecular Structures," J. of. Mol. Biol., 112 (1977): 535), available online at rcsb.org) database. Members of a family which are evolutionarily distant, yet have the same shape and very similar function, commonly retain as few as 30% identical residues at topologically and/or functionally equivalent positions. In some families, sequences of distant members have as few as 20% of their residues unchanged with respect to each other, e.g. levi- and alloleviviridae capsid proteins. Further, the fold and function of a protein is remarkably tolerant to change via directed or random mutation, even of core residues (Peter O. Olins, S. Christopher Bauer, Sarah Braford-Goldberg, Kris Sterbenz, Joseph O. Polazzi, Maire H. Caparon, Barbara K. Klein, Alan M. Easton, Kumnan Paik, Jon A. Klover, Barrett R. Thiele, and John P. McKeam (1995) J Biol Chem 270, 23754-23760; Yiqing Feng, Barbara K. Klein and Charles A. McWherter (1996), J Mol Biol 259, 524-541; Dale Rennell, Suzanne E. Bouvier, Larry W. Hardy and Anthony R. Poteete! (1991) J Mol Biol 222, 67-87), insertion/deletion of one or more residues (Yiqing Feng, Barbara K. Klein and Charles A. McWherter (1996), J Mol Biol 259, 524-541), permutation of the sequence (Multi-functional chimeric hematopoietic fusion proteins between sequence rearranged c-mpl receptor agonists and other hematopoietic factors, U.S. Pat. No. 6,066,318), concatenation via the N- or C-terminus or both (to copies of itself or other peptides or proteins) (Multi-functional chimeric hematopoietic fusion proteins between sequence rearranged g-csf receptor agonists and other hematopoietic factors, US20040171115; Plevka, P., Tars, K., Liljas, L. (2008) Protein Sci. 17: 173) or covalent modification, e.g., glycosylation, pegylation, SUMOylation or the addition of peptidyl or nonpeptidyl affinity tags as long as the residues critical to maintaining the fold and/or function are spared.

VLPs according to the present disclosure and as used in any of the methods and processes, thus encompass those comprising a capsid protein having at least 15%, 16%, 21%, 40%, 41%, 52%, 53%, 56%, 59% or at least 86% sequence identity with the amino acid sequence of wild type Enterobacteria phage MS2 capsid protein (SEQ ID NO: 3). Such VLPs include for example a VLP comprising a capsid protein having at least 52% sequence identity with SEQ ID NO: 3) as described above. Also included is a VLP comprising a capsid protein having at least 53% sequence identity to SEQ ID NO:3, which can be obtained substantially as described above but not disregarding the FR capsid sequence, representing 53% sequence identity to wild-type enterobacteria phage MS2 capsid protein (SEQ ID NO:3). Also included is a VLP comprising a capsid protein having at least 56% sequence identity to SEQ ID NO:3, when it is considered that when the structures identified as 1AQ3 (van den Worm, S. H., Stonehouse, N. J., Valegard, K., Murray, J. B., Walton, C., Fridborg, K., Stockley, P. G., Liljas, L. (1998) Nucleic Acids Res. 26: 1345-1351), 1GAV (Tars, K., Bundule, M., Fridborg, K., Liljas, L. (1997) J. Mol. Biol. 271: 759-773), 1FRS (Liljas, L., Fridborg, K., Valegard, K., Bundule, M., Pumpens, P. (1994) J. Mol. Biol. 244: 279-290) and 2VTU (Plevka, P., Tars, K., Liljas, L. (2008) Protein Sci. 17: 1731) (Protein Data Bank identifiers described above), only 56% of the sequence positions have identical sequence and topologically equivalent positions with respect to the backbone overlays when all three sequences are considered together. Also included is a VLP comprising a capsid protein having at least 59% sequence identity to SEQ ID NO:3, when it is considered that the sequence of the MS2 viral capsid protein compared to that of the GA viral capsid protein is 59%. Also included is a VLP comprising a capsid protein having at least 86% sequence identity to SEQ ID NO:3, when it is considered that the sequence of the MS2 viral capsid protein compared to that of the FR capsid protein is 86%. VLPs according to the present disclosure thus encompass those comprising a capsid protein having at least 15%, 16%, or 21% sequence identity with the amino acid sequence of wild type Enterobacteria phage MS2 capsid (SEQ ID NO:3) based on a valid structure anchored alignment and is resistant to hydrolysis catalyzed by a peptide bond hydrolase category EC 3.4.

A VLP may thus comprise any of the MS2 capsid protein variants as described herein. Genetically modified capsid proteins consistent with those described herein can be produced for example by constructing at least one DNA plasmid encoding at least one capsid protein having at least one amino acid substitution, deletion or insertion relative to the amino acid sequence of the wild type MS2 capsid protein, making multiple copies of each plasmid, transforming a cell line with the plasmids; maintaining the cells for a time and under conditions sufficient for the transformed cells to express and assemble capsids encapsidating nucleic acids; lysing the cells to form a cell lysate; subjecting the cell lysate to hydrolysis using at least one peptide bond hydrolase, category EC 3.4; and removing intact capsids remaining in the cell lysate following hydrolysis to obtain capsids having increased resistance to at least one hydrolase relative to the wild type capsid protein. Following purification of the resulting, intact capsids, an amino acid sequence for each capsid protein may be determined according to methods known in the art.

The specialized capsids described herein, can be used in research and development and in industrial manufacturing facilities to provide improved yields, since the purification processes used in both settings have the same matrix composition. Having such same composition mainly depends on using the same cell line in both research and development and manufacturing processes. However, differences in matrix composition due to using different cell lines are greatly reduced after proteolytic steps used in both research and development and manufacturing stages. This feature enables use of different cell lines in both stages with a minimal manufacturing yield penalty.

EXAMPLES

The following non-limiting examples are included to illustrate various aspects of the present disclosure. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, appreciate that many changes can be made in the specific examples described, while still obtaining like or similar results, without departing from the scope of the invention. Thus, the examples are exemplary only and should not be construed to limit the invention in any way. To the extent necessary to enable and describe the instant invention, all references cited are herein incorporated by reference.

Example A

Propagation of MS2 Bacteriophage

MS2 bacteriophage (ATCC No. 15597-B1, from American Type Culture Collection, Rockville, Md.) and its *E. coli* host (ATCC No. 15669) were obtained from ATCC and propagated using the procedure described by Strauss and Sinsheimer (1963) J. Mol. Biol 7:43-54 J. Mol. Biol 7:43-54. Results are plotted in FIG. 1. Optical Density (OD) at 600 nm and pH were followed during the reaction. ODi represents OD immediately after inoculation with host. Infection was done at 2.3 hours. Ln(OD/ODi) was plotted on the left axis (full diamonds) and pH was plotted on the right axis (open squares). This experiment was ended 5.3 hours after inoculation with host. Lysate obtained was centrifuged at 2,000 g and filtered through a 0.2 µm membrane to eliminate remaining bacteria and bacterial debris.

Example B

Purification of MS2 Bacteriophage Using Proteinase K and Ultrafiltration

Figure 2:
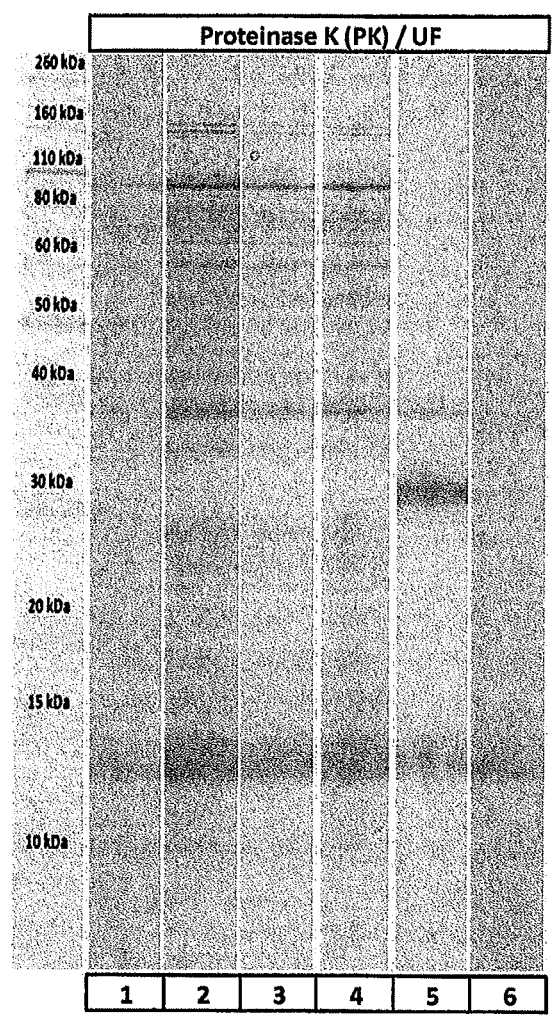
FIG. 2 is a gel showing results of SDS-PAGE analysis of MS2 bacteriophage samples obtained following propagation on *E. coli* and purified using Proteinase K and ultrafiltration, showing that Proteinase K purification yields phage purified to higher than 99% of total protein (band at 14 kDa corresponds to MS2 bacteriophage capsid protein).

Purification of MS2 bacteriophage was conducted as follows. Samples were taken during purification and SDS PAGE analysis was run on the samples. Results obtained are shown in FIG. 2. Eight milliliters of lysate obtained at end of Example A (sample in Lane 1, FIG. 2) was filtered through a 300 kDa membrane (Vivaspin 2, from Sartorius Stedim, Bohemia, N.Y.) and the filtrate was filtered through a 100 kDa membrane, from which 1 mL of retentate was obtained (sample in Lane 2, FIG. 2). This retentate was divided in two equal parts. To one half (control) 206 µL, 20 mM $CaCl_2$ aqueous solution at pH 7.5 were added. To the second half (Proteinase) 0.15 mg Proteinase K (Sigma Aldrich, St. Louis, Mo.) dissolved in 206 µL, 20 mM $CaCl_2$ aqueous solution at pH 7.5 was added. Both tubes were incubated at 37° C. and after 1 hour they were placed in an ice-water bath. Samples were then taken and analyzed: control sample in Lane 3, FIG. 2, and Proteinase sample in Lane 5, FIG. 2. Each product was then diluted to 2 mL with deionized (DI) water and filtered through a 100 kDa membrane. Each retentate (150 μL) was diluted to 2 mL with DI water and filtered again through the same membrane. Dilution and ultrafiltration was repeated one more time for each product. Samples of each retentate were then taken and analyzed: control sample in Lane 4, FIG. 2, and Proteinase sample in Lane 6, FIG. 2. The band at 14 kDa corresponds to MS2 bacteriophage's capsid protein. The band at 30 kDa corresponds to Proteinase K. Product from control experiment yields a highly impure phage. Product from the Proteinase experiment yields a product containing phage with purity higher than 99%.

Example C

Degradation of MS2 Bacteriophage

Figure 3:
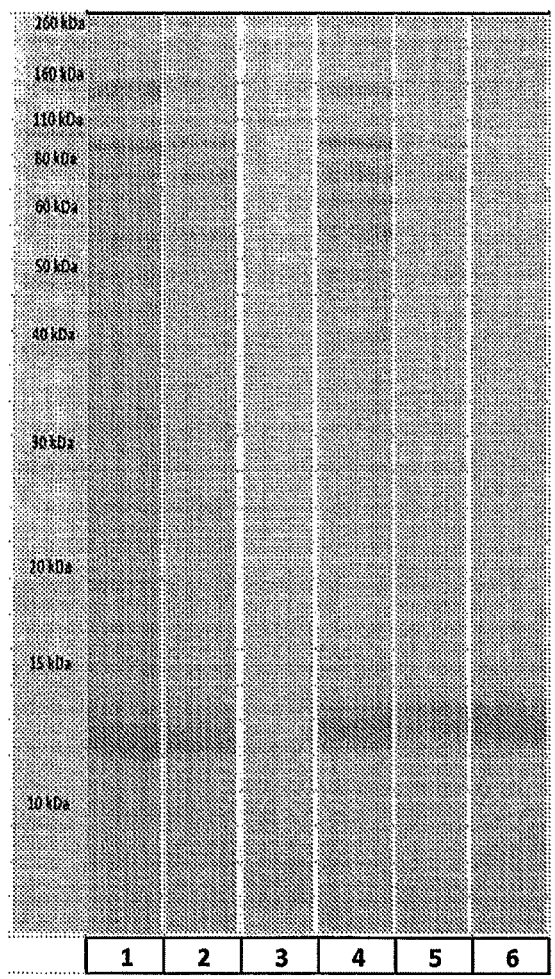
FIG. 3 is a gel showing results of SDS-PAGE analysis of partially purified MS2, showing complete degradation of the phage and results obtained after 1× or 2× ultrafiltration of the lysate (Lanes 4 and 6).

Treatment of MS2 bacteriophage was conducted as follows. Samples were taken during treatment and SDS PAGE analysis was run on the samples. Results obtained are shown in FIG. 3. Four milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. A sample of the aqueous solution after extraction with Freon 11 was taken and analyzed (sample in Lane 1, FIG. 3). To the partially purified phage solution (130 μL) 370 μL, of 20 mM $CaCl_2$ aqueous solution was added. The mixture was incubated at 37° C. and after 1 hour it was placed in an ice-water bath. A sample was then taken and analyzed: sample in Lane 2, FIG. 3. The incubation product was diluted to 2 mL with deionized (DI) water and filtered through a 100 kDa membrane. The retentate (150 μL) was diluted to 2 mL with DI water and filtered again through the same membrane. Dilution and ultrafiltration of the retentate was repeated one more time. A sample of the retentate was then taken and analyzed: sample in Lane 3, FIG. 3. Only weak bands at lower than 10 kDa were observed, indicating complete degradation of phage.

Example D

Purification of MS2 Bacteriophage Using Ultrafiltration

Purification of MS2 bacteriophage was conducted as follows. Samples were taken during purification and SDS PAGE analysis was run on the samples. Results obtained are shown in FIG. 3. Four milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. The aqueous solution containing partially purified phage was diluted to 2 mL with deionized water, filtered through a 300 kDa membrane and the filtrate was filtered through a 100 kDa membrane, from which 150 μl of retentate was obtained. The retentate was then diluted to 2 mL with deionized (DI) water and filtered through the same 100 kDa membrane. Dilution and ultrafiltration of the retentate (150 μL) was repeated one more time. A sample of the retentate was then taken and analyzed: sample in Lane 4, FIG. 3. 370 μL of 20 mM $CaCl_2$ aqueous solution was added to the retentate (130 μL). The mixture was incubated at 37° C. and after 1 hour it was placed in an ice-water bath. A sample was then taken and analyzed: sample in Lane 5, FIG. 3. The product was then diluted to 2 mL with deionized (DI) water and filtered through a 100 kDa membrane. The retentate (150 μL) was diluted to 2 mL with DI water and filtered again through the same membrane. Dilution and ultrafiltration of the retentate was repeated one more time. A sample of the retentate was then taken and analyzed: sample in Lane 6, FIG. 3. MS2's capsid protein, of 14 kDa, retained by a membrane through which permeate proteins with less than 100 kDa molecular weight is clearly visible, indicating the presence of intact MS2 capsids. The product obtained contained phage with purity higher than 99%.

Example E

Purification of MS2 Bacteriophage Using Proteinase K, and Ultrafiltration

Figure 4:
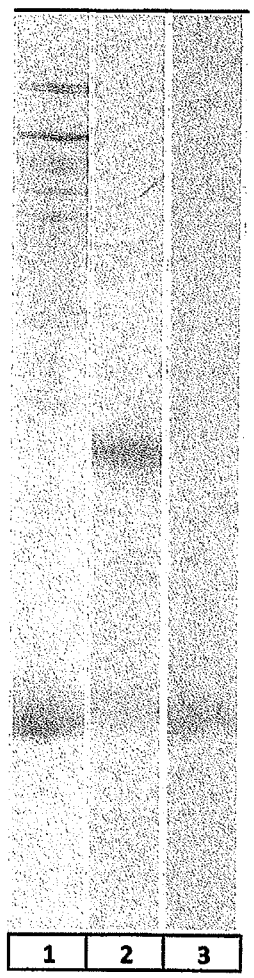
FIG. 4 is a gel showing results of SDS-PAGE analysis of MS2 samples purified using ultrafiltration and Proteinase K treatment.

Purification of MS2 bacteriophage was conducted as follows. Samples were taken during purification and SDS PAGE analysis was run on the samples. Results obtained are shown in FIG. 4. Four milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. The aqueous solution containing partially purified phage was diluted to 2 mL with deionized water, filtered through a 100 kDa membrane, from which 150 μL of retentate was obtained. The retentate was then diluted to 2 mL with deionized (DI) water and filtered through the same 100 kDa membrane. Dilution and ultrafiltration of the retentate (150 μL) was repeated one more time. A sample of the retentate was then taken and analyzed: sample in Lane 1, FIG. 4. 0.15 mg of Proteinase K dissolved in 370 μL of 20 mM $CaCl_2$ aqueous solution was added to the retentate (130 μL). The mixture was incubated at 37° C. and after 1 hour it was placed in an ice-water bath. A sample was then taken and analyzed: sample in Lane 2, FIG. 4. The product was then diluted to 2 mL with deionized (DI) water and filtered through a 100 kDa membrane. The retentate (150 μL) was diluted to 2 mL with DI water and filtered again through the same membrane. Dilution and ultrafiltration of the retentate was repeated one more time. A sample of the retentate was then taken and analyzed: sample in Lane 3, FIG. 4. The product obtained contained phage with purity higher than 99%.

Example F

Figure 5:
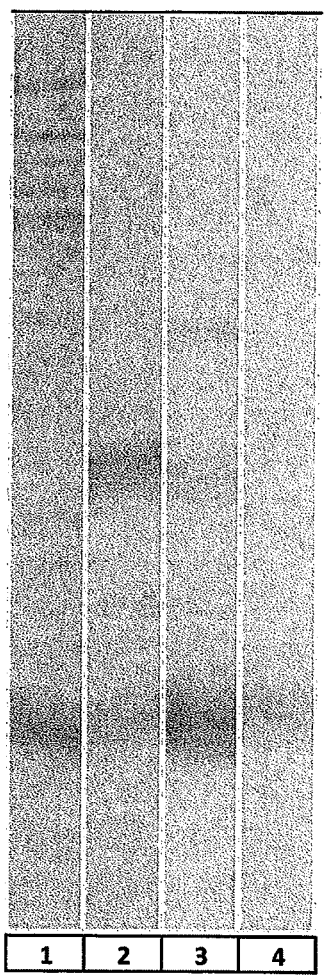
FIG. 5 is a gel showing results of SDS-PAGE analysis of MS2 samples purified using Proteinase K treatment, precipitation at acidic conditions, precipitation using ethanol at basic and acidic conditions, and ultrafiltration.
Figure 6:
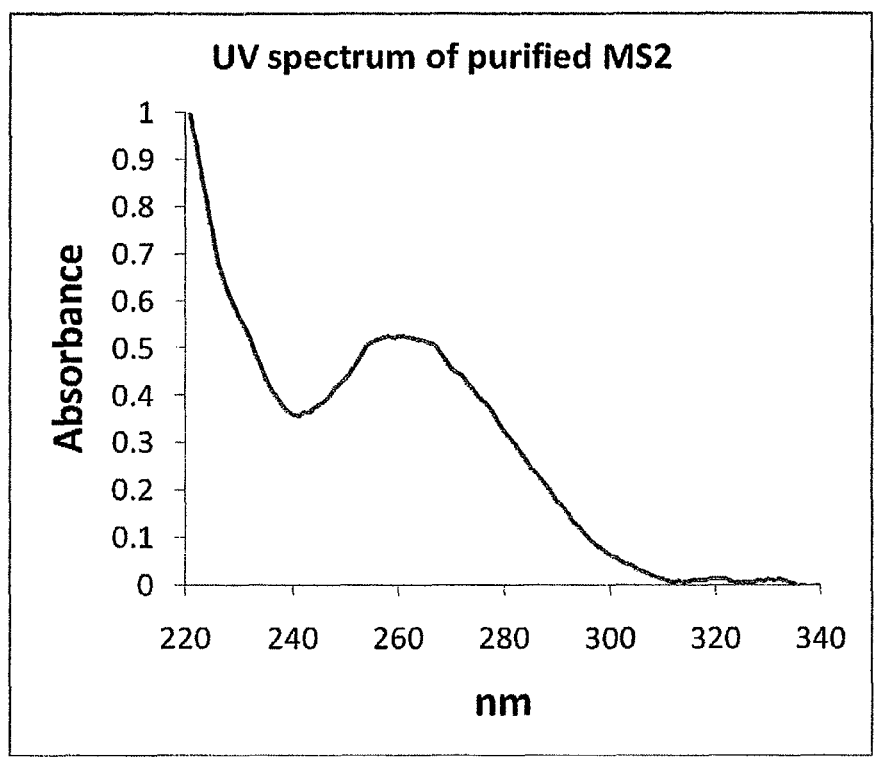
FIG. 6 is a graph showing the UV spectrum of MS2 samples purified using Proteinase K treatment, precipitation at acidic conditions, precipitation using ethanol at basic and acidic conditions, and ultrafiltration.
Figure 7:
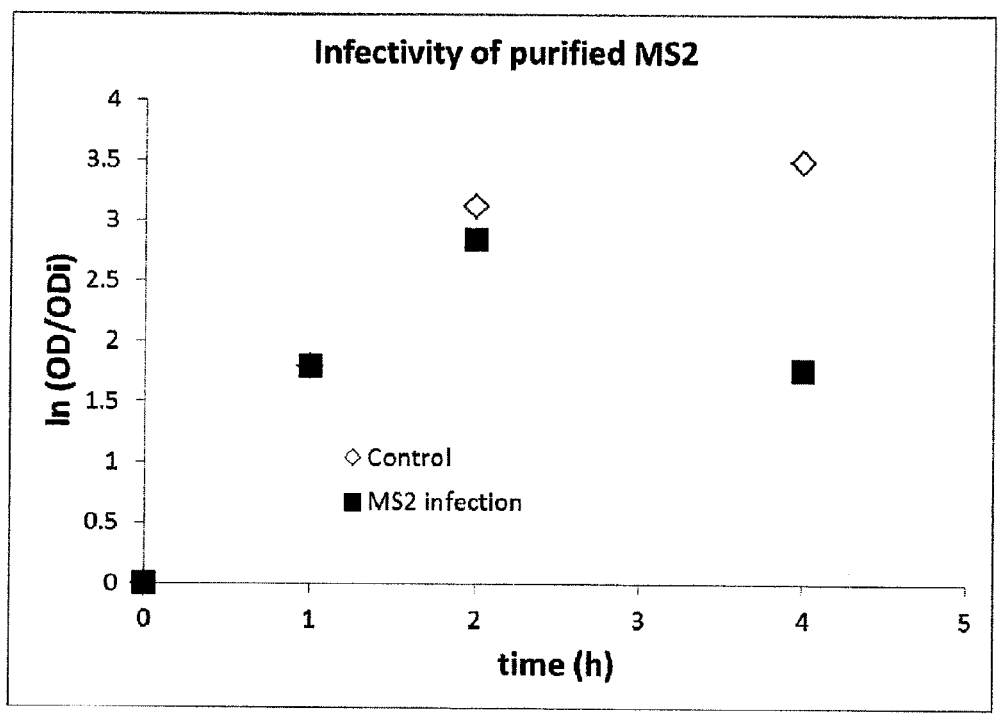
FIG. 7 is a plot of Optical Density (OD; filled diamonds) over time, obtained with a control sample (open diamonds) and an MS2 sample following purification described for FIGS. 5 and 6 (filled squares), showing that the purified sample contains phage with high infectivity.

Purification of MS2 Bacteriophage Using Proteinase K, Precipitation at Acidic Conditions, Precipitation Using Ethanol at Basic and Acidic Conditions, and Ultrafiltration Purification of MS2 bacteriophage was conducted as follows. Samples were taken during purification and SDS PAGE analysis was run on the samples. Results obtained are shown in FIG. 5. Fifty milliliters of lysate obtained at end of Example A was partially purified by precipitation using ammonium sulfate and extraction using trichlorofluoromethane (Freon 11) as described by Strauss & Sinsheimer (1963) J. Mol. Biol 7:43-54. A sample of the aqueous solution after extraction with Freon 11 was taken and analyzed (sample in Lane 1, FIG. 5). To the partially purified phage solution (1.2 mL) 0.9 mg of Proteinase K dissolved in 1.24 mL of 20 mM CaCl2 aqueous solution was added. The mixture was incubated at 37° C. and after 1 hour 60 μL of 0.2M Phenylmethanesulfonyl fluoride (PMSF) solution in ethanol was added to inactivate Proteinase K. The mixture was then placed in an ice-water bath. A sample was taken and analyzed: sample in Lane 2, FIG. 5.0. Six hundred and eighty microliters of 0.1% phosphoric acid aqueous solution was slowly added with vigorous agitation in an ice/water bath to bring the pH of the liquid to 4. The liquid was kept at 0° C. for 30 minutes and centrifuged at 16,000 g at 4° C. for 30 min. The supernatant was allowed to reach room temperature and 130 μL of 1% NaOH was added to bring the pH of the liquid to 8. 0.81 mL of ethanol at room temperature was slowly added with vigorous agitation to bring the ethanol concentration in the liquid to 20%. The liquid was kept at room temperature for 30 min and centrifuged at 16,000 g at room temperature for 30 min. The supernatant was placed in an ice/water bath for 15 min and 1.3 mL of 1% acetic acid was slowly added at 0° C. with vigorous agitation to bring the pH of the liquid to 4. 1.5 mL of ethanol at 0° C. was slowly added with vigorous agitation to bring the ethanol concentration in the liquid to 34%. The liquid was kept at 0° C. for 30 minutes and centrifuged at 16,000 g at 4° C. for 30 min. The pellet was resuspended in 200 μL of DI water and a 20 μL sample was taken and analyzed: Lane 3, FIG. 5. The rest (180 μL) was diluted with DI water to 2 mL and filtered through 100 kDa membrane. The retentate (150 μL) was diluted to 2 mL with DI water and filtered again through the same membrane. Dilution and ultrafiltration of the retentate was repeated one more time. A sample of the retentate was then taken and analyzed by SDS PAGE: sample in Lane 4, FIG. 5. MS2's capsid protein, of 14 kDa, retained by a membrane through which proteins with less than 100 kDa molecular weight are able to peoneate, is clearly visible, consistent with the presence of intact MS2 capsids. A UV spectrum on the same retentate is shown in FIG. 6, which is consistent with results published by G. F. Rohrmann and R. G. Krueger, (1970) J. Virol, 6(3):26 for pure MS2 phage. A Superdex 200 (GE Healthcare, Piscataway, N.J.) size exclusion chromatography was run on the same retentate using Tris-buffered saline at pH 7.4 and 150 mM NaCl. It showed 280 nm absorbance only at the void volume of the column. There was no absorbance in the elution volume for proteins of 600 kDa to 2 kDa. This test is consistent with intact phage particles. RNA was isolated from another sample of the same retentate using a QIAamp Viral RNA Mini Kit (Qiagen, Valencia, Calif.) and a DNA-free kit (Life Technologies, Grand Island, N.Y.), and reverse transcribed using a High Capacity cDNA Reverse Transcription Kit (Life Technologies). The presence or absence of three different sections of the MS2 genome was then interrogated in PCR experiments. The following pairs of primers were used, each primer named for the position of its first and last base in the MS2 genome, forward (F) and reverse (R) respectively: F1001_1021-R2180_2201, F1201_1223-R1979_2001, F1401_1426-R1680_1705. Platinum Taq DNA Polymerase High Fidelity (Life Technologies) was used for amplification. PCR products, analyzed in 1.5% agarose gel stained with Ethidium Bromide, as shown in FIG. 9 (1.2 kbp for primers F1201_1223-R1979_2001 in Lane 1, 800 bp for primers F1201_1223-R1979_2001 in Lane 2, and 304 bp for primers F1401_1426-R1680_1705 in Lane 3), were consistent with an intact MS2 bacteriophage genome. An infectivity test was also run on the same retentate as follows. Five microliters of retentate were used to infect 1 mL of bacterial culture as described in Example A at the point it reached an OD (600 nm) of 0.22. OD (600 nm) was 0.82 1 hour after infection and dropped to 0.21 after 2 additional hours, while during the same time a control sample attained OD (600 nm) of 0.82 1 hour after infection and 1.2 after 2 additional hours, as shown in FIG. 7. This test showed a highly infectious phage in the retentate and therefore demonstrated that the purification processes used to isolate it did not compromise its integrity. In conclusion, the product obtained contained MS2 bacteriophage with purity higher than 99%.

Example G

Purification of MS2 Bacteriophage Using Different Exogenous Proteases, and Ultrafiltration Purification of MS2 bacteriophage using different exogenous proteases was attempted substantially as described in Example E, with the exception that proteases other than Proteinase K were used. MS2 bacteriophage was successfully purified after proteolysis promoted by Protease from *Bacillus licheniformis* (P5380, Sigma Aldrich). However, a proteolysis reaction using Pepsin from porcine gastric mucosa (P6887, Sigma Aldrich) at pH of 6 was found to significantly degrade MS2 bacteriophage. On the other hand, proteolysis reactions using Papain from *papaya* latex (P3125, Sigma Aldrich) at pH 6 did not extensively degrade MS2 bacteriophage.

Example H

Figure 8:
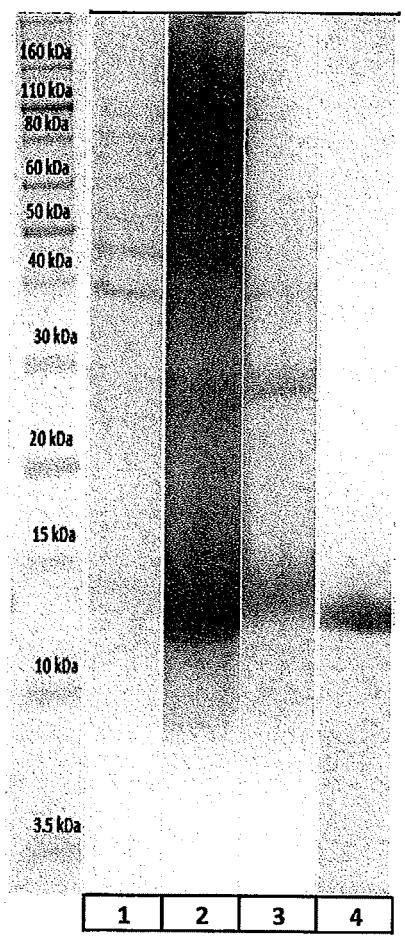
FIG. 8 is a gel showing results of SDS-PAGE analysis of VLP samples following expression of MS2 capsids encapsidating RNA coding for the capsid protein attached to an MS2 capsid specific 19-mer RNA hairpin.

Production of MS2 Capsids Encapsidating RNA Coding for its Capsid Protein Attached to its Specific 19-Mer RNA Hairpin Production of MS2 capsids was conducted as follows. Samples were taken during the course of expression and SDS PAGE analysis was run on the samples to monitor capsid production. Results obtained are shown in FIG. 8. A DNA sequence, SEQ ID NO: 4, encoding MS2's capsid protein and its specific RNA 19-mer packing sequence was cloned into an entry plasmid as an SfiI restriction fragment and then subcloned by Gateway recombination into pDEST14 (Life Technologies).

One Shot BL21/DE3 Chemically Competent *E. coli* (Life Technologies) cells were transformed using such plasmid. BL21/DE3 containing the plasmid was grown in 750 mL of LB medium containing ampicillin at 37° C., to an OD (600 nm) equal to 0.8. A pre-induction sample was then taken and analyzed: sample in Lane 1, FIG. 8. Isopropyl β-D-1-thiogalactopyranoside (Sigma-Aldrich) (IPTG) was then added to a final concentration of 1 mM. Four hours post-induction cells were harvested by centrifugation at 3,000 g and 4° C. for 40 min. A sample was then taken and analyzed: sample in Lane 2, FIG. 8.

Example I

Purification and Characterization of MS2 Capsids Encapsidating RNA Coding for its Capsid Protein Attached to its Specific 19-Mer RNA Hairpin Purification of MS2 capsids was conducted as follows. Samples were taken during purification and SDS PAGE analysis was run on the samples. Results obtained are shown in FIG. 8. A fraction of the pellet from Example H equivalent to 115 mL of culture was resuspended in 20 mM Tris-HCl, pH 7.5, containing 10 mM MgCl$_2$ and sonicated to lyse cells.

Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. To the partially purified MS2 capsid solution (1.05 mL) 0.3 mg of Proteinase K dissolved in 1.05 mL of 20 mM CaCl2 aqueous solution was added. The mixture was incubated at 37° C. and after 2.5 hours it was placed in an ice-water bath. A sample was then taken and analyzed: sample in Lane 3, FIG. 8. Fifteen minutes afterwards, 0.14 mL of 1% phosphoric acid aqueous solution was slowly added with vigorous agitation in an ice/water bath to bring the pH of the liquid to 4.1. The liquid was kept at 0° C. for 30 minutes and centrifuged at 16,000 g at 4° C. for 20 min. To the supernatant, kept at 0° C., 100 µL, of 1% NaOH was added to bring the pH of the liquid to 7.9. Five hundred microliters of ethanol at 0° C. was then slowly added with vigorous agitation to bring the ethanol concentration in the liquid to 20%. The liquid was kept at 0° C. for 30 minutes and centrifuged at 16,000 g at 4° C. for 20 min. After adding 1% acetic acid to adjust the pH of the solution to 7, the supernatant was filtered through a Vivaspin 2 (Sartorius) 300 kDa membrane and the filtrate was filtered through a 100 kDa membrane, from which 150 µL of retentate was obtained. The retentate was then diluted to 2 mL with phosphate buffered saline and filtered through the same 100 kDa membrane. Dilution and ultrafiltration of the retentate (150 µL) was repeated four more times. A sample of the retentate was then taken and analyzed by SDS PAGE: sample in Lane 4, FIG. 8. MS2's capsid protein, of 14 kDa, retained by a membrane through which proteins with less than 100 kDa molecular weight are able to permeate, is clearly visible, consistent with the presence of intact MS2 capsids. RNA was isolated from another sample of the same retentate using a QIAamp Viral RNA Mini Kit (Qiagen, Valencia, Calif.) and a DNA-free kit (Life Technologies, Grand Island, N.Y.), and reverse transcribed using a High Capacity cDNA Reverse Transcription Kit (Life Technologies). The presence or absence of a section of the MS2 capsid was then interrogated in PCR experiments. The following pair of primers was used, each primer named for the position of its first and last base in the MS2 genome, forward (F) and reverse (R) respectively: F1401_1426-R1680_1705. Platinum Taq DNA Polymerase High Fidelity (Life Technologies) was used for amplification. The PCR product, analyzed in 2% agarose gel stained with Ethidium Bromide, as shown in FIG. 10 (304 bp in Lane 1; the leftmost Lane corresponds to 1 kb plus ladder from Life Technologies), was consistent with an intact MS2 capsid gene. In conclusion, the product obtained contained MS2 capsids with purity higher than 99%.

Example J

Simple Precipitation with Ethanol for Purification of VLPs

Figure 11:
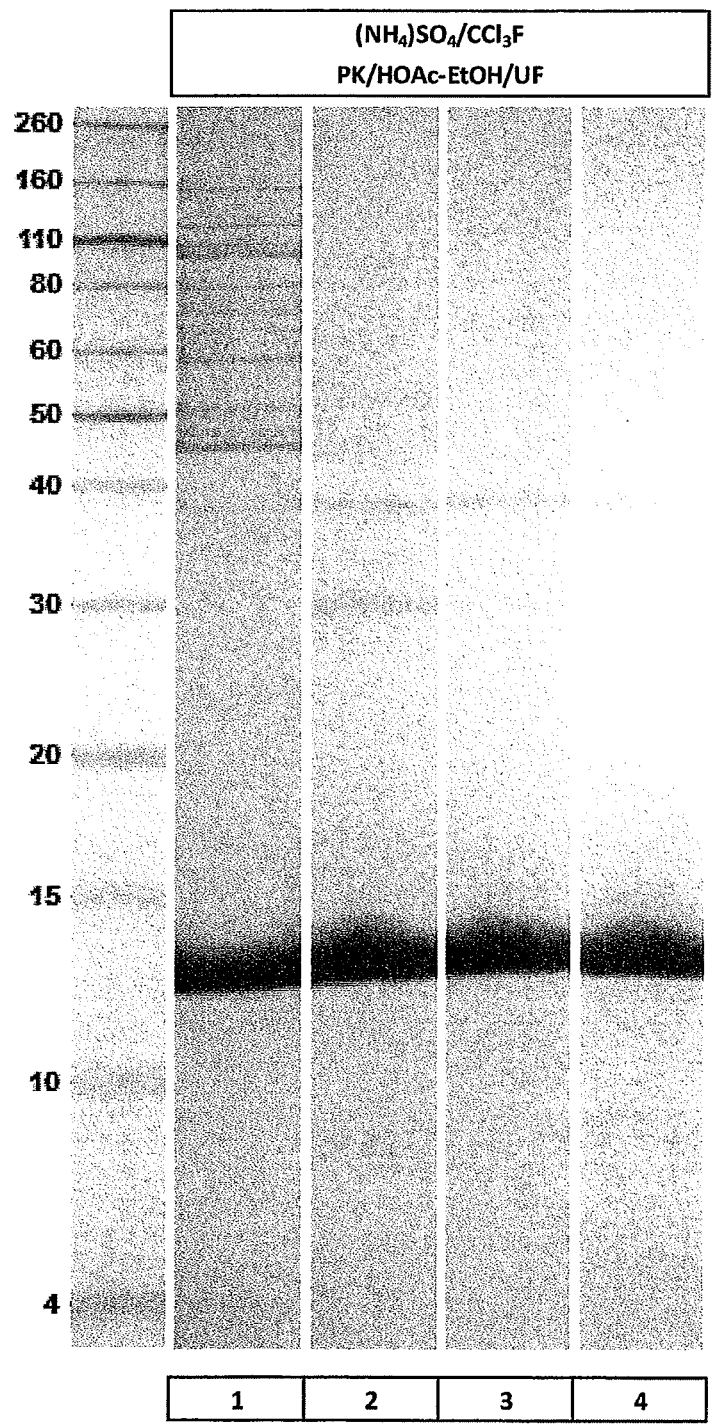
FIG. 11 is a gel showing results of SDS-PAGE analysis of VLP samples following simple precipitation with ethanol for purification of VLPs and following use of Proteinase K (PK).

Purification of VLPs was conducted as follows. Samples were taken during purification and SDS PAGE analysis was run on the samples. Results obtained are shown in FIG. 11. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. A sample was taken and analyzed: sample in Lane 1, FIG. 11. A strong band at about 14 kDa was found, consistent with the capsid protein of MS2 phage. Other bands, impurities of higher molecular weight, represent about 27% of the sample weight. To the partially purified VLP solution (1.35 mL) 1.36 mL of 20 mM $CaCl_2$ aqueous solution was added and placed in an ice-water bath. Fifteen minutes afterwards, 50 µL of 10% acetic acid aqueous solution was added to bring the pH of the liquid to 4.1. Then, at the same temperature and with vigorous agitation, 1.44 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mM$MgCl_2$ adjusted to pH 7.5. A sample was taken and analyzed by SDS PAGE: sample in Lane 2, FIG. 11. Impurities in this sample represented about 24% of the sample weight. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 3, FIG. 11. Impurities in this sample represented about 9.7% of the sample weight. In conclusion, the product obtained contained VLPs with purity higher than 90%.

Example K

Figure 12:
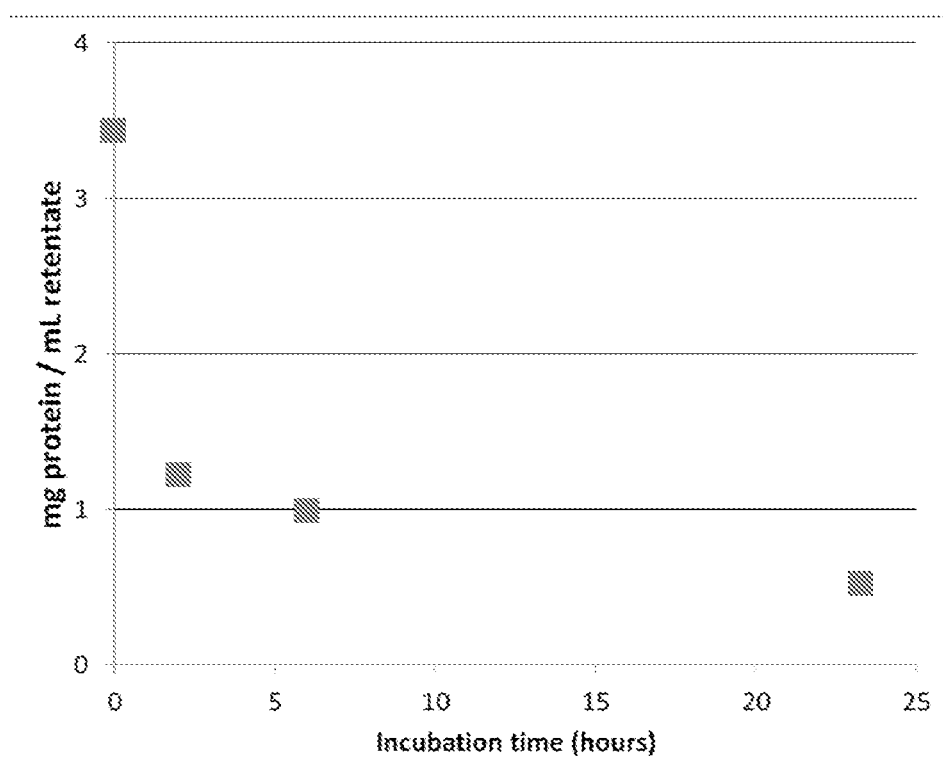
FIG. 12 is a plot of protein resistant to protease treatment after simple precipitation with ethanol (without prior treatment with Proteinase K) for purification of VLPs.

Use of Proteinase K (PK) and Simple Precipitation with Ethanol for Purification of MS2 VLPs Purification of VLPs was conducted as follows. Samples were taken during purification and SDS PAGE analysis was run on the samples. Results obtained are shown in FIG. 11. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. A sample was taken and analyzed: sample in Lane 1, FIG. 11. A strong band at about 14 kDa was found, consistent with the capsid protein of MS2 phage. Other bands, impurities of higher molecular weight, represent about 26% of the sample weight. To the partially purified VLP solution (1.35 mL) 0.6 mg of Proteinase K dissolved in 1.36 mL of 20 mM $CaCl_2$ aqueous solution was added. The mixture was incubated at 37° C. and after 2.5 hours placed in an ice-water bath. A sample was taken and analyzed by SDS PAGE: sample in Lane 2, FIG. 12. Impurities in this sample represented about 14% of the sample weight. Fifteen minutes afterwards, about 50 µL of 10% acetic acid aqueous solution was added in an ice/water bath to bring the pH of the liquid to 4.1. Then, at the same temperature and with vigorous agitation, 1.54 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mM $MgCl_2$ adjusted to pH 7.5. A sample was taken and analyzed by SDS PAGE: sample in Lane 3, FIG. 12. Impurities in this sample represented about 10% of the sample weight. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 4, FIG. 12. Impurities in this sample represented about 5.1% of the sample weight. In conclusion, the product obtained contained VLPs with purity of about 95%.

Example L

Degrading MS2 VLPs Using Selective Protease

An aliquot of purified VLPs obtained in Example K, amounting to 1.17 mL of suspension containing 1.9 mg of capsid protein, was diluted with 1.83 mL of an aqueous solution of 10 mM sodium acetate and 5 mM calcium acetate. The pH of the solution was adjusted to 7.5 using 0.1% sodium hydroxide. 0.6 mg protease from *Streptomyces griseus* (Sigma-Aldrich, St. Louis, Mo.) was added and a 0.7 mL sample was then taken. The remaining mixture was incubated at 37° C. for 2 hours and a second 0.7 mL sample was taken. Two more samples were taken, after 6 hours of incubation and 23 hours of incubation. Each of the four 0.7 mL samples was filtered through a 100 kDa ultrafiltration membrane (Vivaspin 2, from Sartorius Stedim, Bohemia, N.Y.) and washed with aqueous buffer consisting of 20 mM Tris-HCl and 10 mM $MgCl_2$ adjusted to pH 7.5. Total protein recovered (concentration measured using Pierce® BCA Protein Assay Kit, Thermo Fisher Scientific, Rockford, Ill.) in each of the 4 retentates obtained after ultrafiltration was related to protein present before ultrafiltration. 105% recovery was calculated for the first sample (before starting incubation). 37% recovery was calculated after 2 hours incubation. 30% recovery was calculated after 6 hours incubation. 28% recovery was calculated after 23 hours of incubation. Protein concentration vs. time is plotted in FIG. 12.

These results indicate that the protein recovered by direct precipitation of a cell lysate without prior heterologous protease treatment, includes unassembled capsid protein or partially assembled capsids which, unlike fully assembled capsids, remain sensitive to heterologous proteases. Thus, pretreatment of cell lysates with a heterologous protease can remove all forms of the capsid protein except those incorporated into fully assembled capsids.

Example M

Figure 13:
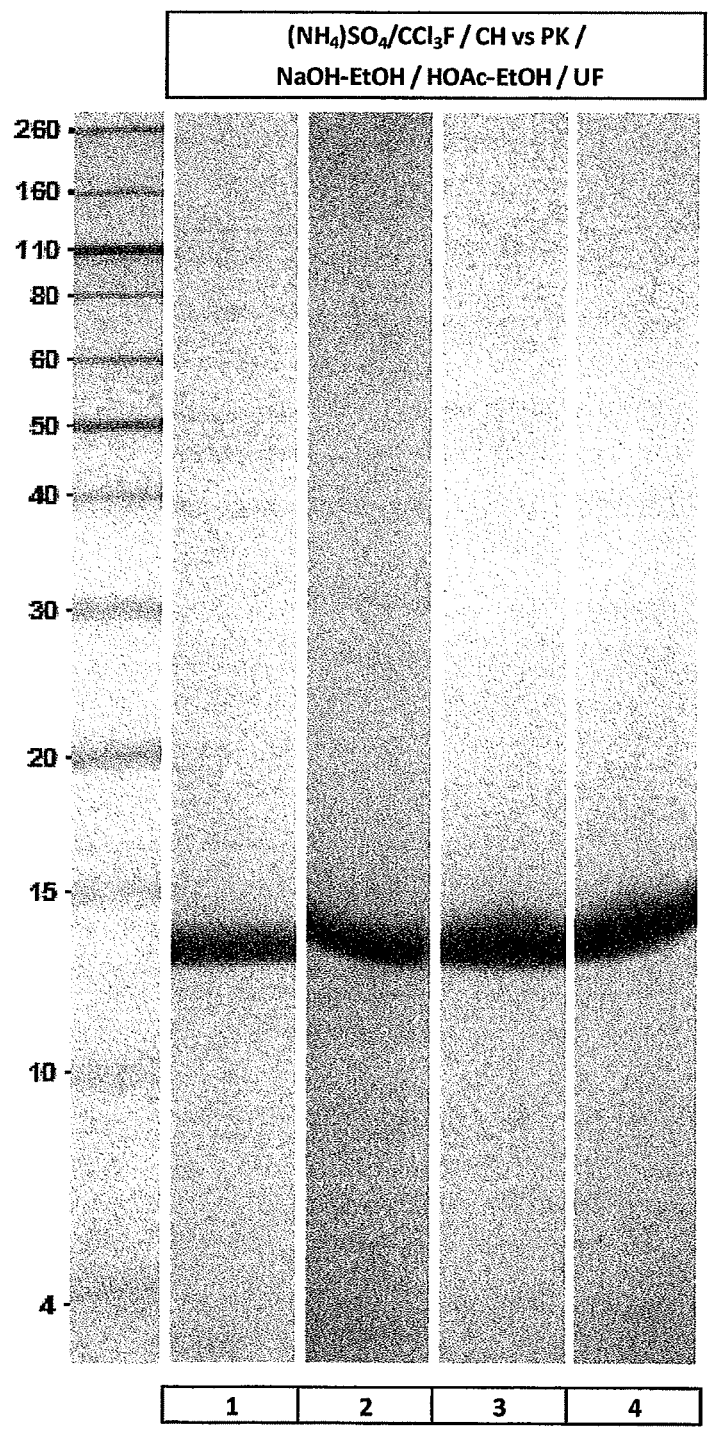
FIG. 13 is a gel showing results of SDS-PAGE analysis of VLP samples following use of constitutive hydrolases (CH) or Proteinase K (PK), fractional precipitation with ethanol, and ultrafiltration for purification of VLPs.

Use of Constitutive Hydrolases (CH), Fractional Precipitation with Ethanol, and Ultrafiltration for Purification of MS2 VLPs Purification of VLPs was conducted as follows. Samples were taken during purification and SDS PAGE analysis was run on the samples. Results obtained are shown in FIG. 13. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. To the partially purified MS2 VLP solution (1.35 mL) 1.36 mL of 20 mM $CaCl_2$ aqueous solution was added. The mixture was incubated at 37° C. for 2.5 hours (to allow constitutive hydrolases to act) and afterwards was placed in an ice-water bath. A sample was taken and analyzed by SDS PAGE: sample in Lane 1, FIG. 13. Impurities in this sample represented about 12% of the sample weight. Fifteen minutes afterwards, about 120 µL, of 1% sodium hydroxide aqueous solution was added in an ice/water bath to bring the pH of the liquid to 7.86. Then, at the same temperature and with vigorous agitation, 0.81 mL of ethanol was slowly added. The liquid was kept at 0° C. for 30 minutes and centrifuged at 16,000 g at 4° C. for 20 min. About 100 of 10% acetic acid aqueous solution was slowly added to the supernatant with vigorous agitation in an ice/water bath to bring the pH of the liquid to 4.0. Then, at the same temperature and with vigorous agitation, 1.3 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HCl and 10 mM $MgCl_2$ adjusted to pH 7.5. The diluted sample was filtered through a Vivaspin 2 (Sartorius) 100 kDa membrane from which 200 µL of retentate was obtained. The retentate was then diluted to 2 mL with the same buffer and filtered through the same 100 kDa membrane. Dilution and ultrafiltration of the retentate (200 µL) was repeated four more times. A sample of the retentate was then taken and analyzed by SDS PAGE: sample in Lane 3, FIG. 13. Impurities in this sample represented about 4.7% of the sample weight. In conclusion, the product obtained contained MS2 VLPs with purity higher than about 95%.

Example N

Use of Proteinase K (PK), Fractional Precipitation with Ethanol, and Ultrafiltration for Purification of MS2 VLPs Purification of VLPs was conducted as follows. Samples were taken during purification and SDS PAGE analysis was run on the samples. Results obtained are also shown in FIG. 13. One sixth of the pellet obtained from an experiment identical to Example H was resuspended in 20 mM Tris-HCl, pH 7.5, containing 10 mM $MgCl_2$ and sonicated to lyse cells. Cell debris was removed by centrifugation at 16,000 g. The cell lysate obtained was partially purified by precipitation using ammonium sulfate and extraction using trichlorofluoromethane (Freon 11) as described by Strauss & Sinsheimer (1963) J. Mol. Biol 7:43-54. To the partially purified VLP solution (1.35 mL) 0.3 mg of Proteinase K dissolved in 1.36 mL of 20 mM $CaCl_2$ aqueous solution was added. The mixture was incubated at 37° C. for 2.5 hours and afterwards was placed in an ice-water bath. A sample was taken and analyzed by SDS PAGE: sample in Lane 2, FIG. 13. Impurities in this sample represented about 8.1% of the sample weight. Fifteen minutes afterwards, about 120 µL of 1% sodium hydroxide aqueous solution was added in an ice/water bath to bring the pH of the liquid to 7.86. Then, at the same temperature and with vigorous agitation, 0.81 mL of ethanol was slowly added. The liquid was kept at 0° C. for 30 minutes and centrifuged at 16,000 g at 4° C. for 20 min. About 100 µL of 10% acetic acid aqueous solution was added to the supernatant in an ice/water bath to bring the pH of the liquid to 4.0. Then, at the same temperature and with vigorous agitation, 1.3 mL of ethanol was slowly added. The liquid was kept at 0° C. for 30 minutes and centrifuged at 16,000 g at 4° C. for 20 min. The pellet was suspended in 2 mL of an aqueous buffer consisting of 20 mM Tris-HC 1 and 10 mM $MgCl_2$ adjusted to pH 7.5. The diluted sample was filtered through a Vivaspin 2 (Sartorius) 100 kDa membrane from which 200 μL of retentate was obtained. The retentate was then diluted to 2 mL with the same buffer and filtered through the same 100 kDa membrane. Dilution and ultrafiltration of the retentate (200 μL) was repeated four more times. A sample of the retentate was then taken and analyzed by SDS PAGE: sample in Lane 4, FIG. 13. Impurities in this sample represented about 0.9% of the sample weight. In conclusion, the product obtained contained VLPs with purity higher than about 99%.

Example O

Figure 14:
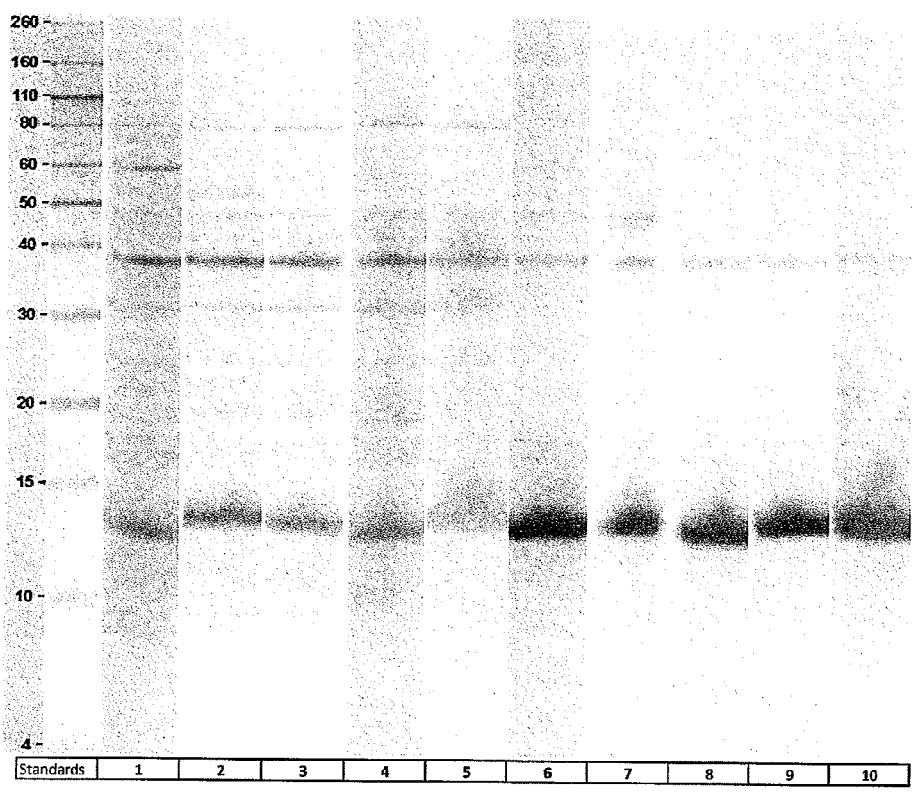
FIG. 14 is a gel showing results of SDS-PAGE analysis of VLP samples following use of various hydrolases, and factional precipitation with ammonium sulfate for purification of VLPs.

Use of Various Hydrolases, and Fractional Precipitation with Ammonium Sulfate for Purification of VLPs Purification of VLPs was conducted as follows. Samples were taken during purification and SDS PAGE analysis was run on the samples. Results obtained are shown in FIG. 14. One sixth of the pellet obtained from the method of Example H was resuspended in 20 mM Tris-HCl, pH 7.5, containing 10 mM $MgCl_2$ and sonicated to lyse cells. Cell debris was removed by centrifugation at 16,000 g. A sample of the supernatant was taken and analyzed by SDS PAGE: sample in Lane 1, FIG. 14. Impurities in this sample represented about 70% of the sample weight. Four other identical fractions of the pellet obtained from such experiment identical to Example H were processed in the same manner.

The five centrifuged cell lysates obtained, each 3.7 mL in volume, were further processed in five different manners, as follows. The first centrifuged cell lysate was placed in an ice-water bath for 15 minutes and 0.1 grams of ammonium sulfate was added. The mixture was vortexed until complete dissolution of ammonium sulfate was achieved. The liquid was kept at 0° C. for 2 hours and centrifuged at 16,000 g at 4° C. for 30 min. 0.4 grams of ammonium sulfate was added to the supernatant and vortexed until complete dissolution of ammonium sulfate was achieved. The liquid was kept at 0° C. for 2 hours and centrifuged at 16,000 g at 4° C. for 30 min. The purified VLP pellet was suspended in 0.2 mL of an aqueous buffer consisting of 20 mM Tris-HCl and 10 mM $MgCl_2$ adjusted to pH 7.5. The second centrifuged cell lysate was incubated at 37° C. for five hours, placed in an ice-water bath for the same amount of time as the first centrifuged cell lysate and subsequently processed in identical manner as the first centrifuged cell lysate. One hundred and fifty micrograms of Proteinase K (Sigma Aldrich, St. Louis, Mo.) was added to the third centrifuged cell lysate which was then incubated at 37° C. for five hours, placed in an ice-water bath for the same amount of time as the first centrifuged cell lysate and subsequently processed in identical manner as the first centrifuged cell lysate. The fourth centrifuged cell lysate was incubated at 37° C. for two hours. 0.15 mg of Proteinase K was then added. The sample was incubated at 37° C. for an additional three hours, placed in an ice-water bath for the same amount of time as the first centrifuged cell lysate and subsequently processed in identical manner as the first centrifuged cell lysate.

Five hundred units of Benzonase® Nuclease (Sigma Aldrich, St. Louis, Mo.) and 35 units of Lipase from *Candida rugosa* (Sigma Aldrich, St. Louis, Mo.) was added to the fifth centrifuged cell lysate and incubated at 37° C. for one hour. 15 units of α-Amylase from *Bacillus* sp. (Sigma Aldrich, St. Louis, Mo.) was then added and incubated at 37° C. for one additional hour. 0.15 mg of Proteinase K was then added. The mixture was incubated at 37° C. for an additional three hours, placed in an ice-water bath for the same amount of time as the first centrifuged cell lysate and subsequently processed in identical manner as the first centrifuged cell lysate.

A sample was taken of the second centrifuged cell lysate after its 5 hours incubation and analyzed by SDS PAGE: sample in Lane 2, FIG. 14. A sample was taken of the third centrifuged cell lysate after its 5 hours incubation and analyzed by SDS PAGE: sample in Lane 3, FIG. 14. A sample was taken of the fourth centrifuged cell lysate after its 5 hours incubation and analyzed by SDS PAGE: sample in Lane 4, FIG. 14. A sample was taken of the fifth centrifuged cell lysate after its 5 hours incubation and analyzed by SDS PAGE: sample in Lane 5, FIG. 14.

A sample was taken of the purified VLPs suspension for the first centrifuged cell lysate and analyzed by SDS PAGE: sample in Lane 6, FIG. 14. The product obtained contained VLPs with purity of about 88%. Protein concentration (Pierce® BCA Protein Assay Kit, Thermo Fisher Scientific, Rockford, Ill.) of this sample was 18.5 mg/mL. Optical density measured in a 1 cm cell at 260 nm (OD-260 nm) of a 200:1 dilution of this sample was 0.553 and OD-280 nm was 0.303. These measurements are consistent with RNA yield of about 9 mg per liter of culture.

A sample was taken of the purified VLPs suspension for the second centrifuged cell lysate and analyzed by SDS PAGE: sample in Lane 7, FIG. 14. The product obtained contained VLPs with purity of about 75%. Protein concentration of this sample was 25.4 mg/mL. OD-260 nm of a 200:1 dilution of this sample was 0.784 and OD-280 nm was 0.453. These measurements are consistent with RNA yield of about 11 mg per liter of culture.

A sample was taken of the purified VLPs suspension for the third centrifuged cell lysate and analyzed by SDS PAGE: sample in Lane 8, FIG. 14. The product obtained contained VLPs with purity of about 94.3%. Protein concentration of this sample was 21.0 mg/mL OD-260 nm of a 200:1 dilution of this sample was 0.632 and OD-280 nm was 0.321. These measurements are consistent with RNA yield of about 10 mg per liter of culture.

A sample was taken of the purified VLPs suspension for the fourth centrifuged cell lysate and analyzed by SDS PAGE: sample in Lane 9, FIG. 14. The product obtained contained VLPs with purity of about 95.6%. Protein concentration of this sample was 19.4 mg/mL. OD-260 nm of a 200:1 dilution of this sample was 0.666 and OD-280 nm was 0.353. These measurements are consistent with RNA yield of about 11 mg per liter of culture.

A sample was taken of the purified VLPs suspension for the fifth centrifuged cell lysate and analyzed by SDS PAGE: sample in Lane 10, FIG. 14. The product obtained contained VLPs with purity of about 96%. Protein concentration of this sample was 19.8 mg/mL. OD-260 nm of a 200:1 dilution of this sample was 0.661 and OD-280 nm was 0.354. These measurements are consistent with RNA yield of about 11 mg per liter of culture.

Example P

Isolation of RNA Encapsidated in the VLPs of Example O

Figure 15:
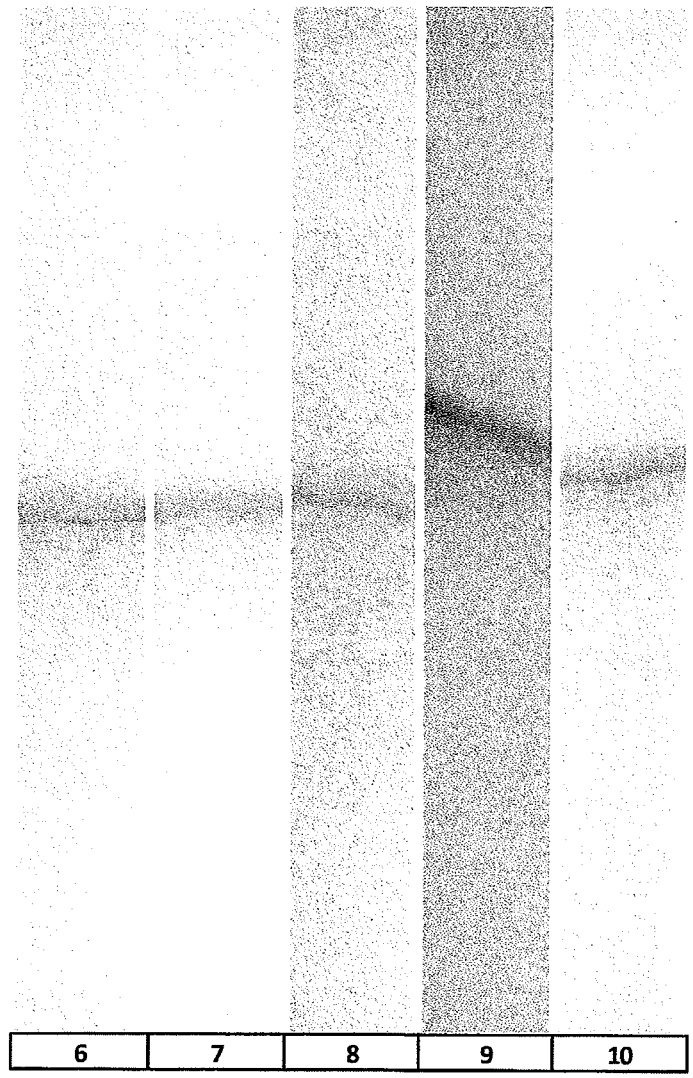
FIG. 15 is a gel showing results of PAGE analysis of RNA obtained from RNA encapsidated in the VLPs purified in FIG. 14.

RNA encapsidated in MS2 capsids purified as described in Example O was extracted from each experiment using TRIzol® reagent according to the protocol supplied by the manufacturer (Life Technologies, Grand Island, N.Y.). RNA obtained was denatured by heating for 5 min at 95° C. in formamide and analyzed by electrophoresis in 17.6 cm×38 cm×0.04 cm (W,L,T) gels composed of 8% polyacrylamide, 8 molar urea, 1.08% Tris base, 0.55% Boric acid, and 0.093% EDTA. The running buffer had the same concentrations of Tris base, Boric acid and EDTA as the gel. Power was delivered at about 40 W. Gels were stained using a 0.025% solution of Stains-All dye (Sigma-Aldrich, St. Louis, Mo.) in an aqueous mixture containing 25% formamide, 19% isopropanol and 15 mM Tris at pH 8. Results are shown in FIG. 15. Lane numbers for RNA electrophoresis in FIG. 15 refer to the same lane numbers for protein electrophoresis in FIG. 14. A single RNA band can be observed in each lane, consistent with high purity RNA recovered in each case, demonstrating that specific intact RNA molecules can be packaged into VLPs and efficiently purified from protease treated cell lysates.

Example Q

HDV Ribozyme Produced shRNA by In-Vitro Transcriptions

To test whether active RNA species, such as ribozymes can be effectively packaged in VLPs and purified by simple protease and precipitation treatment, a series of test constructs suitable for packaging by virtue of containing an MS2 packing sequence associated with ribozymes and shRNA were designed and tested in vitro. Ideally, an active RNA would be generated by cleavage of the active RNA from the packing sequence and any other sequences such as a spacers or transcription terminators by a ribozyme contained within the packaged RNA molecule itself. Constructs T7-Rz2 (SEQ ID NO: 5) and T7-Rz3 (SEQ ID NO: 6), representing such an arrangement, were produced by in vitro transcription and tested for their ability to produce a siRNA by self-cleavage. The DNA sequences of these constructs encode a T7 promoter followed by a Hammerhead ribozyme designed to cleave the 5' end of a shRNA hairpin (in T7-Rz3 but not in Tz-Rz2), the shRNA hairpin, Hepatitis Delta Virus (HDV) ribozyme designed to cleave the 3' end of the shRNA hairpin, an AT spacer, an MS2 specific RNA 19-mer encoding the packing sequence necessary for incorporation of the construct into a VLP, and an NcoI restriction site. T7-Rz3 and T7-Rz2 differ from one another only by the presence or absence of the 5' Hammerhead ribozyme, respectively.

Both of these constructs was cloned as BamHI-PacI restriction fragments into pMA (ampR) plasmids (Life Technologies). One Shot BL21/DE3 Chemically Competent *E. coli* (Life Technologies) cells were transformed using each plasmid. BL21(DE3) cells containing each plasmid were grown separately in LB medium containing ampicillin at 37° C., to OD (600 nm) equal to 0.8. Plasmids were isolated using QIAprep® Spin Miniprep Kit (Qiagen) following the manufacturer's instructions. NcoI (New England Biolabs) was used to cut the isolated plasmids at the restrictions site following the MS2 packing sequence. After digestion, linear DNA templates were purified by electrophoresis on 1.5% agarose gels and isolated using a PureLink™ Quick Gel Extraction Kit (Life Technologies) following manufacturer's instructions. Reverse transcription used the MAXIscript® T7 Kit per the manufacturer's instructions. RNA products were electrophoresed in 8% polyacrylamide gels containing 8M urea, 1.08% Tris base, 0.55% boric acid and 0.093% EDTA. Gels were 0.4 mm thick, 18 cm wide and 38 cm long. RNA bands were visualized using Stains-All (Sigma-Aldrich). Gel imaging and band quantification of was done using Image Lab 4.0.1 software (Bio-Rad).

Template T7-Rz2

The template has a total of 165 nt. The first 18 nucleotides in the sequence are the T7 promoter and the last 5 are removed on digestion with NcoI when the linear template is prepared. The full length transcript for T7-Rz2 is 165 nts–18 nts–5 nts=142 nts. The transcript starts at nucleotide 19 with the sequence 5'GCTTGT (this is the start of the shRNA). When the HDV ribozyme cuts, since the siRNA is 49 nucleotides long, the expected length of the second fragment is 93 nt.

Figure 16:
FIG. 16 is a gel showing the results of PAGE analysis of self cleavage of in vitro transcribed T7-Rz3 (lane 1) and T7-Rz2 (lane 3).

Results are shown in FIG. 16, Lane 3. The largest band (142 nts) is uncut transcript. The second band is the fragment containing the HDV ribozyme, the AT linker and the MS2 packing sequence (93 nts) and third band is the siRNA (49 nt).

Template T7-Rz3

The template had a total of 221 nucleotides (nts), in which the first 18 nucleotides are the T7 promoter. Transcription starts at nucleotide 19. Since digestion with Nco I removes the last 5 nucleotides of the template, the full length transcript is 221 nts–18 nts–5 nts=198 nts. The Hammerhead ribozyme (the first ribozyme from the 5' end of the transcript) was designed to cut between the 3rd and 4th nucleotides in the sequence 5'-GTCGCT-3', so the first fragment is expected to be 56 nucleotides long. The HDV ribozyme (the first ribozyme from the 3' end of the transcript) is designed to release the shRNA clone from the rest of the transcript, producing a 49 nucleotide long shRNA. So, if the full length transcript is 198 nucleotides and the first fragment (containing the excised Hammerhead ribozyme) is 56 nucleotides and the shRNA is 49 nucleotides, the third fragment consisting of the HDV ribozyme, the AT linker and MS2 packing sequence should be 93 nucleotides. This result is expected when both ribozymes cut. If only the Hammerhead ribozyme cuts, the expected result is one fragment 56 nucleotides long and a second fragment 142 nucleotides long. If only the 3' HDV ribozyme cuts, the expected result is one fragment 104 nucleotides long and a second fragment 94 nucleotides long.

Results are shown in FIG. 16, Lane 1. The 5' Hammerhead ribozyme efficiently cut the transcript, but the 3' HDV ribozyme cut much less efficiently. The first band (198 nucleotides) is the uncut transcript. The second band (142 nucleotides) is the transcript fragment containing the siRNA, 3' HDV ribozyme, the AT linker and the MS2 packing sequence. The 5' Hammerhead ribozyme fragment (56 nt) is present but did not stain well.

These results indicate that the 5' Hammerhead ribozyme in the T7-Rz3 construct cuts the template as expected, however the 3' HDV ribozyme within the T7-Rz3 transcript was not active, or only poorly active relative to the Hammerhead ribozyme. In contrast, in the absence of the 5' Hammerhead ribozyme, the HDV ribozyme present in the T7-Rz2 construct did produce a properly excised siRNA fragment. Thus, the basic design of T7-Rz2 is capable of producing siRNA from a larger RNA molecule bearing a packing sequence. The presence of the packing sequence in such a transcript means the construct may be efficiently packaged and purified in VLPs as described in the previous Examples.

Example R

Production of MS2 Capsids Encapsidating shRNA Targeting Green Fluorescent Protein (GFP) and HDV Ribozyme Attached to MS2 19-Mer RNA Hairpin To test whether an active RNA similar to those described in Example Q is actually packaged into a VLP in vivo the following experiment was carried out.

Construct T7-Rz6 (SEQ ID NO: 7) encoding a BamHI restriction site, a T7 promoter driving expression of an shRNA hairpin targeted against GFP, followed by a Hepatitis Delta Virus (HDV) ribozyme designed to cleave the 3' end of the siRNA hairpin, and an MS2 specific RNA 19-mer encoding the packing sequence necessary for incorporating the construct into a VLP followed by an NcoI restriction site was cloned as a BamHI-Bsp19I restriction fragment into plasmid pACYC184.

Capsid protein required for production of MS2 capsids is expressed from a plasmid comprising DNA sequence (SEQ ID NO: 2), encoding the MS2 capsid protein gene cloned into pDEST14 via Gateway recombination methods (Life Technologies).

One Shot BL21/DE3 Chemically Competent E. coli (Life Technologies) cells were transformed with the 2 plasmids selecting for chloramphenicol and ampicillin resistant transformants. For VLP production these transformants were grown at 37° C. in 32 mL LB medium containing both ampicillin and chloramphenicol. When the culture density reached an OD (600 nm) of 0.8, IPTG (Sigma-Aldrich) was then added to a final concentration of 1 mM. Cells were harvested 4 hours post-induction by centrifugation at 3,000 g and 4° C. for 40 min. RNA was extracted from purified VLPs as described in Example P, and analyzed as described in Example Q. A band of the same molecular weight as expected for the encoded shRNA, as observed in lane shRNA in FIG. 17, was observed.

Figure 17:
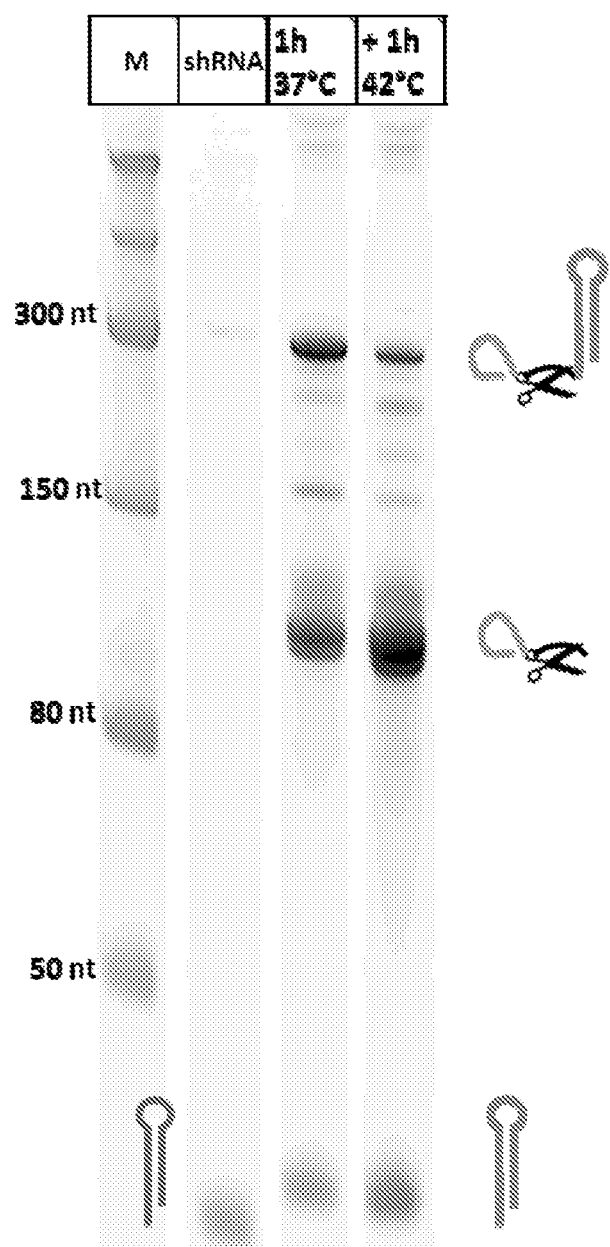
FIG. 17 is a gel showing results of PAGE analysis of shRNA products obtained during in vitro transcriptions using HDV ribozymes flanked by shRNA and an MS2 packing sequence. Lane 1 is RNA size marker. Lane 2 is an shRNA control. Samples in lanes 3 and 4 are the RNAs produced by in vitro transcription. The sample in Lane 3 was incubated for one hour at 37° C. and placed on ice for an additional hour before electrophoresis. The sample in lane 4 was incubated at 37° C. and then incubated at 42° C. for an additional hour prior to gel electrophoresis.

The intact packaged T7-Rz6 transcript is about 150 bases long. The cleaved molecule is designed to produce two fragments, one of approximately 100 bases comprising the ribozyme and packing sequences and the other the intact shRNA of about 50 bases. FIG. 17 illustrates that the uncut RNA molecule appears to be almost 300 bases in length. However, there is considerable potential secondary structure in this molecule, and the higher apparent molecular weight is likely due to such structures.

Example S

Production of Transcripts Coding for shRNA and Long Hammerhead Ribozymes Attached to MS2 19-Mer RNA Hairpin Several experiments producing MS2 capsids, each encapsidating different cargoes, are conducted as described in Example O. The intent of these experiments is to determine whether modified Hammerhead ribozymes can be modified to effectively cleave cargo molecules, unlike the Hammerhead ribozyme of T7-Rz3 in Example Q. Results (not shown) indicate that improving the thermodynamic stability of the properly folded ribozyme relative to the folding of the shRNA target improves the efficacy of ribozyme cleavage. One potential way to improve ribozyme stability is to increase the region of the ribozyme that hybridizes to the target portion of the cargo molecule, such constructs are referred to as long Hammerheads. Exemplary sequences of long Hammerhead ribozymes are presented in subsequent Examples.

Example T

Production of MS2 Capsids Containing a Transcript Coding for the Two Strands of an siRNA Targeting GFP Each Flanked by a Long Hammerhead Ribozyme Located at their 5' Ends and HDV Ribozymes at their 3' Ends, Attached to MS2 19-Mer RNA Hairpin The MS2 capsid can contain RNA molecules at least as long as 3,600 bases, the size of the MS2 bacteriophage genome. Thus, much longer heterologous cargo molecules can be packaged provided they contain the packing sequence necessary for encapsidation. The previous Examples described here indicate that active RNAs containing a combination of a shRNA hairpin and ribozymes designed to precisely cut the shRNA sequence free from the overall cargo molecule can be produced from a single short RNA transcript. This experiment tests whether the individual strands of siRNA can be independently cleaved from a single transcript by multiple specific ribozymes.

MS2 capsids are produced in vivo from a plasmid encoding MS2's capsid protein cloned into pDEST14 (Life Technologies) plasmid:

DNA sequence T7-Rz8 (SEQ ID NO: 8) encodes a BamHI restriction site, followed by a T7 promoter followed by Hammerhead ribozyme designed to cleave the 5' end of the sense strand of an siRNA targeted against EFGP (where EGFP is Enhanced Green Fluorescent Protein), followed by the sense strand of an siRNA targeted against EGFP, followed by an HDV ribozyme designed to cleave the 3' end of the sense strand of the siRNA, followed by an AT spacer and then a Hammerhead ribozyme designed to cleave the 5' side of the antisense strand of an siRNA targeted against EGFP, followed by the antisense strand of the siRNA, followed by an HDV ribozyme designed to cleave the 3' side of the antisense siRNA, followed by a 7 base spacer and the MS2 packing sequence and an NcoI restriction site. T7-Rz8 was cloned into plasmid pACYC184 as a BamHI-NcoI restriction fragment and a transcription terminator subsequently inserted at the 3' end of T7-Rz8.

One Shot BL21/DE3 Chemically Competent E. coli (Life Technologies) cells were transformed with the 2 plasmids, the one expressing the capsid protein and the other containing T7-Rz8 and selecting for chloramphenicol and ampicillin resistant transformants. For capsid production these transformants were grown at 37° C. in 750 mL LB medium containing both ampicillin and chloramphenicol. When the culture density reaches an OD (600 nm) of 0.8, IPTG (Sigma-Aldrich) was added to a final concentration of 1 mM. Cells were harvested 4 hours post-induction by centrifugation at 3,000 g and kept at 4° C. for 40 min. The cells are lysed and VLPs recovered by the procedures described in previous Examples and the RNA analyzed as in Examples Q and R. Such analysis indicates the active RNA is produced from the packaged RNA efficiently by combinations of long Hammerhead and HDV ribozymes.

Example U

Long Flanking Hammerhead Ribozymes Cut to a Significantly Higher Extent During in-Vitro Transcriptions than Short Flanking Hammerhead Ribozymes Constructs T7-Rz1 (SEQ ID NO: 9) and T7-Rz4 (SEQ ID NO: 10) were used as templates for in-vitro transcription.

T7-Rz1 comprises common ribozymes, i.e., with stems hybridizing the siRNA target of less than 6 hybridizing nucleotides. T7-Rz4 comprises flanking ribozymes with long-length stems that hybridize the siRNA being cut, i.e. stems with more than 6 hybridizing nucleotides.

Figure 18:
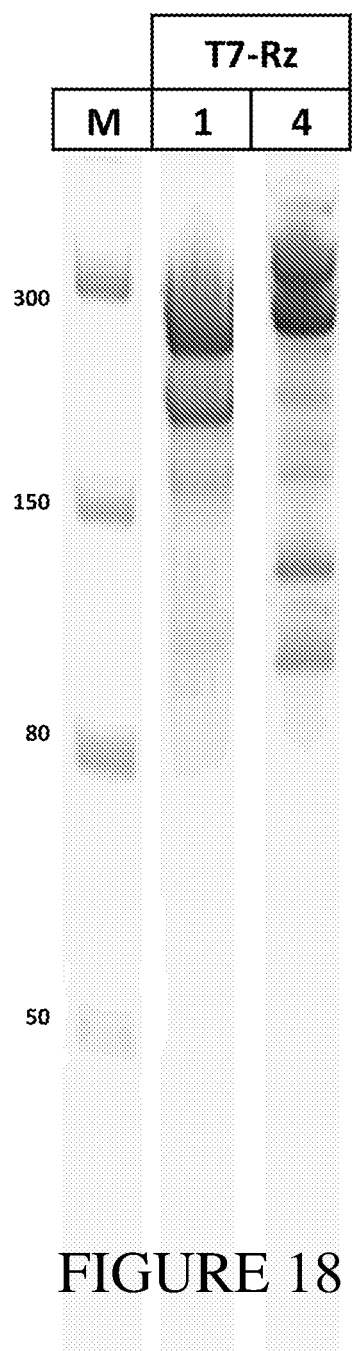
FIG. 18 is a gel showing results of PAGE analysis of in vitro RNA products obtained from T7-Rz1 and T7-Rz4 RNA.

Construct T7-Rz1 encodes a T7 promoter, a Hammerhead (HH) ribozyme designed to cleave the 5' end of a siRNA hairpin with 5 nucleotides complementary to the siRNA target, an siRNA hairpin, a HH ribozyme designed to cleave the 3' end of the siRNA hairpin with 5 nucleotides complementary to the siRNA target, and an NcoI restriction site:

Construct T7-Rz4 encodes a T7 promoter, a HH ribozyme designed to cleave the 5' end of a siRNA hairpin with 12 nucleotides complimentary to the siRNA target, an siRNA hairpin, a HH ribozyme designed to cut its 3' end of the siRNA hairpin with 23 nucleotides complimentary to the siRNA target:

In-vitro transcription experiments and analyses were run with these constructs in a similar manner to those described in Example Q. As shown in FIG. 18, results obtained with construct T7-Rz1 were consistent with the observation that ribozymes with short complimentary sequences cut poorly, whereas the results obtained with construct T7-Rz4 are consistent with the hypothesis that ribozymes with longer complimentary sequences cut the target more effectively.

Example V

Production of VLPs Using a Transcript Coding for shRNA Against EGFP Flanked by a Long Hammerhead Ribozyme at its 5' End and Another Long Hammerhead Ribozyme Attached to MS2 19-Mer RNA Hairpin at its 3 End Production of MS2 capsids was conducted as follows. SEQ ID NO: 2, encoding MS2 capsid protein was cloned into pDEST14 (Life Technologies) plasmid:

The DNA sequence for T7-Rz4 was cloned into plasmid pACYC184 as a BamHI-HindIII fragment. A transcription terminator was subsequently cloned at the 3' end of construct T7-Rz4.

One Shot BL21/DE3 Chemically Competent *E. coli* (Life Technologies) cells were transformed with the 2 plasmids, the one capable of expressing capsid protein and the other containing T7-Rz4 and selecting for chloramphenicol and ampicillin resistant transformants. For VLP production these transformants were grown at 37° C. in 750 mL LB medium containing both ampicillin and chloramphenicol. When the culture density reached OD (600 nm) 0.8, IPTG (Sigma-Aldrich) was added to a final concentration of 1 mM. Cells were harvested 4 hours post-induction by centrifugation at 3,000 g and 4° C. for 40 min. A sample was taken prior to induction and at the time of harvest for analysis. Samples were lysed and the VLPs were purified as described in Example 0.

Figure 19:
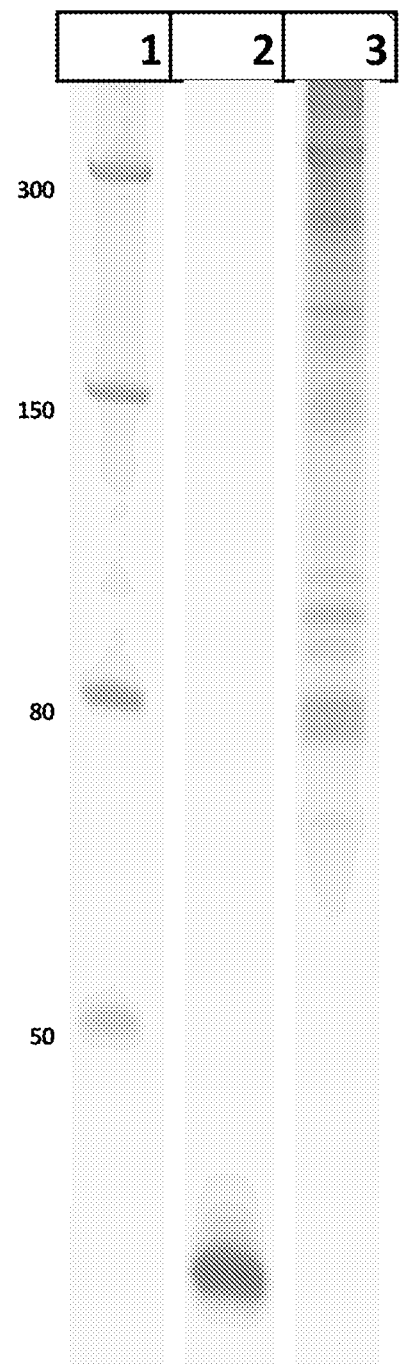
FIG. 19 is a gel showing in vivo transcribed and packaged T7-Rz4 RNA. Lane 1 is a set of molecular standards. Lane 2 shows a chemically synthesized shRNA 49 nucleotides long and Lane 3 is the RNA recovered from VLPs

RNA encapsidated in the purified VLPs was extracted using TRIzol® reagent according to the protocol supplied by the manufacturer (Life Technologies, Grand Island, N.Y.). RNA obtained was denatured by heating for 5 min at 95° C. in formamide and analyzed by electrophoresis in Novex® denaturing 15% polyacrylamide TBE-Urea gels (Life Technologies) run at 70° C. RNA bands were visualized using 0.5 µg of Ethidium Bromide (Sigma-Aldrich, St. Louis, Mo.) per mL of aqueous solution. Results obtained are shown in FIG. 19. Lane 1 is a set of molecular standards. Lane 2 shows a chemically synthesized shRNA 49 nucleotides long and Lane 3 is the RNA recovered from the VLPs.

Example W

VLPs Comprising MS2 Capsids Obtained in Example V are Resistant to Protease from *Engyodontium Album, Bacillus Licheniformis*, Pepsin from Porcine Gastric Mucosa, and Papain from *Papaya* Latex VLPs comprising MS2 Capsids obtained from 250 mL of culture and purified as described in Example V were suspended in 400 µL 20 mM CaCl$_2$ aqueous solution at pH 7.5.

Figure 20:
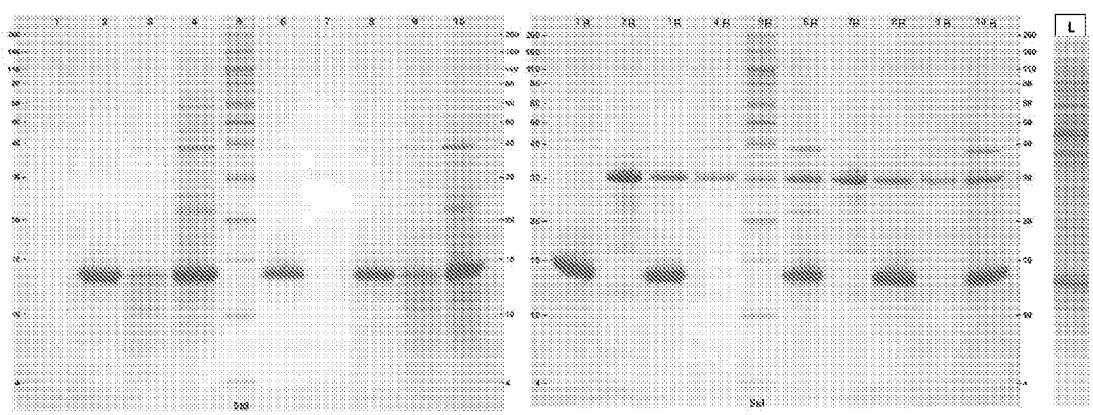
FIG. 20 is a series of gels showing results of SDS-PAGE analyses of RNA products obtained from RNA encapsidated in VLPs, following purification of the VLPs and isolation of the RNA from the VLP.

A 66 µL aliquote of this suspension was diluted to 0.25 mL with 20 mM CaCl$_2$ aqueous solution at pH 7.5 and incubated at 37° C. Samples were taken for protein concentration (Pierce® BCA Protein Assay Kit, Thermo Fisher Scientific, Rockford, Ill.) and SDS PAGE analyses after 1 hour, and 4 hours of incubation. Protein concentration in these 2 samples was 3086, and 4656 mg/L respectively. SDS PAGE analyses are shown in FIG. 20, Lanes 1B, and 6 respectively. The same amount of protein was loaded in each lane (4 µg). This set of experiments was used as a negative control.

2 µg Protease from *Streptomyces griseus* (Sigma Aldrich, St. Louis, Mo.) was diluted to 0.25 mL with 20 mM CaCl$_2$ aqueous solution at pH 7.5 and incubated at 37° C. Samples were taken for protein concentration and SDS PAGE analyses after 1 hour, and 4 hours of incubation. Protein concentration in these 2 samples was 361, and 324 mg/L respectively. SDS PAGE analyses are shown in FIG. 20, Lanes 1, and 7 respectively. The same amount of protein was loaded in each lane (4 µg). This set of experiments was used as another negative control.

2 µg of Protease from *Streptomyces griseus* was added to another 66 µL aliquote of the VLPs comprising MS2 capsids suspension, diluted to 0.25 mL with 20 mM CaCl$_2$ aqueous solution at pH 7.5 and incubated at 37° C. Samples were taken for protein concentration and SDS PAGE analyses after 1 hour, and 4 hours of incubation. Protein concentration in these 2 samples was 2940, and 3012 mg/L respectively. SDS PAGE analyses are shown in FIG. 20, Lanes 2, and 8, respectively. The same amount of protein was loaded in each lane (4 µg). This set of experiments was used to test the proteolytic stability towards Protease from *Streptomyces griseus* of MS2 capsids forming the VLPs. Less than 10% degradation was observed.

Another 66 µL aliquote of the VLPs comprising MS2 Capsids suspension, diluted to 0.25 mL with 20 mM CaCl$_2$ aqueous solution at pH 7.5 was subjected to three cycles of heating to 95° C. for 10 minutes and cooling on wet ice for 10 min to achieve the disassembly of the VLPs. 2 µg of Protease from *Streptomyces griseus* was then added to this suspension and was incubated at 37° C. Samples were taken for protein concentration and SDS PAGE analyses after 1 hour, and 4 hours of incubation. Protein concentration in these 2 samples was 2601, and 3033 mg/L respectively. SDS PAGE analyses are shown in FIG. 20, Lanes 3, and 9 respectively. The same amount of protein was loaded in each lane (4 µg). Disassembled particles were degraded to a significant extent by Protease from *Streptomyces griseus*. This set of experiments was used as a positive control.

2 µg of Protease from *Streptomyces griseus* dissolved in 0.002 mL of 20 mM CaCl$_2$ aqueous solution at pH 7.5 was added to 0.248 mL of bacterial cell lysate obtained from 41 mL of cell culture from Example V and incubated at 37° C.

Samples were taken for protein concentration and SDS PAGE analyses after 1 hour, and 4 hours of incubation. Protein concentration in these 2 samples was 3192, and 4837 mg/L respectively. SDS PAGE analyses are shown in FIG. 20, Lanes 4, and 10 respectively. The last lane of FIG. 20, labeled L, shows untreated bacterial cell lysate. The same amount of protein was loaded in each lane (4 µg). More than 90% of proteins other than MS2 capsid protein were degraded by Protease from *Streptomyces griseus*. This set of experiments was used as another positive control.

This set of five experiments demonstrates that MS2 capsids forming the VLPs of this disclosure are resistant to proteolysis by Protease from *Streptomyces griseus*.

2 µg Protease from *Bacillus licheniformis* (Sigma Aldrich, St. Louis, Mo.) was diluted to 0.25 mL with 10 mM Na acetate and 5 mM Ca acetate aqueous solution at pH 7.5 and incubated at 37° C. Samples were taken for protein concentration and SDS PAGE analyses after 1 hour, and 4 hours of incubation. Protein concentration in these 2 samples was 976, and 1003 mg/L respectively. SDS PAGE analyses are shown in FIG. 20, Lanes 2B, and 7B respectively. The same amount of protein was loaded in each lane (4 µg). This set of experiments was used as another negative control.

2 µg of Protease from *Bacillus licheniformis* was added to another 66 µL aliquote of the VLPs comprising MS2 Capsids suspension, diluted to 0.25 mL with 10 mM Na acetate and 5 mM Ca acetate aqueous solution at pH 7.5 and incubated at 37° C. Samples were taken for protein concentration and SDS PAGE analyses after 1 hour, and 4 hours of incubation. Protein concentration in these 2 samples was 3144, and 3727 mg/L respectively. SDS PAGE analyses are shown in FIG. 20, Lanes 3B, and 8B respectively. The same amount of protein was loaded in each lane (4 µg). This set of experiments was used to test the proteolytic stability towards Protease from *Bacillus licheniformis* of MS2 capsids forming the VLPs. Less than 10% degradation was observed.

Another 66 µL aliquote of the VLPs comprising MS2 Capsids suspension, diluted to 0.25 mL with 10 mM Na acetate and 5 mM Ca acetate aqueous solution at pH 7.5 was subjected to three cycles of heating to 95° C. for 10 minutes and cooling on wet ice for 10 min to disassemble of the VLPs. 2 µg of Protease from *Bacillus licheniformis* was then added to this suspension and was incubated at 37° C. Samples were taken for protein concentration and SDS PAGE analyses after 1 hour, and 4 hours of incubation. Protein concentration in these 2 samples was 1769, and 1785 mg/L respectively. SDS PAGE analyses are shown in FIG. 20, Lanes 4B, and 9B respectively. The same amount of protein was loaded in each lane (4 µg). Disassembled particles were degraded by Protease from *Bacillus licheniformis*. This set of experiments was used as a positive control.

2 µg of Protease from *Bacillus licheniformis* dissolved in 0.002 mL of 10 mM Na acetate and 5 mM Ca acetate aqueous solution at pH 7.5 was added to 0.248 mL of bacterial cell lysate obtained from 41 mL of cell culture from example CC and incubated at 37° C. Samples were taken for protein concentration and SDS PAGE analyses after 1 hour, and 4 hours of incubation. Protein concentration in these 2 samples was 3696, and 4078 mg/L respectively. SDS PAGE analyses are shown in FIG. 20, Lanes 6B, and 10B respectively. The last lane of FIG. 21, labeled L shows untreated bacterial cell lysate. The same amount of protein was loaded in each lane (4 µg). More than 90% of proteins other than MS2 capsid protein were degraded by Protease from *Bacillus licheniformis*. This set of experiments was used as another positive control.

This set of four experiments demonstrated that MS2 capsids forming the VLPs of this disclosure are resistant to proteolysis by Protease from *Bacillus licheniformis*.

Three additional sets of equivalent experiments demonstrated that MS2 capsids forming the VLPs of this disclosure are resistant to proteolysis by any of the following three proteases: Proteinase K from *Engyodontium album*, Pepsin from porcine gastric mucosa (CAS Number 9001-75-6), and Papain from *papaya* latex (CAS Number 9001-73-4) (all sourced from Sigma-Aldrich, St. Louis, Mo.). Each protease was used according the manufacturer's instructions. Proteinase K was used at pH 7.5, Pepsin was used at pH 1.6, and Papain was used at pH 6.6.

Example X

Compositions with Long RNA

The ability to package long single strand RNA molecules, up to about 3,600 nucleotides in an MS2 capsid, potentially provides a simple and efficient method for producing double stranded RNA molecules such as miRNA, or substrates for RNA processing systems such as CRISPR (in bacteria), DICER (in animals) or by Dicer-like proteins (in plants). In one method, each strand of the desired long double stranded RNA molecule is produced as a transcript containing a packing sequence and a ribozyme designed to cut the long strand at a precise point, to separate the desired RNA sequence from the packing and ribozyme sequences. In another method, no ribozyme is required and the complimentary sequences remain attached to the packing sequence. By the methods described in these Examples each strand can be separately packaged and purified and equal molar amounts of each purified VLP containing one of the strands mixed together and the single stranded RNA from each VLP recovered and annealed to form the desired double-stranded RNA. In one method, the ribozyme of each RNA molecule is specific to its own strand and therefore cleaves only its cognate target. The long complimentary RNA strands are allowed to anneal and recovered from the mixture by physical methods or by treatment with RNAse A, which preferentially degrades single stranded RNAs such as the ribozyme and packing sequences. In the case of RNA molecules without ribozymes, the packing sequences will remain single stranded after the long complimentary sequences have annealed and may be removed by treatment with RNAse A.

To demonstrate, a DNA insert (SEQ ID NO: 11) coding for a BamHI restriction site, followed by a T7 polymerase promoter driving expression of a long sense strand RNA designed to produce siRNA targeted against arginine kinase of *Anasa tristis* (commonly known as squash bug, a major agricultural insect pest), followed by a high affinity MS2 packing sequence and T7 terminator is cloned into pACYC184.

Similarly, a DNA insert (SEQ ID NO: 12) coding for a T7 polymerase promoter driving expression of a long anti-sense strand RNA designed to produce siRNA targeted against arginine kinase of *Anasa tristis*, followed by a high affinity MS2 packing sequence and T7 terminator is also cloned into pACYC184.

Each plasmid is separately transformed into *E. coli* strain BL21/DE3 containing a plasmid expressing the MS2 capsid protein from the T7 promoter of pDEST14 and cultures of each are grown, T7 polymerase is induced by IPTG, the cells are incubated for an additional period and the VLPs recovered as described in previous Examples. Equal amounts of VLPs from each preparation are combined and the RNA cargo molecules recovered as described in Example P.

The sense and anti-sense RNA molecules are heated to a temperature approximately equal or higher than the calculated melting temperature of the desired double stranded RNA. The aqueous mixture is then cooled by 10° C. Additional cycles of heating and cooling to the same temperatures are conducted, to achieve a more complete hybridization between sense and antisense strands. The double stranded RNA can be treated with RNAse A which preferentially degrades single stranded RNA to remove the unannealed packing sequences and any ribozyme sequence that may be present.

In a test experiment aimed at killing insects using such a method a control VLP is designed in which a random RNA sequence was used in a control experiment. In a test experiment at least 10 insects are injected with the arginine kinase directed RNA and in a control experiment the same number of insects are injected with the random RNA. Seven (7) days after injection, a significantly higher number of insects die in the test experiment than in the control experiment.

Example Y

Compositions with Long Bulged RNA

Although the MS2 capsid is capable of encapsidating about 3,600 nucleotides of single stranded RNA, the ability to directly encapsidate double stranded RNA is highly constrained since such RNAs have a relatively rigid axis along the double stranded helix and helixes that exceed the interior diameter of the capsid cannot be efficiently packed. However, by strategically placing mismatches (bulges) along the length of complimentary sequence, double stranded RNA of lengths longer than the interior diameter of the capsid can be packed.

To demonstrate this, pACYC184 containing DNA with SEQ ID NO: 13 was constructed. SEQ ID NO: 13 encodes a T7 promoter driving expression of a DNA template encoding variants of the long sense and anti-sense strands of the arginine kinase directed siRNA precursors of Example X, arranged in such a way that they are separated by a non-complimentary sequence of 25 bases to allow the molecule to loop onto itself so that sense and complimentary antisense sequences may anneal to each other. The construct also includes a packing sequence, located at the 5' end of the transcribed sequence and an HDV ribozyme capable of cleaving the template to remove itself and the downstream terminator sequences. Since the antisense strand of the annealed molecule is the active agent for siRNA inhibition of the targeted host arginine kinase messenger RNA, the sense strand is modified so that 1 to 3 consecutive nucleotides every 19 to 28 nucleotides are added to the sense RNA strand so that they are no longer perfectly complimentary to the antisense sequence. Such bulged regions appear to impart sufficient flexibility to the overall structure that the entire RNA transcript can be packaged within a capsid. Further, the double stranded (bulged) RNA is more resistant to degradation by RNAse A than single stranded RNA. Importantly, a similar construct lacking the 1 to 3 base mismatches every 19 to 28 bases will not package efficiently.

The plasmid is transformed into *E. coli* strain BL21/DE3 containing a plasmid expressing the MS2 capsid protein from the T7 promoter of pDEST14 and cultures are grown to a suitable density, T7 polymerase is induced by IPTG, the cells are incubated for an additional period and the VLPs recovered as described in previous Examples. RNA is extracted from the VLPs as described in Example P.

The RNA molecules are heated to a temperature approximately equal to or higher than the calculated melting temperature of the desired double stranded region of the RNA. The aqueous mixture is then cooled by 10° C. Additional cycles of heating and cooling to the same temperatures may be conducted, to achieve a more complete hybridization between sense and antisense strands. The bulged double stranded RNA can be treated with RNAse A which preferentially degrades single stranded RNA to remove the unannealed packing sequences and any ribozyme sequence that may be present.

In a test experiment aimed at killing insects using such a method a control VLP was designed in which a random complimentary bulged RNA sequence was used in a control experiment. In a test experiment at least 10 insects are injected with the arginine kinase directed bulged RNA and in a control experiment the same number of insects are injected with the random bulged RNA. Seven (7) days after injection, a significantly higher number of insects die in the test experiment than in the control experiment.

Example Z

Compositions with Multiple shRNAs

The following RNA strand was expressed: 5'-PAC-shRNA-ribozyme-3', where PAC is the high affinity MS2 packing sequence and shRNA is sense RNA-loop-antisense RNA. Sense RNA is an RNA strand composed of 19 to 24 nts with the same sequence as a section of an endogenous RNA strand targeted for cleavage via RNAi. Antisense RNA is an RNA strand composed of 21 to 26 nts with a sequence consisting of the reverse complement of a section of an endogenous RNA strand targeted for cleavage. The resulting RNA is packed into MS2 capsids to form a VLP.

In some instances antisense RNA strands are designed to target, via RNAi, endogenous RNA strands essential for the survival of the host taking up such RNAs within VLPs. For example, in one instance, antisense RNA 21 nucleotides long is designed to target a section of *Anasa tristis* arginine kinase mRNA in a test experiment aimed at killing such insects using such test VLP. A control VLP experiment is performed in which an RNA 21 nucleotides long of random sequence is used. In a test experiment more than 10 insects are injected with the test VLP. In a control experiment the same number of insects are injected with the control VLP. Seven days after injection, a significantly higher number of insects die in the test experiment than in the control experiment.

The DNA insert coding for the transcript described here (SEQ ID NO: 14) includes a high affinity MS2 packing sequence followed by the sense strand siRNA, a loop, the anti-sense strand siRNA and an HDV ribozyme:

Another embodiment of such an RNA construct (SEQ ID NO: 15) includes a high affinity MS2 packing sequence followed by an AT spacer, the sense strand siRNA targeted against a first host mRNA sequence, a loop, the antisense strand siRNA targeted against the first host mRNA sequence, a second AT spacer, another sense strand siRNA targeted against a second host mRNA sequence, a loop, the antisense siRNA targeted against the second host mRNA sequence, another AT spacer and an HDV ribozyme. It is apparent to one skilled in the art that the targeted first and second host mRNA sequences can be sequences specific to different portions of the same mRNA, or to portions of different mRNAs, or even to mRNAs from different organisms. In the first instance, the first and second siRNAs may be targeted to different sequences of a single transcribed gene within a single species such as *Anasa tristis* arginine kinase. Alternatively, the first and second siRNAs may be targeted to separate transcribed genes in a single species such as targeting the first siRNA to *Anasa tristis* arginine kinase and the second siRNA to *Anasa tristis* chitin synthase. Similarly, the first siRNA may target *Anasa tristis* arginine kinase (or chitin synthase, or some other essential gene) while the second siRNA targets the same gene in a different host such as, for example, *Acyrthosiphon pisum*. Finally, the first and second siRNAs may target different essential host genes in different hosts. Each of these compositions can be extended to encompass many multiples of siRNAs by chaining together many copies of the AT spacer-sense strand siRNA-loop-antisense strand siRNA-ribozyme motif and used to control one or more species of insect pests with a single VLP preparation.

Example AA

Compositions with Half-Looped shRNA

In some instances a significant improvement in packing yield is obtained by expressing and packing RNA templates containing multiple MS2 packing sequences. An example of such a construct, SEQ ID NO: 16 includes an MS2 packing sequence followed by a sense strand siRNA sequence followed by a short “half loop” sequence, followed by a second MS2 packing sequence followed by another “half loop” followed by the antisense siRNA sequence. In this arrangement cleavage of the “half loop” and the MS2 packing sequences are removed by DICER or other processing systems within the targeted host organism.

In some instances antisense RNA strands are designed to target, via RNAi, endogenous RNA strands essential for the survival of the host taking up a VLP containing such an RNA. For example, in one instance, an antisense RNA 21 bases long is designed to target a section of *Anasa tristis* arginine kinase mRNA in a test experiment aimed at killing such insect using such a test VLP. A control VLP is designed in which a mock antisense RNA 21 bases long of random RNA sequence is used in a control experiment. In a test experiment more than 10 insects are injected with such test VLP. In a control experiment the same number of insects is injected with such control VLP. 7 days after injection, a significantly higher number of insects die in the test experiment than in the control experiment.

Example AB

Compositions with Bulged and Half-Looped shRNA

One skilled in the art will recognize that the arrangements described herein are not mutually exclusive and may be combined in various configurations. For example a bulged configuration of the long double stranded RNAs described in Example Y may be combined with the multiple MS2 packing sequences and/or the half-loop configuration described in Examples Z and AA. Such configurations may or may not include ribozymes or they may rely solely on host functions such as CRISPR or DICER to process the cargo molecule. The unifying feature of such compositions is that they may be produced and packaged into VLPs in vivo and easily purified by treating cell lysates with proteases and other enzymes such as amylases, lipases and nuclease to allow simple filtration or precipitation to purify the VLPs containing the RNAs described here.

Example AC

Use of VLPs for Protein Expression

The previous Examples have focused on compositions and methods for silencing or reducing targeted host gene expression via various forms of RNAi. The following Examples disclose compositions and methods for increasing gene expression in a targeted host organism by efficient production of messenger RNAs using VLPs.

Protein Expression in Bacteria (*E. Coli*)

A construct designed for packing itself into MS2 capsids, and after transfection aimed at expressing EGFP in *E. coli* cells is depicted in SEQ ID NO: 17. This DNA construct includes a BamHI restriction site, a T7 promoter driving expression of a MS2 packing sequence variant followed by 10 bases of the MS2 replicase region in which the first C is changed to a G (to extend the stem) followed by the 5' end of the MS2 bacteriophage genome in which all but the first 9 bases of the maturase gene as well as the entire capsid protein have been replaced with the coding sequence of EGFP, followed by a 15 bases spacer, a second copy of the MS2 packing sequence and an HDV ribozyme designed to cleave at its own 5' end followed by a NotI restriction site. The DNA construct can be cloned via the BamHI and NotI sites into a compatible plasmid and transformed into an *E. coli* BL21/DE3 host cell already containing a plasmid capable of expressing MS2 capsid protein (as described in previous Examples). The cells are treated with IPTG to induce transcription by T7 polymerase and produce VLPs containing the 950 base transcript produced from SEQ ID NO: 17. The VLPs are purified by the methods described n Example 0.

When naïve strains of *E. coli* are exposed to such VLPs, uptake of the VLPs and subsequent translation of the cargo molecule containing the EGFP sequence can be detected by fluorescence due to the EGFP protein. Those skilled in the art will recognize that other genes of interest may be used in place of EGFP and that expression of these genes in any bacteria that takes up the VLPs containing them can be demonstrated by many methods such as Northern blot analysis or by detection of the proteins produced from such genes by Western blots or by an enzymatic or other activity specific to the protein encoded by the gene of interest. In bacteria that cannot directly take up MS2 capsid VLPs, the RNA cargo of the VLP can be isolated and separately transformed into the target bacteria by standard methods, well known in the art.

Example AD

Use of VLPs for Protein Expression in Plants

In a similar fashion, VLPs capable of directing gene expression in plants may be constructed based on engineering appropriate plant viruses to contain the gene of interest as well as one or more MS2 packing sequences.

Dicotyledonous Plants

In the case of dicotyledonous plants a construct incorporating features of the Carnation Italien ringspot virus can provide a platform for directing gene expression. Such a DNA construct is represented by SEQ ID NO. 18, which includes a BamHI restriction site followed by a T7 promoter driving expression of an MS2 packing sequence followed by 10 bases of the MS2 replicase region in which the first C is changed to a G (to extend the stem), followed by the first 77 bases of the Carnation Italian ringspot virus (GeneBank Accession No. NC_003500.2) containing the viral 5' adaptor, followed by the coding sequence of EGFP, followed by the last 351 bases of the viral genome (beginning at base 4410 of GeneBank Accesion No. NC_003500.2) encoding the 3' cap independent translational enhancer (3' CITE), followed by a 15 bases spacer a second copy of the MS2 packing sequence as well as an HDV ribozyme designed to cleave at its own 5' end, followed by a NotI restriction site. The DNA construct can be cloned via the BamHI and NotI sites into a compatible plasmid and transformed into an *E. coli* BL21/DE3 host cell already containing a plasmid capable of expressing MS2 capsid protein (as described in the previous examples). The transformed cells are treated with IPTG to induce transcription by T7 polymerase and produce VLPs containing the 1,236 base transcript generated from SEQ ID NO: 18. The VLPs are purified by the methods described n Example O.

When dicotyledonous plants are exposed to such VLPs uptake of the VLPs and subsequent translation of the cargo molecule containing the EGFP sequence can be detected by fluorescence due to the presence of the expressed EGFP protein. Those skilled in the art will recognize that other genes of interest may be used in place of EGFP and that expression of these genes in any dicotyledonous plant that takes up the VLPs containing them can be demonstrated by many methods, such as Northern blot analysis or by detection of the proteins produced from such genes by Western blots or by an enzymatic or other activity specific to the protein encoded by the gene of interest. In dicotyledonous plants that cannot directly take up MS2 capsid VLPs, the RNA cargo of the VLP can be isolated and separately transformed into the target plants by standard methods, well known in the art.

Monocotyledonous Plants

In the case of monocotyledonous plants a construct incorporating features of the Carnation Italien ringspot virus as well as the 3'-CITE of Maize necrotic streak virus can provide a platform for directing gene expression. Such a DNA construct is represented by SEQ ID NO: 19, which includes a BamHI restriction site followed by a T7 promoter driving expression of an MS2 packing sequence followed by 10 bases of the MS2 replicase region in which the first C is changed to a G (to extend the stem), followed by the first 77 bases of the Carnation Italian ringspot virus (GeneBank Accesion No. NC_003500.2) containing the viral 5' adapter, followed by the coding sequence of EGFP, followed by 112 bases of the 3'-CITE sequence of Maize necrotic streak virus (corresponding to bases 3892-4003 of GeneBank Accesion No. NC_007729.1 as described by Nicholson, et al. (2013) Journal of Virology 87(3):1872-83), followed by the last 87 bases of the Carnation Italian ringspot virus genome (bases 4674-4760 of GeneBank Accesion No. NC_003500.2), followed by a 15 bases spacer, a second copy of the MS2 packing sequence as well as an HDV ribozyme designed to cleave at its own 5' end, followed by a NotI restriction site. The DNA construct can be cloned via the BamHI and NotI sites into a compatible plasmid and transformed into an *E. coli* BL21/DE3 host cell already containing a plasmid capable of expressing MS2 capsid protein (as described in the previous examples). The transformed cells are treated with IPTG to induce transcription by T7 polymerase and produce VLPs containing the 1,084 base transcript generated from SEQ ID NO: 19. The VLPs are purified by the methods described n Example O.

When monocotyledonous plants are exposed to such VLPs uptake of the VLPs and subsequent translation of the cargo molecule containing the EGFP sequence can be detected by fluorescence due to the presence of the expressed EGFP protein. Those skilled in the art will recognize that other genes of interest may be used in place of EGFP and that expression of these genes in any monocotyledonous plant that takes up the VLPs containing them can be demonstrated by many methods, such as Northern blot analysis or by detection of the proteins produced from such genes by Western blots or by an enzymatic or other activity specific to the protein encoded by the gene of interest. In monocotyledonous plants that cannot directly take up MS2 capsid VLPs, the RNA cargo of the VLP can be isolated and separately transformed into the target plants by standard methods, well known in the art.

Example AE

Use of VLPs for Protein Expression in Mammals

VLPs capable of directing gene expression in mammals may be constructed based on engineering appropriate viruses to contain the gene of interest as well as one or more MS2 packing sequences.

In this example a construct incorporating features of Encephalomyocarditis virus (GeneBank Accesion No. M81861.1) and pRL-CMV (GeneBank Accesion No. AF025843.2) can provide a platform for directing gene expression. Such a DNA construct is represented by SEQ ID NO: 20, which includes a BamHI restriction site followed by a T7 promoter driving expression of an MS2 packing sequence variant followed by 10 bases of the MS2 replicase region in which the first C is changed to a G (to extend the stem), followed by 561 bases of Encephalomycarditis virus containing the viral IRES (described by Bochkov and Palmenberg (2006) BioTechniques 41:283-292) corresponding to bases 273-833 of GeneBank Accesion No. M81861.1) followed by EGFP and 248 bases of pRL-CMV encoding the SV40 late poly-A signal corresponding to bases 2004-2246 of GeneBank Accesion No. AF025843.2, followed by a 15 bases spacer a second copy of the MS2 packing sequence as well as an HDV ribozyme designed to cleave at its own 5' end, followed by a NotI restriction site. The DNA construct can be cloned via the BamHI and NotI sites into a compatible plasmid and transformed into an *E. coli* BL21/DE3 host cell already containing a plasmid capable of expressing MS2 capsid protein (as described in previous Examples). The transformed cells are treated with IPTG to induce transcription by T7 polymerase and produce VLPs containing the 1,612 base transcript generated from SEQ ID NO: 20. The VLPs are purified by the methods described n Example 0.

When mammalian cells are exposed to such VLPs uptake of the VLPs and subsequent translation of the cargo molecule containing the EGFP sequence can be detected by fluorescence due to the presence of the expressed EGFP protein. Those skilled in the art will recognize that other genes of interest may be used in place of EGFP and that expression of these genes in any mammalian cells that takes up the VLPs containing them can be demonstrated by many methods, such as Northern blot analysis or by detection of the proteins produced from such genes by Western blots or by an enzymatic or other activity specific to the protein encoded by the gene of interest. In mammalian cells that cannot directly take up MS2 capsid VLPs, the RNA cargo of the VLP can be isolated and separately transformed into the target cells by standard methods, well known in the art.

What is claimed is:

1. An oligoribonucleotide comprising a capsid specific packaging sequence and multiple complementary regions, wherein each of said complementary regions compromises:
   (a) a sense strand siRNA sequence, immediately followed by
   (b) a non-homolous RNA sequence capable of forming a loop, immediately followed by
   (c) an antisense strand siRNA sequence complementary to the sense strand siRNA sequence wherein the multiple complementary regions are contiguously arrayed.

2. The oligoribonucleotide of claim 1, wherein the complementary regions are linked by one or more ribozymes.

3. An oligoribonucleotide comprising a capsid specific packaging sequence and multiple complementary regions, wherein each of said complementary regions comprises:
   (a) multiple catenated sense strand siRNA sequences, immediately followed by
   (b) a non-homolous RNA sequence capable of forming a loop, immediately followed by
   (c) multiple catenated antisense strand siRNA sequences complementary to the multiple catenated sense strand siRNA sequences wherein the multiple complementary regions are contiguously arrayed.

4. The oligoribonucleotide of claim 3, wherein the multiple catenated sense strand siRNA sequences are linked by 1 to 3 non-complementary nucleotides to form bulged RNA.

5. The oligoribonucleotide of claim 1, wherein the RNA sequence capable of forming a loop comprises one or more ribozymes.

6. The oligoribonucleotide of claim 3, wherein the RNA sequence capable of forming a loop comprises one or more ribozymes.

* * * * *

```
                            SEQUENCE LISTING

<160> NUMBER OF SEQ ID NOS: 20

<210> SEQ ID NO 1
<211> LENGTH: 3569
<212> TYPE: RNA
<213> ORGANISM: Bacteriophage MS2

<400> SEQUENCE: 1 ggguggggacc ccuuucgggg uccugcucaa cuuccugucg agcuaaugcc auuuuuaaug    60
ucuuuagcga gacgcuacca uggcuaucgc uguaggguagc cggaauucca uuccuaggag   120
guuugaccug ugcgagcuuu uaguacccuu gauagggaga acgagaccuu cgucccaucc   180
guucgcguuu acgcggacgg ugagacugaa gauaacucau ucucuuuaaa auaucguucg   240
aacuggacuc ccggucguuu uaacucgacu ggggccaaaa cgaaacagug gcacuacccc   300
ucuccguauu cacgggggggc guuaguguuc acaucgauag aucaaggugc cuacaagcga   360 aguggggucau cgugggggucg cccguacgag gagaaagccg guuucggcuu cucccucgac   420
gcacgcuccu gcuacagccu cuucccugua agccaaaacu gacuuacau cgaagugccg    480 cagaacguug cgaaccgggc gucgaccgaa guccugcaaa aggucaccca ggguaauuuu   540
aaccuuggug uugcuuuagc agaggccagg ucgacagccu cacaacucgc gacgcaaacc   600
auugcgcucg ugaaggcgua cacugccgcu cgucgcggua auuggcgcca ggcgcuccgc   660
uaccuugccc uaaacgaaga ucgaaaguuu cgaucaaaac acguggccgg cagguggguu   720
gaguugcagu ucgguuagguu accacuaaug agugauaucc agggugcaua ugagaugcuu   780
acgaagguuc accuucaaga guuucuuccu augagagccg uacucaggu cgguacuaac   840 aucaaguuag auggccgucu gucguaucca gcugcaaacu uccagacaac gugcaacaua   900
ucgcgacgua ucgugauaug guuuuacaua aacgaugcac guuuggcaug guugucgucu    960
cuagguaucu ugaacccacu agguauagug ugggaaaagg ugccuuucuc auucguuguc   1020
gacuggcucc uaccuguagg uaacaugcuc gagggccuua cggcccccgu gggaugcucc   1080
uacaugucag gaacaguuac ugacguaaua acggugagu ccaucauaag cguugacgcu   1140
cccuacgggu ggacugugga gagacaggc acugcuaagg cccaaaucuc agccaugcau   1200 cgaggggguac aauccguaug gccaacaacu ggcgcguacg uaaagucucc uuucucgaug   1260
guccauaccu uagaugcguu agcauuaauc aggcaacggc ucucuagaua gagcccucaa   1320
ccggaguuug aagcauggcu ucuaacuuua cucaguucgu ucucgucgac aauggcggaa   1380
cuggcgacgu gacugucgcc ccaagcaacu ucgcuaacgg ggcgcugaa uggaucagcu   1440 cuaacucgcg uucacaggcu uacaaaguaa ccuguagcgu cgucagagc ucugcgcaga   1500 aucgcaaaua caccaucaaa gucgagguugc cuaaaguggc aacccagacu guggugggug   1560
uagagcuucc uguagccgca uggcguucgu acuuaaauau ggaacuaacc auuccauuu    1620 ucgcuacgaa uuccgacugc gagcuuauug uuaaggcaau gcaaggcucu cuaaaagaug   1680
gaaacccgau ucccucagca aucgcagcaa acuccggcau cacuaauag acgccggcca   1740 uucaaacaug aggauuaccc augucgaaga caacaaagaa guucaacucu uuauguauug   1800
aucuuccucg cgaucuuucu cucgaaauuu accaaucaau ugcuucuguc gcuacuggaa   1860
gcggugaucc gcacagugac gacuuuacag caauugcuua cuuaagggac gaauugcuca   1920
```

| | |
|---|---:|
| caaagcaucc gaccuuaggu ucugguaaug acgaggcgac ccgucguacc uuagcuaucg | 1980 |
| cuaagcuacg ggaggcgaau ggugaucgcg gucagauaaa uagagaaggu uucuuacaug | 2040 |
| acaaauccuu gucaugggau ccggauguuu acaaaccag caucgguagc cuuauuggca | 2100 |
| accuccucuc uggcuaccga ucgucguugu uugggcaaug cacguucucc aacggugcuc | 2160 |
| cuaugggca caaguugcag gaugcagcgc cuuacaagaa guucgcugaa caagcaaccg | 2220 |
| uuaccccccg cgcucugaga gcggcucuau uggccgaga ccaaugugcg ccguggauca | 2280 |
| gacacgcggu ccgcuauaac gagucauaug aauuuaggcu cguuguaggg aacggagugu | 2340 |
| uuacaguucc gaagaauaau aaaauagauc gggcugccug uaaggagccu gauaugaaua | 2400 |
| uguaccucca gaaagggguc ggugcuuuca ucagacgccg gcucaaaucc guugguauag | 2460 |
| accugaauga ucaaucgauc aaccagcguc uggcucagca gggcagcgua gaugguucgc | 2520 |
| uugcgacgau agacuuaucg ucugcauccg auuccaucuc cgaucgccug guguggaguu | 2580 |
| uucucccacc agagcuauau ucauaucucg aucguauccg cucacacuac ggaaucguag | 2640 |
| auggcgagac gauacgaugg gaacuauuuu ccacaauggg aaaugggguc acauuugagc | 2700 |
| uagaguccau gauauucugg gcaauaguca aagcgaccca aauccauuuu gguaacgccg | 2760 |
| gaaccauagg caucuacggg gacgauauua uaugucccag ugagauugca ccccgugugc | 2820 |
| uagaggcacu ugccuacuac gguuuaaac cgaaucuucg uaaaacguuc guuccgggc | 2880 |
| ucuuucgcga gagcugcggc gcgcacuuuu accguggugu cgaugucaaa ccguuuuaca | 2940 |
| ucaagaaacc uguugacaau cucuucgccc ugaugcugau auuaaaucgg cuacgggguu | 3000 |
| ggggaguugu cggagguaug ucagauccac gccucuauaa ggugugggua cggcucuccu | 3060 |
| cccaggugcc uucgauguuc uucggugggga cggaccucgc ugccgacuac uacguaguca | 3120 |
| gcccgccuac ggcagucucg guauacacca agacuccgua cgggcggcug cucgcggaua | 3180 |
| cccguaccuc ggguuuccgu cuugcucgua ucgcucgaga acgcaaguuc uucagcgaaa | 3240 |
| agcacgacag uggucgcuac auagcguggu uccauacugg aggugaaauc accgacagca | 3300 |
| ugaaguccgc cggcgugcgc guuauacgca cuucggagug gcuaacgccg guuccacau | 3360 |
| ucccucagga gugugggcca gcgagcucuc cucgguagcu gaccgaggga cccccguaaa | 3420 |
| cggggugggu gugcucgaaa gagcacgggu gcgaaagcgg uccggcucca ccgaaaggug | 3480 |
| ggcgggcuuc ggcccaggga ccuccccua aagagaggac ccgggauucu cccgauuugg | 3540 |
| uaacuagcug cuuggcuagu uaccaccca | 3569 |

<210> SEQ ID NO 2
<211> LENGTH: 393
<212> TYPE: DNA
<213> ORGANISM: Bacteriophage MS2

<400> SEQUENCE: 2

| | |
|---|---:|
| atggcttcta actttactca gttcgttctc gtcgacaatg gcggaactgg cgacgtgact | 60 |
| gtcgccccaa gcaacttcgc taacgggtc gctgaatgga tcagctctaa ctcgcgttca | 120 |
| caggcttaca agtaacctg tagcgttcgt cagagctctg cgcagaatcg caaatacacc | 180 |
| atcaaagtcg aggtgcctaa agtggcaacc cagactgttg gtggtgtaga gcttcctgta | 240 |
| gccgcatggc gttcgtactt aaatatggaa ctaaccattc caattttcgc tacgaattcc | 300 |
| gactgcgagc ttattgttaa ggcaatgcaa ggtctcctaa agatggaaa cccgattccc | 360 |
| tcagcaatcg cagcaaactc cggcatctac taa | 393 |

<210> SEQ ID NO 3
<211> LENGTH: 130
<212> TYPE: PRT
<213> ORGANISM: Bacteriophage MS2

<400> SEQUENCE: 3

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 4
<211> LENGTH: 480
<212> TYPE: DNA
<213> ORGANISM: Artificial Sequence
<220> FEATURE:
<223> OTHER INFORMATION: Bacteriophage MS2 coat protein and pac sequence
      cloning cassette
<220> FEATURE:
<221> NAME/KEY: gene
<222> LOCATION: (42)..(435)
<220> FEATURE:
<221> NAME/KEY: stem_loop
<222> LOCATION: (454)..(472)

<400> SEQUENCE: 4
acaagtttgt acaaaaaagc aggctaagaa ggagatatac atatggcttc taactttact    60
cagttcgttc tcgtcgacaa tggcggaact ggcgacgtga ctgtcgcccc aagcaacttc   120
gctaacgggg tcgctgaatg gatcagctct aactcgcgtt cacaggctta caaagtaacc   180
tgtagcgttc gtcagagctc tgcgcagaat cgcaaataca ccatcaaagt cgaggtgcct   240
aaagtggcaa cccagactgt tggtggtgta gagcttcctg tagccgcatg gcgttcgtac   300
ttaaatatgg aactaaccat tccaattttc gctacgaatt ccgactgcga gcttattgtt   360
aaggcaatgc aaggtctcct aaaagatgga aacccgattc cctcagcaat cgcagcaaac   420
tccggcatct actaatagac gccggccatt caaacatgag gattacccat gtacccagct   480

<210> SEQ ID NO 5
<211> LENGTH: 165
<212> TYPE: DNA
<213> ORGANISM: Artificial Sequence
<220> FEATURE:
<223> OTHER INFORMATION: T7-Rz2
<220> FEATURE:
<221> NAME/KEY: promoter
<222> LOCATION: (1)..(18)
<223> OTHER INFORMATION: T7
<220> FEATURE:

```
<221> NAME/KEY: stem_loop
<222> LOCATION: (19)..(67)
<223> OTHER INFORMATION: shRNA
<220> FEATURE:
<221> NAME/KEY: misc_RNA
<222> LOCATION: (68)..(130)
<223> OTHER INFORMATION: HDV ribozyme
<220> FEATURE:
<221> NAME/KEY: misc_feature
<222> LOCATION: (131)..(140)
<223> OTHER INFORMATION: AT spacer
<220> FEATURE:
<221> NAME/KEY: stem_loop
<222> LOCATION: (141)..(159)
<223> OTHER INFORMATION: MS2 specific packing sequence
<220> FEATURE:
<221> NAME/KEY: misc_feature
<222> LOCATION: (160)..(165)
<223> OTHER INFORMATION: NcoI restriction site

<400> SEQUENCE: 5
taatacgact cactataggc ttgtgatgct tcagccaaat caagagtttg gctgaagcat     60
cacaagcggc cggcatggtc ccagcctcct cgctggcgcc ggctgggcaa cattcgtggc    120
gaatgggacc atatatatat acatgaggat tacccatgtc catgg                    165

<210> SEQ ID NO 6
<211> LENGTH: 221
<212> TYPE: DNA
<213> ORGANISM: Artificial Sequence
<220> FEATURE:
<223> OTHER INFORMATION: T7-Rz3
<220> FEATURE:
<221> NAME/KEY: promoter
<222> LOCATION: (1)..(18)
<223> OTHER INFORMATION: T7
<220> FEATURE:
<221> NAME/KEY: misc_RNA
<222> LOCATION: (19)..(74)
<223> OTHER INFORMATION: Hammerhead ribozyme
<220> FEATURE:
<221> NAME/KEY: stem_loop
<222> LOCATION: (75)..(123)
<223> OTHER INFORMATION: shRNA
<220> FEATURE:
<221> NAME/KEY: misc_RNA
<222> LOCATION: (124)..(186)
<223> OTHER INFORMATION: HDV ribozyme
<220> FEATURE:
<221> NAME/KEY: misc_feature
<222> LOCATION: (187)..(196)
<223> OTHER INFORMATION: AT spacer
<220> FEATURE:
<221> NAME/KEY: stem_loop
<222> LOCATION: (197)..(215)
<223> OTHER INFORMATION: MS2 specific packing sequence
<220> FEATURE:
<221> NAME/KEY: misc_feature
<222> LOCATION: (216)..(221)
<223> OTHER INFORMATION: NcoI restriction site

<400> SEQUENCE: 6
taatacgact cactataggg gagagcacac aagcctgatg agtccgtgag gacgaaacgg     60
tacccggtac cgtcgcttgt gatgcttcag ccaaatcaag agtttggctg aagcatcaca    120
agcggccggc atggtcccag cctcctcgct ggcgccggct gggcaacatt cgtggcgaat    180
gggaccatat atatatacat gaggattacc catgtccatg g                        221

<210> SEQ ID NO 7
<211> LENGTH: 179
<212> TYPE: DNA
<213> ORGANISM: Artificial Sequence
```

-continued

<220> FEATURE:
<223> OTHER INFORMATION: T7-Rz6
<220> FEATURE:
<221> NAME/KEY: misc_feature
<222> LOCATION: (1)..(6)
<223> OTHER INFORMATION: BamHI restriciton site
<220> FEATURE:
<221> NAME/KEY: promoter
<222> LOCATION: (7)..(24)
<223> OTHER INFORMATION: T7
<220> FEATURE:
<221> NAME/KEY: stem_loop
<222> LOCATION: (25)..(74)
<223> OTHER INFORMATION: shRNA
<220> FEATURE:
<221> NAME/KEY: misc_RNA
<222> LOCATION: (75)..(137)
<223> OTHER INFORMATION: HDV ribozyme
<220> FEATURE:
<221> NAME/KEY: stem_loop
<222> LOCATION: (147)..(165)
<223> OTHER INFORMATION: MS2 specific packing sequence
<220> FEATURE:
<221> NAME/KEY: misc_feature
<222> LOCATION: (174)..(179)
<223> OTHER INFORMATION: NcoI restriciton site

<400> SEQUENCE: 7
ggatcctaat acgactcact ataggcaagc tgaccctgaa gttctcaaga ggaacttcag      60
ggtcagcttg ccaaggccgg catggtccca gcctcctcgc tggcgccggc tgggcaacat     120
tcgtggcgaa tgggaccacg cttcaaacat gaggattacc catgtcgaag cgaccatgg     179

<210> SEQ ID NO 8
<211> LENGTH: 362
<212> TYPE: DNA
<213> ORGANISM: Artificial Sequence
<220> FEATURE:
<223> OTHER INFORMATION: T7-Rz8
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(24)
<223> OTHER INFORMATION: T7
<220> FEATURE:
<221> NAME/KEY: misc_RNA
<222> LOCATION: (25)..(84)
<223> OTHER INFORMATION: Hammerhead ribozyme
<220> FEATURE:
<221> NAME/KEY: misc_feature
<222> LOCATION: (85)..(105)
<223> OTHER INFORMATION: sense strand siRNA
<220> FEATURE:
<221> NAME/KEY: misc_RNA
<222> LOCATION: (106)..(168)
<223> OTHER INFORMATION: HDV ribozyme
<220> FEATURE:
<221> NAME/KEY: misc_feature
<222> LOCATION: (169)..(172)
<223> OTHER INFORMATION: AT spacer
<220> FEATURE:
<221> NAME/KEY: misc_RNA
<222> LOCATION: (173)..(239)
<223> OTHER INFORMATION: Hammerhead ribozyme
<220> FEATURE:
<221> NAME/KEY: misc_feature
<222> LOCATION: (240)..(262)
<223> OTHER INFORMATION: antisense strand siRNA
<220> FEATURE:
<221> NAME/KEY: misc_RNA
<222> LOCATION: (263)..(325)
<223> OTHER INFORMATION: HDV ribozyme
<220> FEATURE:

<220> FEATURE:
<221> NAME/KEY: stem_loop
<222> LOCATION: (263)..(325)
<223> OTHER INFORMATION: MS2 specific packing sequence
<220> FEATURE:
<221> NAME/KEY: misc_feature
<222> LOCATION: (263)..(325)
<223> OTHER INFORMATION: NcoI restriction site

<400> SEQUENCE: 8

```
ggatcctaat acgactcact atagggagaa tgaacttcag ggtcagcttg ctgatgaggc    60
gcttcggcgc cgaaacaccg tgtccaagct gaccctgaag ttcatggccg gcatggtccc   120
agcctcctcg ctggcgccgg ctgggcaaca ttcgtggcga atgggaccat tagccaagct   180
gaccctgaag ttcatctgat gagactccga attcggagtc gaaacacggt aaccgtgtca   240
tgaacttcag ggtcagcttg gcggccggca tggtcccagc ctcctcgctg gcgccggctg   300
ggcaacattc gtggcgaatg ggacccattc aaacatgagg attacccatg tcgaagccat   360
gg                                                                  362
```

<210> SEQ ID NO 9
<211> LENGTH: 168
<212> TYPE: DNA
<213> ORGANISM: Artificial Sequence
<220> FEATURE:
<223> OTHER INFORMATION: T7-Rz1
<220> FEATURE:
<221> NAME/KEY: promoter
<222> LOCATION: (1)..(18)
<223> OTHER INFORMATION: T7
<220> FEATURE:
<221> NAME/KEY: misc_RNA
<222> LOCATION: (19)..(64)
<223> OTHER INFORMATION: Hammerhead ribozyme
<220> FEATURE:
<221> NAME/KEY: misc_RNA
<222> LOCATION: (65)..(113)
<223> OTHER INFORMATION: siRNA
<220> FEATURE:
<221> NAME/KEY: misc_RNA
<222> LOCATION: (114)..(162)
<223> OTHER INFORMATION: Hammerhead ribozyme
<220> FEATURE:
<221> NAME/KEY: misc_feature
<222> LOCATION: (163)..(168)
<223> OTHER INFORMATION: NcoI restriction site

<400> SEQUENCE: 9

```
taatacgact cactataggc tcgagcaagc ctgatgaggc gcttcggcgc cgaaacaccg    60
tgtcgcttgt gatgcttcag ccaaatcaag agtttggctg aagcatcaca agctcaccgg   120
atgtgctctc cggtctgatg agtccgtgag gacgaaagct tgccatgg                168
```

<210> SEQ ID NO 10
<211> LENGTH: 251
<212> TYPE: DNA
<213> ORGANISM: Artificial Sequence
<220> FEATURE:
<223> OTHER INFORMATION: T7-Rz4
<220> FEATURE:
<221> NAME/KEY: promoter
<222> LOCATION: (1)..(18)
<223> OTHER INFORMATION: T7
<220> FEATURE:
<221> NAME/KEY: misc_RNA
<222> LOCATION: (19)..(98)
<223> OTHER INFORMATION: Hammerhead ribozyme
<220> FEATURE:
<221> NAME/KEY: misc_RNA
<222> LOCATION: (99)..(146)
<223> OTHER INFORMATION: siRNA

```
<220> FEATURE:
<221> NAME/KEY: misc_RNA
<222> LOCATION: (147)..(245)
<223> OTHER INFORMATION: Hammerhead ribozyme
<220> FEATURE:
<221> NAME/KEY: misc_feature
<222> LOCATION: (246)..(251)
<223> OTHER INFORMATION: NcoI restriction site

<400> SEQUENCE: 10
taatacgact cactataggg agaacgccgg ccattcaaat agtaaataat agagggtcag    60
cttgctgatg aggcgcttcg gcgccgaaac accgtgtcca agctgaccct gaagttcatc   120
aagagtgaac ttcagggtca gcttgtcacc ggatgtgctc tccggtctga tgagtccgtg   180
aggacgaaac aagctgaccc tgaagttcac tacgccggcc attcaaacat gaggattacc   240
catgtccatg g                                                       251

<210> SEQ ID NO 11
<211> LENGTH: 468
<212> TYPE: DNA
<213> ORGANISM: Artificial Sequence
<220> FEATURE:
<223> OTHER INFORMATION: long sense strand RNA
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(26)
<223> OTHER INFORMATION: T7
<220> FEATURE:
<221> NAME/KEY: misc_RNA
<222> LOCATION: (27)..(318)
<223> OTHER INFORMATION: long sense strand RNA
<220> FEATURE:
<221> NAME/KEY: stem_loop
<222> LOCATION: (319)..(337)
<223> OTHER INFORMATION: MS2 specific packing sequence
<220> FEATURE:
<221> NAME/KEY: terminator
<222> LOCATION: (338)..(468)
<223> OTHER INFORMATION: Transcription terminator

<400> SEQUENCE: 11
ggatcctaat acgactcact atagggagat gggtggtgat cttggacaga tctacaggcg    60
attggtcaca gctgtgaacg agattgagaa gagggttcca tttctcacg acgacaggct   120 tggatttctc accttctgtc caaccaatct tggaaccact gtccgggcat cagtccatat   180
taaggtgccc aagctggctg ccaacaaggc aaaacttgag gaagttgctg cacgatacaa   240
ccttcaggtc cgtggtactc gaggagaaca cacagaagct gagggaggag tctatgacat   300
ctcaaacaag aggaggaaac atgaggatca cccatgtgcg gccgcgctgc caccgctgag   360
caataactag cataaccct tggggcctct aaacgggtct tgagggtttt tttgctgaaa   420
cctcaggcat ttgagaagca cacggtcaca ctgcttccgg tagtcaat                468

<210> SEQ ID NO 12
<211> LENGTH: 467
<212> TYPE: DNA
<213> ORGANISM: Artificial Sequence
<220> FEATURE:
<223> OTHER INFORMATION: long antisense strand RNA
<220> FEATURE:
<221> NAME/KEY: misc_feature
<222> LOCATION: (1)..(6)
<223> OTHER INFORMATION: BamHI restriction site
<220> FEATURE:
```

<221> NAME/KEY: promoter
<222> LOCATION: (7)..(26)
<223> OTHER INFORMATION: T7
<220> FEATURE:
<221> NAME/KEY: misc_RNA
<222> LOCATION: (27)..(317)
<223> OTHER INFORMATION: long antisense RNA
<220> FEATURE:
<221> NAME/KEY: stem_loop
<222> LOCATION: (318)..(336)
<223> OTHER INFORMATION: MS2 specific packing sequence
<220> FEATURE:
<221> NAME/KEY: terminator
<222> LOCATION: (337)..(467)
<223> OTHER INFORMATION: Transcription terminator

<400> SEQUENCE: 12

```
ggatcctaat acgactcact atagggtcct cctcttgttt gagatgtcat agactcctcc    60
ctcagcttct gtgtgttctc ctcgagtacc acggacctga aggttgtatc gtgcagcaac   120
ttcctcaagt tttgccttgt tggcagccag cttgggcacc ttaatatgga ctgatgcccg   180
gacagtggtt ccaagattgg ttggacagaa ggtgagaaat ccaagcctgt cgtcgtgaga   240
aaatggaacc ctcttctcaa tctcgttcac agctgtgacc aatcgcctgt agatctgtcc   300
aagatcacca cccatctaca tgaggatcac ccatgtgcgg ccgcgctgcc accgctgagc   360
aataactagc ataacccctt ggggcctcta acgggtctt gagggttttt tgctgaaac    420 ctcaggcatt tgagaagcac acggtcacac tgcttccggt agtcaat                467
```

<210> SEQ ID NO 13
<211> LENGTH: 319
<212> TYPE: DNA
<213> ORGANISM: Artificial Sequence
<220> FEATURE:
<223> OTHER INFORMATION: long bulged RNA
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(26)
<223> OTHER INFORMATION: T7
<220> FEATURE:
<221> NAME/KEY: stem_loop
<222> LOCATION: (27)..(45)
<223> OTHER INFORMATION: MS2 specific packing sequence
<220> FEATURE:
<221> NAME/KEY: misc_RNA
<222> LOCATION: (46)..(146)
<223> OTHER INFORMATION: antisense strand long bulged RNA
<220> FEATURE:
<221> NAME/KEY: misc_RNA
<222> LOCATION: (147)..(155)
<223> OTHER INFORMATION: loop region of long bulged RNA
<220> FEATURE:
<221> NAME/KEY: misc_RNA
<222> LOCATION: (156)..(256)
<223> OTHER INFORMATION: sense strand long bulged RNA
<220> FEATURE:
<221> NAME/KEY: misc_feature
<222> LOCATION: (179)..(181)
<223> OTHER INFORMATION: bulge
<220> FEATURE:
<221> NAME/KEY: misc_feature
<222> LOCATION: (205)..(207)
<223> OTHER INFORMATION: bulge
<220> FEATURE:
<221> NAME/KEY: misc_feature
<222> LOCATION: (231)..(233)
<223> OTHER INFORMATION: bulge
<220> FEATURE:
<221> NAME/KEY: misc_RNA
<222> LOCATION: (257)..(319)
<223> OTHER INFORMATION: HDV ribozyme

<400> SEQUENCE: 13

| | | |
|---|---|---|
| ggatcctaat acgactcact atagggacat gaggatcacc catgtggaca gatctacagg | 60 |
| cgataatacc tgagattgag aagagggttc aatacctcga cgacaggctt ggatttaata | 120 |
| cctgggcatc agtccatatt aaaatacctg acccatattt taatatggac tgatgccccc | 180 |
| atattaaatc caagcctgtc gtcgccatat tgaaccctct tctcaatctc ccatattatc | 240 |
| gcctgtagat ctgtccggcc ggcatggtcc cagcctcctc gctggcgccg gctgggcaac | 300 |
| attcgtggcg aatgggacc | 319 |

<210> SEQ ID NO 14
<211> LENGTH: 157
<212> TYPE: DNA
<213> ORGANISM: Artificial Sequence
<220> FEATURE:
<223> OTHER INFORMATION: A. tristis shRNA (single)
<220> FEATURE:
<221> NAME/KEY: misc_feature
<222> LOCATION: (1)..(6)
<223> OTHER INFORMATION: BamHI restriciton site
<220> FEATURE:
<221> NAME/KEY: promoter
<222> LOCATION: (7)..(26)
<223> OTHER INFORMATION: T7
<220> FEATURE:
<221> NAME/KEY: stem_loop
<222> LOCATION: (27)..(45)
<223> OTHER INFORMATION: MS2 specific packing sequence
<220> FEATURE:
<221> NAME/KEY: misc_RNA
<222> LOCATION: (46)..(66)
<223> OTHER INFORMATION: sense strand siRNA
<220> FEATURE:
<221> NAME/KEY: misc_RNA
<222> LOCATION: (67)..(73)
<223> OTHER INFORMATION: loop of siRNA
<220> FEATURE:
<221> NAME/KEY: misc_RNA
<222> LOCATION: (74)..(94)
<223> OTHER INFORMATION: antisense strand siRNA
<220> FEATURE:
<221> NAME/KEY: misc_RNA
<222> LOCATION: (95)..(157)
<223> OTHER INFORMATION: HDV ribozyme

<400> SEQUENCE: 14

| | | |
|---|---|---|
| ggatcctaat acgactcact atagggacat gaggatcacc catgtaaggg catcagtcca | 60 |
| tattaatcaa gagttaatat ggactgatgc ccttggccgg catggtccca gcctcctcgc | 120 |
| tggcgccggc tgggcaacat tcgtggcgaa tgggacc | 157 |

<210> SEQ ID NO 15
<211> LENGTH: 233
<212> TYPE: DNA
<213> ORGANISM: Artificial Sequence
<220> FEATURE:
<223> OTHER INFORMATION: A. tristis shRNA (multiple)
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(26)
<223> OTHER INFORMATION: T7
<220> FEATURE:
<221> NAME/KEY: stem_loop
<222> LOCATION: (27)..(45)

```
<223> OTHER INFORMATION: MS2 specific pac
<220> FEATURE:
<221> NAME/KEY: misc_feature
<222> LOCATION: (46)..(54)
<223> OTHER INFORMATION: TAA spacer
<220> FEATURE:
<221> NAME/KEY: misc_RNA
<222> LOCATION: (55)..(75)
<223> OTHER INFORMATION: sense strand first siRNA
<220> FEATURE:
<221> NAME/KEY: misc_RNA
<222> LOCATION: (76)..(82)
<223> OTHER INFORMATION: loop of first siRNA
<220> FEATURE:
<221> NAME/KEY: misc_RNA
<222> LOCATION: (83)..(105)
<223> OTHER INFORMATION: antisense strand first siRNA
<220> FEATURE:
<221> NAME/KEY: misc_feature
<222> LOCATION: (106)..(112)
<223> OTHER INFORMATION: TAA spacer
<220> FEATURE:
<221> NAME/KEY: misc_RNA
<222> LOCATION: (113)..(133)
<223> OTHER INFORMATION: sense strand second siRNA
<220> FEATURE:
<221> NAME/KEY: misc_RNA
<222> LOCATION: (134)..(140)
<223> OTHER INFORMATION: loop of second siRNA
<220> FEATURE:
<221> NAME/KEY: misc_RNA
<222> LOCATION: (141)..(163)
<223> OTHER INFORMATION: antisense strand second siRNA
<220> FEATURE:
<221> NAME/KEY: misc_feature
<222> LOCATION: (164)..(170)
<223> OTHER INFORMATION: TA spacer
<220> FEATURE:
<221> NAME/KEY: misc_RNA
<222> LOCATION: (171)..(233)
<223> OTHER INFORMATION: HDV ribozyme

<400> SEQUENCE: 15
ggatcctaat acgactcact atagggacat gaggatcacc catgtaataa taataagggc     60
atcagtccat attaatcaag agttaatatg gactgatgcc cttcataata ataagaagtt    120
gctgcacgat acatcaagag tgtatcgtgc agcaacttct tcataataat ggccggcatg    180
gtcccagcct cctcgctggc gccggctggg caacattcgt ggcgaatggg acc           233

<210> SEQ ID NO 16
<211> LENGTH: 176
<212> TYPE: DNA
<213> ORGANISM: Artificial Sequence
<220> FEATURE:
<223> OTHER INFORMATION: half looped shRNA
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(26)
<223> OTHER INFORMATION: T7
<220> FEATURE:
<221> NAME/KEY: stem_loop
<222> LOCATION: (27)..(45)
<223> OTHER INFORMATION: MS2 specific packing sequence
<220> FEATURE:
<221> NAME/KEY: misc_RNA
<222> LOCATION: (46)..(66)
<223> OTHER INFORMATION: sense strand siRNA
<220> FEATURE:
<221> NAME/KEY: misc_RNA
<222> LOCATION: (67)..(69)
<223> OTHER INFORMATION: first half loop
```

```
<220> FEATURE:
<221> NAME/KEY: stem_loop
<222> LOCATION: (70)..(87)
<223> OTHER INFORMATION: second MS2 specific packing sequence
<220> FEATURE:
<221> NAME/KEY: misc_RNA
<222> LOCATION: (88)..(92)
<223> OTHER INFORMATION: second half loop
<220> FEATURE:
<221> NAME/KEY: misc_RNA
<222> LOCATION: (93)..(113)
<223> OTHER INFORMATION: antisense strand siRNA
<220> FEATURE:
<221> NAME/KEY: misc_RNA
<222> LOCATION: (114)..(176)
<223> OTHER INFORMATION: HDV ribozyme

<400> SEQUENCE: 16
ggatcctaat acgactcact atagggacat gaggatcacc catgtaaggg catcagtcca      60
tattaatcaa catgaggatc acccatgtag agttaatatg gactgatgcc cttggccggc     120
atggtcccag cctcctcgct ggcgccggct gggcaacatt cgtggcgaat gggacc        176

<210> SEQ ID NO 17
<211> LENGTH: 982
<212> TYPE: DNA
<213> ORGANISM: Artificial Sequence
<220> FEATURE:
<223> OTHER INFORMATION: bacterial expression construct (E. coli)
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(25)
<223> OTHER INFORMATION: T7
<220> FEATURE:
<221> NAME/KEY: stem_loop
<222> LOCATION: (33)..(52)
<223> OTHER INFORMATION: first MS2 specific packing sequence
<220> FEATURE:
<221> NAME/KEY: misc_feature
<222> LOCATION: (53)..(74)
<223> OTHER INFORMATION: first MS2 sequence spacer
<220> FEATURE:
<221> NAME/KEY: gene
<222> LOCATION: (75)..(794)
<223> OTHER INFORMATION: EGFP gene
<220> FEATURE:
<221> NAME/KEY: misc_feature
<222> LOCATION: (795)..(809)
<223> OTHER INFORMATION: second MS2 sequence spacer
<220> FEATURE:
<221> NAME/KEY: stem_loop
<222> LOCATION: (810)..(828)
<223> OTHER INFORMATION: second MS2 specific packing sequence
<220> FEATURE:
<221> NAME/KEY: misc_feature
<222> LOCATION: (829)..(843)
<223> OTHER INFORMATION: third MS2 sequence spacer
<220> FEATURE:
<221> NAME/KEY: misc_RNA
<222> LOCATION: (844)..(906)
<223> OTHER INFORMATION: HDV ribozyme
<220> FEATURE:
<221> NAME/KEY: misc_feature
<222> LOCATION: (907)..(914)
<223> OTHER INFORMATION: NotI restriction site
<220> FEATURE:
<221> NAME/KEY: terminator
<222> LOCATION: (915)..(982)
<223> OTHER INFORMATION: Transcription terminator

<400> SEQUENCE: 17
```

-continued

```
ggatcctaat acgactcact ataggccatt cacacatgag gatcacccat gtggaagaca      60
acggagtttg aagcatggtg agcaagggcg aggagctgtt caccggggtg gtgcccatcc     120
tggtcgagct ggacggcgac gtaaacggcc acaagttcag cgtgtccggc gagggcgagg     180
gcgatgccac ctacggcaag ctgaccctga agttcatctg caccaccggc aagctgcccg     240
tgccctggcc caccctcgtg accaccctga cctacggcgt gcagtgcttc agccgctacc     300
ccgaccacat gaagcagcac gacttcttca agtccgccat gcccgaaggc tacgtccagg     360
agcgcaccat cttcttcaag gacgacggca actacaagac ccgcgccgag gtgaagttcg     420
agggcgacac cctggtgaac cgcatcgagc tgaagggcat cgacttcaag gaggacggca     480
acatcctggg gcacaagctg gagtacaact acaacagcca caacgtctat atcatggccg     540
acaagcagaa gaacggcatc aaggtgaact tcaagatccg ccacaacatc gaggacggca     600
gcgtgcagct cgccgaccac taccagcaga acacccccat cggcgacggc cccgtgctgc     660
tgcccgacaa ccactacctg agcacccagt ccgccctgag caaagacccc aacgagaagc     720
gcgatcacat ggtcctgctg gagttcgtga ccgccgccgg gatcactctc ggcatggacg     780
agctgtacaa gtagacgccg gccattcaga catgaggatc acccatgtcg aagacaacaa     840
agaggccggc atggtcccag cctcctcgct ggcgccggct gggcaacatt cgtggcgaat     900
gggaccgcgg ccgcgctgcc accgctgagc aataactagc ataacccctt ggggcctcta     960
aacgggtctt gaggggtttt tt                                              982
```

```
<210> SEQ ID NO 18
<211> LENGTH: 1398
<212> TYPE: DNA
<213> ORGANISM: Artificial Sequence
<220> FEATURE:
<223> OTHER INFORMATION: dicotyledenous plant expression construct
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(18)
<223> OTHER INFORMATION: T7
<220> FEATURE:
<221> NAME/KEY: misc_feature
<222> LOCATION: (19)..(33)
<223> OTHER INFORMATION: first MS2 sequence spacer
<220> FEATURE:
<221> NAME/KEY: stem_loop
<222> LOCATION: (34)..(53)
<223> OTHER INFORMATION: first MS2 specific packing sequence
<220> FEATURE:
<221> NAME/KEY: misc_feature
<222> LOCATION: (54)..(63)
<223> OTHER INFORMATION: second MS2 sequence spacer
<220> FEATURE:
<221> NAME/KEY: misc_feature
<222> LOCATION: (64)..(139)
<223> OTHER INFORMATION: first Carnation Italian ringspot virus
      sequence
<220> FEATURE:
<221> NAME/KEY: gene
<222> LOCATION: (140)..(859)
<223> OTHER INFORMATION: EGFP gene
<220> FEATURE:
<221> NAME/KEY: misc_feature
<222> LOCATION: (860)..(1210)
<223> OTHER INFORMATION: second Carnation Italian ringspot virus
      sequence
<220> FEATURE:
<221> NAME/KEY: misc_feature
<222> LOCATION: (1211)..(1225)
<223> OTHER INFORMATION: third MS2 sequence spacer
```

```
<220> FEATURE:
<221> NAME/KEY: stem_loop
<222> LOCATION: (1226)..(1244)
<223> OTHER INFORMATION: second MS2 specific packing sequence
<220> FEATURE:
<221> NAME/KEY: misc_feature
<222> LOCATION: (1245)..(1259)
<223> OTHER INFORMATION: fourth MS2 sequence spacer
<220> FEATURE:
<221> NAME/KEY: misc_RNA
<222> LOCATION: (1260)..(1322)
<223> OTHER INFORMATION: HDV ribozyme
<220> FEATURE:
<221> NAME/KEY: misc_feature
<222> LOCATION: (1323)..(1330)
<223> OTHER INFORMATION: NotI restriction site
<220> FEATURE:
<221> NAME/KEY: terminator
<222> LOCATION: (1331)..(1398)
<223> OTHER INFORMATION: Transcription terminator

<400> SEQUENCE: 18
ggatcctaat acgactcact ataggccatt cacacatgag gatcacccat gtggaagaca      60
acagaaatat ctcaggattt gaccgtccgg tgagttgcgc ttatcacttg cgtaaggtat     120
ttctctcttc attgttcata tggtgagcaa gggcgaggag ctgttcaccg gggtggtgcc     180
catcctggtc gagctggacg gcgacgtaaa cggccacaag ttcagcgtgt ccggcgaggg     240
cgagggcgat gccacctacg gcaagctgac cctgaagttc atctgcacca ccggcaagct     300
gcccgtgccc tggcccaccc tcgtgaccac cctgacctac ggcgtgcagt gcttcagccg     360
ctaccccgac cacatgaagc agcacgactt cttcaagtcc gccatgcccg aaggctacgt     420
ccaggagcgc accatcttct tcaaggacga cggcaactac aagacccgcg ccgaggtgaa     480
gttcgagggc gacaccctgg tgaaccgcat cgagctgaag ggcatcgact tcaaggagga     540
cggcaacatc ctggggcaca gctggagtac caactacaac agccacaacg tctatatcat     600
ggccgacaag cagaagaacg gcatcaaggt gaacttcaag atccgccaca acatcgagga     660
cggcagcgtg cagctcgccg accactacca gcagaacacc cccatcggcg acggccccgt     720
gctgctgccc gacaaccact acctgagcac ccagtccgcc ctgagcaaag accccaacga     780
gaagcgcgat cacatggtcc tgctggagtt cgtgaccgcc gccggatca ctctcggcat      840 ggacgagctg tacaagtagg ttcgctgaaa cgagtgtaaa tctggcatag catacaggtt     900
actcttgttg ggttctagat gttatgatga cgagtcggtt cgggctccgc actaggtttg     960
gtcacctagg ggatggagat atggaaaggg tctcgtgtgc tgttagacgg tcgtaagacg    1020
cgcttgcaac atgggcctat gaccggataa gtcatagcaa tactagccaa catgaatagg    1080
attcctgttt acgaaagtta gatgtcactt gtggaaacgg acccagacac ggttgatctc    1140
accttcgggg gggctataga gatcgctgga agcactaccg gacaaccgga acattgcaga    1200
aatgcagccc acgccggcca ttcagacatg aggatcaccc atgtcgaaga caacaaagag    1260
gccggcatgg tcccagcctc ctcgctggcg ccggctgggc aacattcgtg gcgaatggga    1320
ccgcggccgc gctgccaccg ctgagcaata actagcataa ccccttgggg cctctaaacg    1380
ggtcttgagg ggttttttt                                                 1398

<210> SEQ ID NO 19
<211> LENGTH: 1246
<212> TYPE: DNA
<213> ORGANISM: Artificial Sequence
<220> FEATURE:
<223> OTHER INFORMATION: monocotyledenous plant expression construct
<220> FEATURE:
```

<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(24)
<223> OTHER INFORMATION: T7
<220> FEATURE:
<221> NAME/KEY: misc_feature
<222> LOCATION: (25)..(33)
<223> OTHER INFORMATION: first MS2 sequence spacer
<220> FEATURE:
<221> NAME/KEY: stem_loop
<222> LOCATION: (34)..(52)
<223> OTHER INFORMATION: first MS2 specific packing sequence
<220> FEATURE:
<221> NAME/KEY: misc_feature
<222> LOCATION: (53)..(62)
<223> OTHER INFORMATION: second MS2 sequence spacer
<220> FEATURE:
<221> NAME/KEY: misc_feature
<222> LOCATION: (63)..(139)
<223> OTHER INFORMATION: first Carnation Italian ringspot virus sequence
<220> FEATURE:
<221> NAME/KEY: gene
<222> LOCATION: (140)..(859)
<223> OTHER INFORMATION: EGFP coding sequence
<220> FEATURE:
<221> NAME/KEY: misc_feature
<222> LOCATION: (860)..(1058)
<223> OTHER INFORMATION: second Carnation Italian ringspot virus sequence
<220> FEATURE:
<221> NAME/KEY: misc_feature
<222> LOCATION: (959)..(971)
<223> OTHER INFORMATION: Maize necrotic streak virus sequence
<220> FEATURE:
<221> NAME/KEY: misc_feature
<222> LOCATION: (1059)..(1073)
<223> OTHER INFORMATION: third MS2 sequence spacer
<220> FEATURE:
<221> NAME/KEY: stem_loop
<222> LOCATION: (1074)..(1092)
<223> OTHER INFORMATION: second MS2 specific packing sequence
<220> FEATURE:
<221> NAME/KEY: misc_feature
<222> LOCATION: (1093)..(1107)
<223> OTHER INFORMATION: fourth MS2 sequence spacer
<220> FEATURE:
<221> NAME/KEY: misc_RNA
<222> LOCATION: (1108)..(1170)
<223> OTHER INFORMATION: HDV ribozyme
<220> FEATURE:
<221> NAME/KEY: misc_feature
<222> LOCATION: (1171)..(1178)
<223> OTHER INFORMATION: NotI restriction site
<220> FEATURE:
<221> NAME/KEY: terminator
<222> LOCATION: (1179)..(1246)
<223> OTHER INFORMATION: Transcription termnator

<400> SEQUENCE: 19
ggatcctaat acgactcact ataggccatt cacacatgag gatcacccat gtggaagaca 60
acagaaatat ctcaggattt gaccgtccgg tgagttgcgc ttatcacttg cgtaaggtat 120
ttctctcttc attgttcata tggtgagcaa gggcgaggag ctgttcaccg gggtggtgcc 180
catcctggtc gagctggacg gcgacgtaaa cggccacaag ttcagcgtgt ccggcgaggg 240
cgagggcgat gccacctacg gcaagctgac cctgaagttc atctgcacca ccggcaagct 300
gcccgtgccc tggcccaccc tcgtgaccac cctgacctac ggcgtgcagt gcttcagccg 360
ctaccccgac cacatgaagc agcacgactt cttcaagtcc gccatgcccg aaggctacgt 420
ccaggagcgc accatcttct tcaaggacga cggcaactac aagacccgcg ccgaggtgaa 480

```
gttcgagggc gacaccctgg tgaaccgcat cgagctgaag ggcatcgact tcaaggagga      540
cggcaacatc ctggggcaca agctggagta caactcaaac agccacaacg tctatatcat      600
ggccgacaag cagaagaacg gcatcaaggt gaacttcaag atccgccaca acatcgagga      660
cggcagcgtg cagctcgccg accactacca gcagaacacc cccatcggcg acggccccgt      720
gctgctgccc gacaaccact acctgagcac ccagtccgcc ctgagcaaag accccaacga      780
gaagcgcgat cacatggtcc tgctggagtt cgtgaccgcc gccgggatca ctctcggcat      840
ggacgagctg tacaagtagt gtctgatgat gtgaggaacg tggactgtga tgtggtggtg      900
cggtaccatg gctggtcacc atggtaatgc gtagggcaac acagttcatt aagactcact      960
gatgatggca ccagacacgg ttgatctcac cttcgggggg ctatagaga tcgctggaag     1020 cactaccgga caaccggaac attgcagaaa tgcagcccac gccggccatt cagacatgag     1080
gatcacccat gtcgaagaca acaaagaggc cggcatggtc ccagcctcct cgctggcgcc     1140
ggctgggcaa cattcgtggc gaatgggacc gcggccgcgc tgccaccgct gagcaataac     1200
tagcataacc ccttggggcc tctaaacggg tcttgagggg tttttt                    1246
```

<210> SEQ ID NO 20
<211> LENGTH: 1774
<212> TYPE: DNA
<213> ORGANISM: Artificial Sequence
<220> FEATURE:
<223> OTHER INFORMATION: mammalian expression construct
<220> FEATURE:
<221> NAME/KEY: misc_feature
<222> LOCATION: (1)..(6)
<223> OTHER INFORMATION: BamHI restriction site
<220> FEATURE:
<221> NAME/KEY: promoter
<222> LOCATION: (7)..(24)
<223> OTHER INFORMATION: T7
<220> FEATURE:
<221> NAME/KEY: misc_feature
<222> LOCATION: (25)..(33)
<223> OTHER INFORMATION: first MS2 sequence spacer
<220> FEATURE:
<221> NAME/KEY: stem_loop
<222> LOCATION: (34)..(52)
<223> OTHER INFORMATION: first MS2 specific packing sequence
<220> FEATURE:
<221> NAME/KEY: misc_feature
<222> LOCATION: (53)..(62)
<223> OTHER INFORMATION: second MS2 sequence spacer
<220> FEATURE:
<221> NAME/KEY: misc_feature
<222> LOCATION: (63)..(561)
<223> OTHER INFORMATION: Encephalomyocarditis virus IRES sequence
<220> FEATURE:
<221> NAME/KEY: gene
<222> LOCATION: (562)..(1343)
<223> OTHER INFORMATION: EGFP gene
<220> FEATURE:
<221> NAME/KEY: polyA_signal
<222> LOCATION: (1344)..(1586)
<223> OTHER INFORMATION: SV40 late poly(A) signal sequence
<220> FEATURE:
<221> NAME/KEY: misc_feature
<222> LOCATION: (1587)..(1601)
<223> OTHER INFORMATION: third MS2 sequence spacer
<220> FEATURE:
<221> NAME/KEY: stem_loop
<222> LOCATION: (1602)..(1620)
<223> OTHER INFORMATION: second MS2 specific packing sequence
<220> FEATURE:
<221> NAME/KEY: misc_feature
<222> LOCATION: (1621)..(1635)
<223> OTHER INFORMATION: fourth MS2 sequence spacer
<220> FEATURE:

```
<221> NAME/KEY: misc_RNA
<222> LOCATION: (1636)..(1698)
<223> OTHER INFORMATION: HDV ribozyme
<220> FEATURE:
<221> NAME/KEY: misc_feature
<222> LOCATION: (1699)..(1706)
<223> OTHER INFORMATION: NotI restriction site
<220> FEATURE:
<221> NAME/KEY: terminator
<222> LOCATION: (1707)..(1774)
<223> OTHER INFORMATION: Transcription terminator

<400> SEQUENCE: 20
```

| | | | | | |
|---|---|---|---|---|---|
| ggatcctaat | acgactcact | ataggccatt | cacacatgag | gatcacccat | gtggaagaca | 60 |
| accccccccc | taacgttact | ggccgaagcc | gcttggaata | aggccggtgt | gcgtttgtct | 120 |
| atatgttatt | ttccaccata | ttgccgtctt | ttggcaatgt | gagggcccgg | aaacctggcc | 180 |
| ctgtcttctt | gacgagcatt | cctaggggtc | tttcccctct | cgccaaagga | atgcaaggtc | 240 |
| tgttgaatgt | cgtgaaggaa | gcagttcctc | tggaagcttc | ttgaagacaa | acaacgtctg | 300 |
| tagcgaccct | ttgcaggcag | cggaaccccc | cacctggcga | caggtgcctc | tgcggccaaa | 360 |
| agccacgtgt | ataagataca | cctgcaaagg | cggcacaacc | ccagtgccac | gttgtgagtt | 420 |
| ggatagttgt | ggaaagagtc | aaatggctct | cctcaagcgt | attcaacaag | ggctgaagg | 480 |
| atgcccagaa | ggtaccccat | tgtatgggat | ctgatctggg | gcctcggtgc | acatgcttta | 540 |
| catgtgttta | gtcgaggtta | aaaaacgtct | aggccccccg | aaccacgggg | acgtggtttt | 600 |
| cctttgaaaa | acacgatgat | aatatggtga | gcaagggcga | ggagctgttc | accggggtgg | 660 |
| tgcccatcct | ggtcgagctg | gacggcgacg | taaacggcca | caagttcagc | gtgtccggcg | 720 |
| agggcgaggg | cgatgccacc | tacggcaagc | tgaccctgaa | gttcatctgc | accaccggca | 780 |
| agctgcccgt | gccctggccc | accctcgtga | ccaccctgac | ctacggcgtg | cagtgcttca | 840 |
| gccgctaccc | cgaccacatg | aagcagcacg | acttcttcaa | gtccgccatg | cccgaaggct | 900 |
| acgtccagga | gcgcaccatc | ttcttcaagg | acgacggcaa | ctacaagacc | cgcgccgagg | 960 |
| tgaagttcga | gggcgacacc | ctggtgaacc | gcatcgagct | gaagggcatc | gacttcaagg | 1020 |
| aggacggcaa | catcctgggg | cacaagctgg | agtacaacta | caacagccac | aacgtctata | 1080 |
| tcatggccga | caagcagaag | aacggcatca | aggtgaactt | caagatccgc | cacaacatcg | 1140 |
| aggacggcag | cgtgcagctc | gccgaccact | accagcagaa | cacccccatc | ggcgacggcc | 1200 |
| ccgtgctgct | gcccgacaac | cactacctga | gcacccagtc | cgccctgagc | aaagacccca | 1260 |
| acgagaagcg | cgatcacatg | gtcctgctgg | agttcgtgac | cgccgccggg | atcactctcg | 1320 |
| gcatggacga | gctgtacaag | tagttctaga | gcggccgctt | cgagcagaca | tgataagata | 1380 |
| cattgatgag | tttggacaaa | ccacaactag | aatgcagtga | aaaaaatgct | ttatttgtga | 1440 |
| aatttgtgat | gctattgctt | tatttgtaac | cattataagc | tgcaataaac | aagttaacaa | 1500 |
| caacaattgc | attcatttta | tgtttcaggt | tcaggggag | gtgtgggagg | ttttttaaag | 1560 |
| caagtaaaac | ctctacaaat | gtggtaacgc | cggccattca | gacatgagga | tcacccatgt | 1620 |
| cgaagacaac | aaagaggccg | gcatggtccc | agcctcctcg | ctggcgccgg | ctgggcaaca | 1680 |
| ttcgtggcga | atgggaccgc | ggccgcgctg | ccaccgctga | gcaataacta | gcataacccc | 1740 |
| ttggggcctc | taaacgggtc | ttgaggggtt | tttt | | | 1774 |

UNITED STATES PATENT AND TRADEMARK OFFICE
CERTIFICATE OF CORRECTION

PATENT NO. : 9,822,361 B2
APPLICATION NO. : 14/897577
DATED : November 21, 2017
INVENTOR(S) : Juan Pedro Humberto Arhancet et al.

It is certified that error appears in the above-identified patent and that said Letters Patent is hereby corrected as shown below:

In the Claims

- In Claim 1, Column 81, Line 4, "compromises:" should be corrected to "comprises:".

- In Claim 1, Column 81, Line 7, "non-homolous" should be corrected to "non-homologous".

- In Claim 3, Column 82, Line 3, "non-homolous" should be corrected to "non-homologous".

Signed and Sealed this
Twelfth Day of November, 2024

Katherine Kelly Vidal
*Director of the United States Patent and Trademark Office*